US009006233B2

(12) United States Patent
Cook et al.

(10) Patent No.: US 9,006,233 B2
(45) Date of Patent: Apr. 14, 2015

(54) GABAERGIC RECEPTOR SUBTYPE SELECTIVE LIGANDS AND THEIR USES

(75) Inventors: James M. Cook, Milwaukee, WI (US); Terry S. Clayton, Colorado Springs, CO (US); Hiteshkumar D. Jain, Mumbai (IN); Sundari K. Rallipalli, Oak Creek, WI (US); Yun Teng Johnson, Glendale, WI (US); Jie Yang, Renssalaer, NY (US); Michael Ming-jin Poe, Milwaukee, WI (US); Ojas A. Namjoshi, Cary, NC (US); Zhi-jian Wang, Whitefish Bay, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 245 days.

(21) Appl. No.: 13/458,168

(22) Filed: Apr. 27, 2012

(65) Prior Publication Data

US 2012/0295892 A1 Nov. 22, 2012

Related U.S. Application Data

(60) Provisional application No. 61/479,899, filed on Apr. 28, 2011.

(51) Int. Cl.
*A61K 31/5517* (2006.01)
*C07D 487/04* (2006.01)
*C07D 487/14* (2006.01)
*C07D 519/00* (2006.01)

(52) U.S. Cl.
CPC ............ *C07D 487/04* (2013.01); *C07D 487/14* (2013.01); *C07D 519/00* (2013.01)

(58) Field of Classification Search
USPC .......................................... 514/220; 540/562
See application file for complete search history.

(56) References Cited

U.S. PATENT DOCUMENTS

| | | |
|---|---|---|
| 7,119,196 B2 | 10/2006 | Cook et al. |
| 7,235,656 B2 | 6/2007 | Cook et al. |
| 7,595,395 B2 | 9/2009 | Cook et al. |
| 7,618,958 B2 | 11/2009 | Cook et al. |
| 2004/0082574 A1 | 4/2004 | Cook et al. |
| 2007/0049580 A1 | 3/2007 | Cook et al. |
| 2010/0004226 A1 | 1/2010 | Cook et al. |
| 2010/0130479 A1 | 5/2010 | Cook et al. |
| 2010/0130481 A1 | 5/2010 | Cook et al. |
| 2010/0261711 A1 | 10/2010 | Cook et al. |
| 2010/0317619 A1 | 12/2010 | Cook et al. |

FOREIGN PATENT DOCUMENTS

| WO | WO 0059503 | 10/2000 |
|---|---|---|
| WO | WO 2009046004 | 4/2009 |

OTHER PUBLICATIONS

Bombrun, A. "3,6-Dibromocarbazole Piperazine Derivatives of 2-Propanol as first inhibitors of cytochrome C release via bax channel modulation," Journal of Medicinal Chemistry, 2003, p. 4365-4368, vol. 46.
Castro, B. "Nucleophilic Properties of Gem-alkoxy Organomagnesium Compounds (II)," Bulletin de la Société Chimique de France, 1967, p. 1540-1547, fascicle 5.
Chambers, M.S. et al. "Identification of a Novel, Selective GABAA alpha five Receptor Inverse Agonist which Enhances Cognition," Journal of Medicinal Chemistry, 2003, p. 2227, vol. 46.
Choudhary, M.S. et al. "Identification of receptor domains that modify ligand binding to 5-hydroxy-tryptamine2 and 5-hydroxytryptamine1c serotonin receptors," Molecular Pharmacology, Oct. 1992, p. 627-633, vol. 42, iss. 4.
Clayton, T. et al. "An Updated Unified Pharmacophore Model of the Benzodiazepine Binding Site on gamma-Aminobutyric acid A Receptors: Correlation with Comparative Models," Current Medicinal Chemistry, 2007, p. 2755-2775, vol. 14.
Corey, E.J., et al. "A new and simple synthesis of alkoxy- and aryloxymethyllithium reagents (ROCH2Li)," Tetrahedron Letters, 1983, p. 3163-3164, vol. 242.
Corey, E.J., et al. "Enantioselective conjugate addition of rationally designed chiral cuprate reagents to 2-cycloalkenones," Journal of American Chemical Society, 1986, 7114-7116, vol. 108.
Crestani, F. et al. "Trace fear conditioning involves hippocampal alpha 5 GABAA receptors.", Proceedings of the National Academy of Sciences, 2002, p. 8980-8985, vol. 99.
Han, W. et al. "Alpha-ketoamides, Alpha -ketoesters and Alpha-diketones as HCV NS3 Protease Inhibitors," Bioorganic and Medicinal Chemistry Letters, 2000, pg. 711-713, vol. 10.
Huang, et al. "Pharmacophore/Receptor Models for GABAA/BzR Subtypes (alpha 1 beta 3 gamma 2, alpha 5 beta 3 gamma 2, and alpha six beta 3 gamma 2) via a Comprehensive Ligand-Mapping Approach," Journal of Medicinal Chemistry, 2000, p. 71-95, vol. 43.
Inaba, S. et al. "Metallic Nickel: A Coupling Reagent of Benzyl Halides and Acyl Halides to Yield Benzyl Ketones.", Tetrahedron Letters, 1983 p. 2451-2452, vol. 24.
Inaba, S. et al. "Metallic Nickel-mediated Synthesis of Ketones by the Reaction of Benzylic, Allylic, Vinylic, and Pentafluorophenyl Halides with Acid Halides," Journal of Organic Chemistry, 1985, p. 1373-1381, vol. 50.
Lehmann, R. et al. "Facile Hydrogen/Metal Exchange between butylpotassium and saturated ethers," Tetrahedron Letters, 1984, p. 745-748, vol. 25, iss. 7.
Low, K. et al. "Molecular and Neuronal Substrate for the Selective Attenuation of Anxiety," Science, 2000, p. 131, vol. 290.
McKernan, R.M. et al. "Sedative but not anxiolytic properties of benzodiazepines are mediated by the GABAA receptor α1 subtype," Nature Neuroscience, 2000, p. 587-592, vol. 3, iss. 6.

(Continued)

*Primary Examiner* — Brenda Coleman
(74) *Attorney, Agent, or Firm* — Michael Best & Friedrich LLP

(57) ABSTRACT

Described herein are α3 or α2 or α2/α3 GABAergic receptor subtype selective ligands, pharmaceutical compositions, and methods of use of such ligands and compositions in treatment of anxiety disorders, epilepsy and schizophrenia with reduced sedative and ataxic side effects. In embodiments, such as α3 or α2 or α2/α3 GABAergic receptor subtype selective ligands lack ester linkages and may be thus relatively insensitive to hydrolysis by esterases.

3 Claims, 20 Drawing Sheets

(56) References Cited

OTHER PUBLICATIONS

Noe, C.R. et al. "The Synthesis of (S)-Benzoin from Meso-hydrobenzoin," Chemische Berichte, 1985, p. 4453-4458, vol. 118.

Normant, H. et al. "Chloromethyl Ethers and Their Magnesium Derivatives.", Comptes Rendus, 1964, p. 830-832, vol. 259.

Oyama, K.I. et al. "Synthesis of Pelargonidin 3-O-6-O-acetyl-Beta-D-glucopyranoside, an acylated anthocyanin, via the corresponding kaempferol glucoside," Tetrahedron Letters, 2007, 6005-6009, vol. 48.

Pearson, W.H., et al. "Total Synthesis of the *Kopsia lapidilecta* Alkaloid (±)-Lapidilectine B," Journal of Organic Chemistry, 2004, p. 9109-9122, vol. 69.

Rudolph, U., et al. "Benzodiazepine actions mediated by specific gamma-aminobutyric acidA receptor subtypes.", Nature, Oct. 21, 1999, p. 796-800, vol. 401.

Sanchez, I. et al. "Design and Synthesis of Substituted Compounds Containing the 1,4-Benzodioxin Subunit. New Potential Calcium Antagonists," European Journal of Medicinal Chemistry, 2000, 663-676, vol. 35.

Suh, Y. et al. "Direct Preparation of Benzylic Manganese Reagents from Benzyl Halides, Sulfonates, and Phosphates and Their Reaction: Applications in Organic Synthesis," Journal of Organometallic Chemistry, 2003, p. 20-36, vol. 684.

Venkatesan, A.M. et al. "Structure-activity relationship of 6-Methylidene penems bearing tricyclic hetercocycles as broad-spectrum lactamase inhibitors: cystallographic structures show unexpected binding of 1,4-Thiazepine Intermediates," Journal of Medicinal Chemistry, 2004, p. 6556-6568, vol. 47.

Yin, W. et al. "First Enantiospecific Total Synthesis of the Important Biogenetic Intermediates, (+)-Polyneuridine and (+)-Polyneuridine Aldehyde, as well as 16-Epi-vellosimine and Macusine," American Chemical Society Organic Letters, 2007, p. 295-298, vol. 9.

Zhang, P. et al. "Synthesis of Novel Imidazobenzodiazepines as Probes of the Pharmacophore for Diazepam-insensitive GABA(A) Receptors," Journal of Medicinal Chemistry, 1995, p. 1679-1688, vol. 38.

| α$_1$ | α$_2$ | α$_3$ | α$_4$ | α$_5$ | α$_6$ |
|---|---|---|---|---|---|
| 5000 | 135 | 1027 | ND | 132 | 5000 |

| α$_1$ | α$_2$ | α$_3$ | α$_4$ | α$_5$ | α$_6$ |
|---|---|---|---|---|---|
| 1.98 | 2.5 | 11.63 | ND | 11.5 | 5000 |

| α$_1$ | α$_2$ | α$_3$ | α$_4$ | α$_5$ | α$_6$ |
|---|---|---|---|---|---|
| 54.3 | 27.14 | 25.88 | ND | 15.3 | 5000 |

SR-II-097

SR-III-38

ZJW-II-40

| Compound | α1 | α2 | α3 | α4 | α5 | α□ |
|---|---|---|---|---|---|---|
| ZJW-II-040 | 4753 | 25.54 | 31.43 | ND | 275.4 | ND |

| | YT-III-15 a1 | YT-III-15 a2 | YT-III-15 a3 | YT-III-15 a5 |
|---|---|---|---|---|
| BOTTOM | 100.0 | 100.0 | 100.0 | 100.0 |
| TOP | 231.5 | 338.5 | 502.7 | 176.4 |
| LOGEC50 | -6.353 | -6.842 | -6.396 | -6.881 |
| HILLSLOPE | 1.662 | 4.163 | 1.294 | 3.377 |
| EC50 | 4.438e-007 | 1.437e-007 | 4.013e-007 | 1.315e-007 |

| Compound | $\alpha_1$ | $\alpha_2$ | $\alpha_3$ | $\alpha_4$ | $\alpha_5$ | $\alpha_6$ |
|---|---|---|---|---|---|---|
| YT-III-15 | 73.19 | 90.45 | 141.4 | ND | 114 | ND |

HJ-I-037

| Compound | α1 | α2 | α3 | α4 | α5 | α6 |
|---|---|---|---|---|---|---|
| HJ-I-037 | 22.16 | 44.06 | 38.48 | ND | 12.15 | ND |

| Compound | α1 | α2 | α3 | α4 | α5 | α☐ |
|---|---|---|---|---|---|---|
| YT-III-31 | 36.39 | 67.85 | 129.7 | ND | 7.59 | ND |

YT-III-271

| Compound | α1 | α2 | α3 | α4 | α5 | α□ |
|---|---|---|---|---|---|---|
| YT-III-271 | 32.54 | 1.26 | 2.35 | ND | 103 | ND |

XHe-II-053

Significant metabolism at both 1 and 10 μM

HJ-I-40

Not metabolized at either 1 μM or 10 μM

XHe-II-053 Acid

Not metabolized at either 1 μM or 10 μM

BMJ-I-026

Not metabolized at either 1 μM or 10 μM

SR-II-54

Not metabolized at either 1 μM or 10 μM

SH-053-2'F-RCH3

Not metabolized at either 1 μM or 10 μM

HJ-I-037
Not metabolized at either 1 μM or 10 μM

YT-III-271
Only slight metabolism at 1 μM and no metabolism at 10 μM

ZJW-II-040
Not metabolized at either 1 μM or 10 μM

ZJW-II-065
Only slight metabolism at 1 μM and no metabolism at 10 μM

HZ-166
Only slight metabolism at 1 μM and 10 μM

YT-III-15
Significant metabolism at 1 μM but only slight metabolism at 10 μM

HZ-166-TMS

Significant metabolism at both 1 and 10 µM

JY-XHe-053

Significant metabolism at both 1 and 10 µM

SH-053-2'F-SCH3

Significant metabolism at both 1 and 10 µM

GABAERGIC RECEPTOR SUBTYPE SELECTIVE LIGANDS AND THEIR USES

CROSS-REFERENCE TO RELATED APPLICATIONS

This application claims priority to U.S. Provisional Patent Application No. 61/479,899, filed on Apr. 28, 2011, the entire contents of which are hereby incorporated by reference.

STATEMENT REGARDING FEDERALLY SPONSORED RESEARCH OR DEVELOPMENT

This invention was made with United States government support under R01 AA012407 awarded by the National Institutes of Health (NIH). The government has certain rights in this invention.

BACKGROUND

Gamma-aminobutyric acid (GABA) is the major inhibitory neurotransmitter in the central nervous system. GABA receptors are heteromeric, and are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned the number of known members of the mammalian family has grown to 21 including $\alpha$, $\beta$, and $\gamma$ subunits ($6\alpha$, $4\beta$, $4\gamma$, $1\delta$, $1\epsilon$, $1\pi$, $1\theta$, and $3\rho$).

A characteristic property of $GABA_A$ receptors is the presence of a number of modulatory sites, one of which is the benzodiazepine (BZ) site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the $\alpha 1$ subunit in combination with a $\beta$ subunit and $\gamma 2$. It has been indicated that an $\alpha$ subunit, a $\beta$ subunit and a $\gamma$ subunit constitute the minimum requirement for forming a fully functional Benzodiazepine/$GABA_A$ receptor.

Receptor subtype assemblies for BZ-sensitive $GABA_A$ receptors include amongst others the subunit combinations $\alpha 1\beta 2/3\gamma 2$, $\alpha 2\beta 2/3\gamma 2$, $\alpha 3\beta 2/3\gamma 2$, $\alpha 4\beta 2/3\gamma 2$, and $\alpha 5\beta 2/3\gamma 2$. Subtype assemblies containing an $\alpha 1$ subunit ($\alpha 1\beta 2\gamma 2$) are present in most areas of the brain and are thought to account for 40-50% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit ($\alpha 5\beta 3\gamma 2$) are expressed predominately in the hippocampus and cortex and are thought to represent about 5% of $GABA_A$ receptors in the rat. Two other major populations are the $\alpha 2\beta 2/3\gamma 2$ and $\alpha 3\beta 2/3\gamma 2$ subtypes as stated above. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain $\alpha 5$-containing subtype assemblies.

The present pharmacology of agonists acting at the BZ site of $GABA_A$ receptors suggests that $\alpha 1$ containing receptors mediate sedation, anticonvulsant activity, ataxia, and anterograde amnesia, while $\alpha 2$ and/or $\alpha 3$ $GABA_A$ receptors mediate anxiolytic activity. $\alpha 5$ containing $GABA_A$ receptors are involved in memory functions (U. Rudolph et al., Nature 1999, 401, 796; K. Löw et al., Science 2000, 290, 131; McKernan Nature Neurosci. 2000, 3, 587; F. Crestani et al., Proc. Nat. Acad. Sci. USA 2002, 99, 8980; M. S. Chambers et al., J. Med. Chem. 2003, 46, 2227).

It is believed that agents acting selectively as benzodiazepine agonists at $GABA_A/\alpha 2$, $GABA_A/\alpha 3$, and/or $GABA_A/\alpha 5$ receptors possess desirable properties. Compounds which are modulators of the benzodiazepine binding site of the $GABA_A$ receptor by acting as benzodiazepine agonists are referred to hereinafter as "$GABA_A$ receptor agonists." The $GABA_A/\alpha 1$-selective ($\alpha 1\beta 2\gamma 2$) agonists alpidem and zolpidem are clinically prescribed as hypnotic agents, suggesting that at least some of the sedation associated with known anxiolytic drugs which act at the Benzodiazepine 1 binding site is mediated through $GABA_A$ receptors containing the $\alpha 1$ subunit. Recently, two studies have shown that the majority of additive properties of diazepam are mediated by $\alpha 1$ subtypes (N. A. Ator et. al., J. Pharm. Exp. Thera. 2010, 332, 4-16; K. R. Tan et. al., Nature, 463, 769-774).

It is also known that some benzodiazepine derivatives, such as QH-ii-066, bind with high affinity to $GABA_A/\alpha 5$ receptors (Ki<10 nM), intermediate affinity to $GABA_A/\alpha 2$ and $GABA_A/\alpha 3$ (Ki<50 nM), and poorer affinity to $GABA_A/\alpha 1$ receptors (Ki>70 nM), unlike diazepam which binds with high affinity to all four diazepam-sensitive $GABA_A$ receptors (Ki<25 nM), as disclosed in Huang, et al., J. Med. Chem. 2000, 43, 71-95. However, such benzodiazepine derivatives may contain ester linkages, and may thus be sensitive to hydrolysis in vivo (e.g., by esterases). What is needed are GABAergic receptor subtype selective ligands that lack ester linkages, and are less sensitive to hydrolysis in vivo by esterases.

SUMMARY

In one aspect, the invention provides a compound of formula (I):

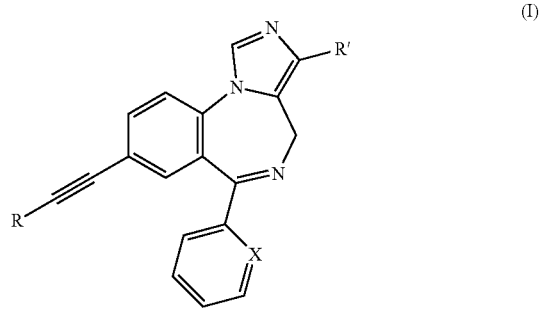

or a salt thereof, wherein:
R is —H or —Si(Me)$_3$;
X is CH, CF, CCl or N; and
R' is selected from the group consisting of —CHF$_2$, —CH$_2$CF$_2$CH$_3$, —CF$_2$CHF$_2$, —CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$,
—CH$_2$OCH$_2$OCH$_3$, —COCH$_2$CH$_3$, —C(CF$_2$)OCH$_2$CH$_3$,
—CH(CF$_3$)OCH$_2$CH$_3$, —CH(CF$_3$)NHCH$_2$CH$_3$,

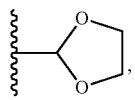

—CHO and —CH$_2$CF$_2$CH$_3$, or
R' is selected from the group consisting of:

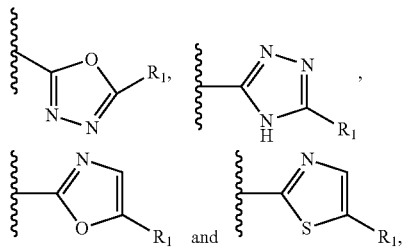

wherein each R$_1$ is independently selected from the group consisting of —CH$_3$, —CH$_2$CH$_3$ and —CH(CH$_3$)$_2$.

In another aspect, the invention provides a compound of formula (II):

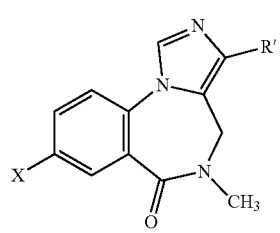

(II)

or a salt thereof, wherein:
X is Cl, Br, or F; and
R' is selected from the group consisting of —CHF$_2$, —CH$_2$CF$_2$CH$_3$, —CF$_2$CHF$_2$, —CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$, —CH$_2$OCH$_2$OCH$_3$, —COCH$_2$CH$_3$, —C(CF$_2$)OCH$_2$CH$_3$, —CH(CF$_3$)OCH$_2$CH$_3$, —CH(CF$_3$)NHCH$_2$CH$_3$,

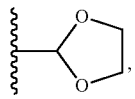

—CHO, —CH$_2$CF$_2$CH$_3$, —COSR, —NR$_1$R$_2$ and —CH$_2$NR$_1$R$_2$, wherein R is C$_1$-C$_4$ alkyl and each R$_1$ and R$_2$ are independently —H or —C$_1$-C$_4$ alkyl; or
R' is selected from the group consisting of:

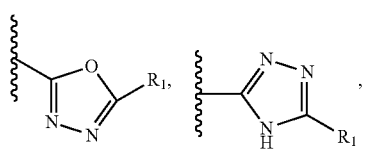

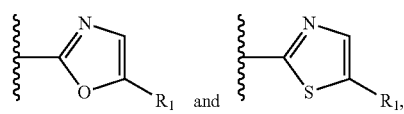

wherein each R$_1$ is independently selected from the group consisting of —CH$_3$, —CH$_2$CH$_3$ and —CH(CH$_3$)$_2$.

In another aspect, the invention provides a compound of formula (III):

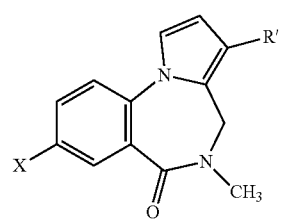

(III)

or a salt thereof, wherein:
X is Cl, Br, or F; and
R' is selected from the group consisting of —CHF$_2$, —CH$_2$CF$_2$CH$_3$, —CF$_2$CHF$_2$, —CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$, —CH$_2$OCH$_2$OCH$_3$, —COCH$_2$CH$_3$, —C(CF$_2$)OCH$_2$CH$_3$, —CH(CF$_3$)OCH$_2$CH$_3$, —CH(CF$_3$)NHCH$_2$CH$_3$,

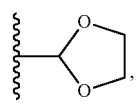 [SMILES: *C1OCCO1]

—CHO, —CH$_2$CF$_2$CH$_3$, —COSR, —NR$_1$R$_2$ and —CH$_2$NR$_1$R$_2$, wherein R is C$_1$-C$_4$ alkyl and each R$_1$ and R$_2$ are independently —H or —C$_1$-C$_4$ alkyl; or
R' is selected from the group consisting of:

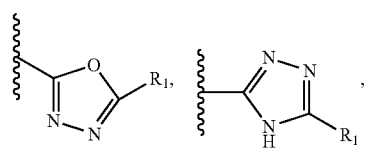

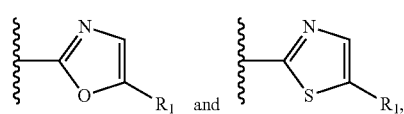

wherein each R$_1$ is independently selected from the group consisting of —CH$_3$, —CH$_2$CH$_3$ and —CH(CH$_3$)$_2$.

In another aspect, the invention provides a compound of formula (IV):

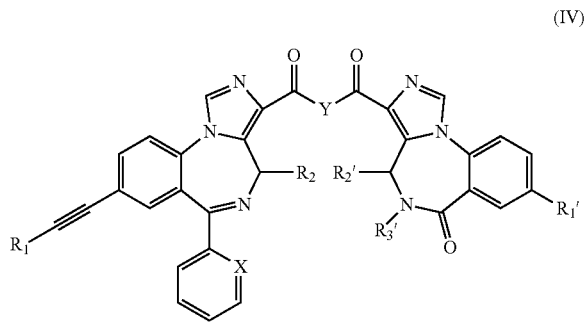

(IV)

or a salt thereof, wherein:

Y is —N(CH$_2$CH$_2$)$_2$N—, —S(CH$_2$)$_n$S—, —O(CH$_2$)$_n$O—, or —(CH$_2$)$_n$— wherein each n is independently 3, 4 or 5;

X is CH, CF, CCl or N;

R$_1$ is —H or —Si(Me)$_3$;

R$_1$' is —H, —Cl, —Br, or —C≡C—R, where R is —H or —Si(Me)$_3$;

R$_2$ is —H, —CF$_3$ or —CH$_3$; and

R$_2$' and R$_3$' are independently —H or —CH$_3$, or R$_2$' and R$_3$' are taken together with the atoms to which they are attached to form a 5-, 6-, or 7-membered saturated ring.

In another aspect, the invention provides a compound of formula (V):

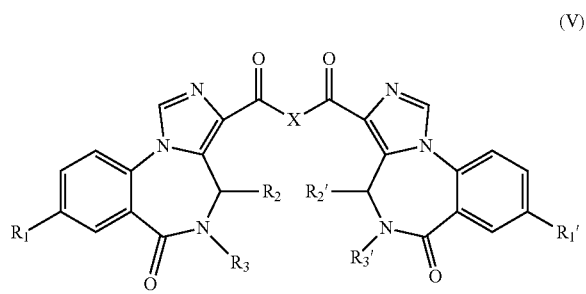

(V)

or a salt thereof, wherein:

X is —N(CH$_2$CH$_2$)$_2$N—, —S(CH$_2$)$_n$S—, or —(CH$_2$)$_n$— wherein each n is independently 3, 4 or 5;

R$_1$ and R$_1$' are independently —H, —Cl, —Br, or —C≡C—R, where R is —H or —Si(Me)$_3$;

R$_2$ and R$_3$ are independently —H or —CH$_3$, or R$_2$ and R$_3$ are taken together with the atoms to which they are attached to form a 5-, 6-, or 7-membered saturated ring;

R$_2$' and R$_3$' are independently —H or —CH$_3$, or R$_2$ and R$_3$ are taken together with the atoms to which they are attached to form a 5-, 6-, or 7-membered saturated ring.

In another aspect, the invention provides a compound of formula (VI):

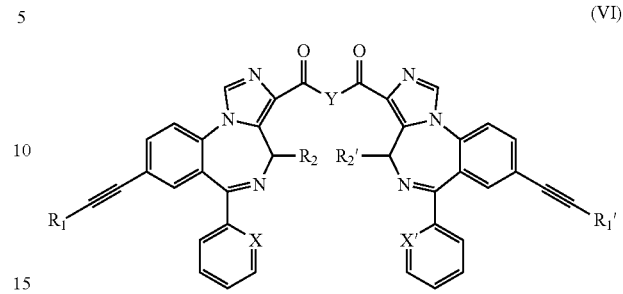

(VI)

or a salt thereof, wherein:

X and X' are independently CH, CF, CCl or N;

Y is —N(CH$_2$CH$_2$)$_2$N—, —S(CH$_2$)$_n$S—, —O(CH$_2$)$_n$O—, or —(CH$_2$)$_n$— wherein each n is independently 3, 4 or 5;

R$_1$ and R$_1$' are independently —H or —Si(Me)$_3$; and

R$_2$ and R$_2$' are independently —H or —CH$_3$.

In another aspect, the invention provides a pharmaceutical composition comprising at least one compound of formula (I), (II), (III), (IV), (V) or (VI), and a pharmaceutically acceptable carrier.

In another aspect, the invention provides a method of treating a disorder selected from an anxiety disorder, epilepsy and schizophrenia in a subject in need of treatment, comprising administering to the subject an effective amount of a compound of formula (I), (II), (III), (IV), (V) or (VI).

In another aspect, the invention provides a method of treating a disorder selected from an anxiety disorder, epilepsy and schizophrenia in a subject in need of treatment, comprising administering to the subject an effective amount of a compound of formula (Ia):

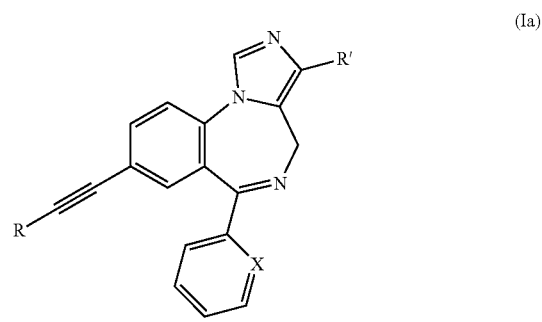

(Ia)

or a salt thereof, wherein:

R is —H or —Si(Me)$_3$;

X is CH, CF, CCl or N; and

R' is selected from the group consisting of —CHF$_2$, —CH$_2$CF$_2$CH$_3$, —CF$_2$CHF$_2$, —CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$, —CH$_2$OCH$_2$OCH$_3$, —COCH$_2$CH$_3$, —C(CF$_2$)OCH$_2$CH$_3$, —CH(CF$_3$)OCH$_2$CH$_3$, —CH(CF$_3$)NHCH$_2$CH$_3$,

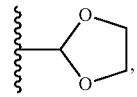

—CHO, —CH$_2$CF$_2$CH$_3$, COSR, or CONR$_1$R$_2$, wherein R, R$_1$ and R$_2$ are each independently H or C$_1$-C$_4$ alkyl, or R' is selected from the group consisting of:

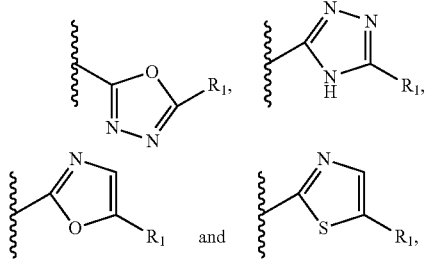

wherein each R$_1$ is independently selected from the group consisting of CH$_3$, CH$_2$CH$_3$ and CH(CH$_3$)$_2$.

In another aspect, the invention provides a method of treating a disorder selected from an anxiety disorder, epilepsy and schizophrenia in a subject in need of treatment, comprising administering to the subject an effective amount of a compound of formula (Va):

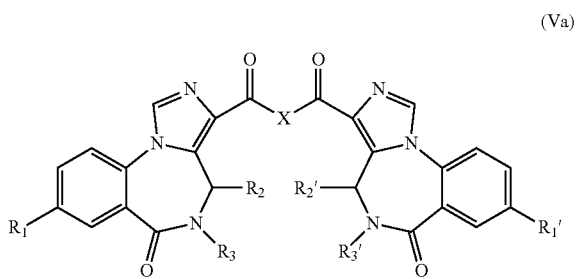

or a salt thereof, wherein:

X is —N(CH$_2$CH$_2$)$_2$N—, —S(CH$_2$)$_n$S—, —O(CH$_2$)$_n$O—, or —(CH$_2$)$_n$— wherein each n is independently 3, 4 or 5;

R$_1$ and R$_1$' are independently —H, —Cl, —Br, or —C≡C—R, where R is —H or —Si(Me)$_3$;

R$_2$ and R$_3$ are independently —H or —CH$_3$, or R$_2$ and R$_3$ are taken together with the atoms to which they are attached to form a 5-, 6-, or 7-membered saturated ring;

R$_2$' and R$_3$' are independently —H or —CH$_3$, or R$_2$ and R$_3$ are taken together with the atoms to which they are attached to form a 5-, 6-, or 7-membered saturated ring.

Other aspects and embodiments are encompassed by the disclosure and will become apparent in light of the following description and drawings.

DETAILED DESCRIPTION

Figure 1:
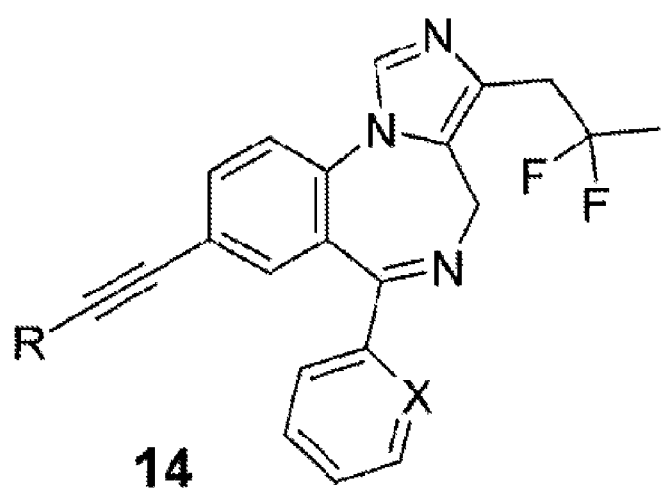
FIG. 1 shows the chemical structure of compound 14, where R=H, and X=CH, CF, CCl or N.
Figure 2:
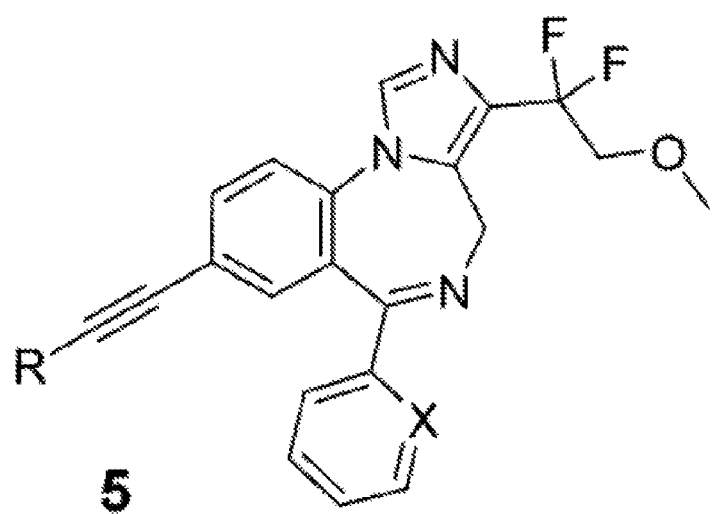
FIG. 2 shows the chemical structure of compound 5, where R=H, and X=CH, CF, CCl or N.
Figure 3:
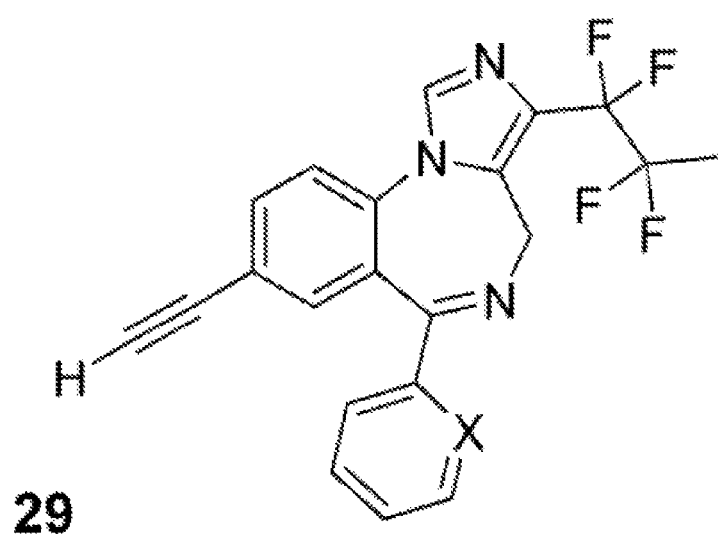
FIG. 3 shows the chemical structure of compound 29, where X=CH, CF, CCl or N.
Figure 4:
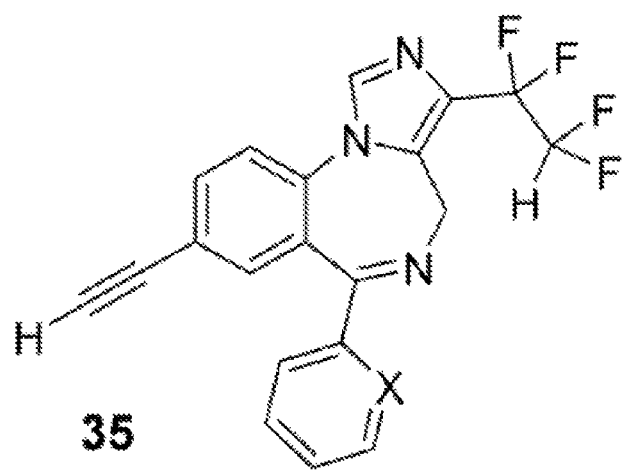
FIG. 4 shows the chemical structure of compound 35, where X=CH, CF, CCl or N.
Figure 5:
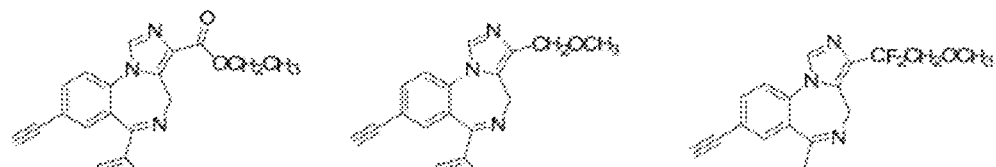
FIG. 5 shows exemplary compounds and associated data. For certain compounds, in vitro binding affinities at αxβ3γ2 GABAA/benzodiazepine site subtypes are provided, where measurements were made in duplicate and Ki values are reported in nM.
Figure 5:
Figure 5:
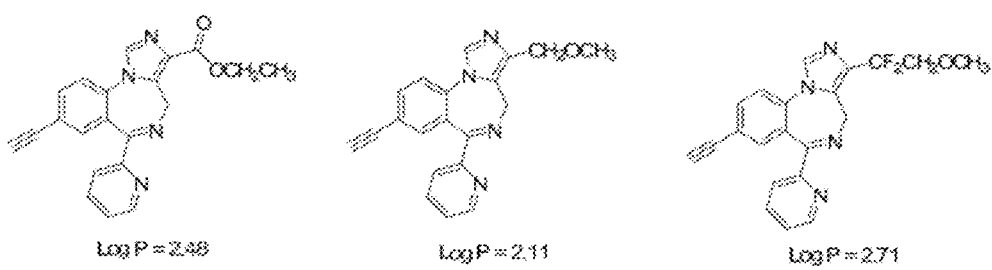
Figure 5:
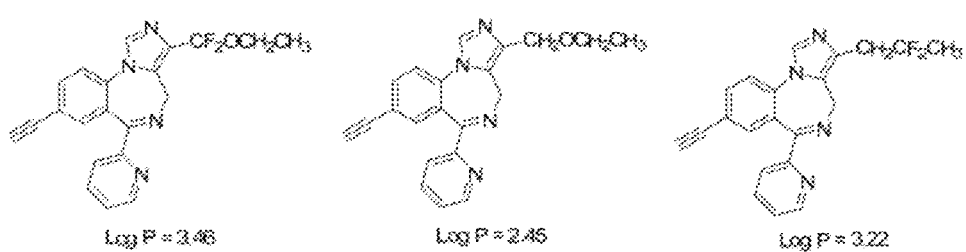
Figure 5:
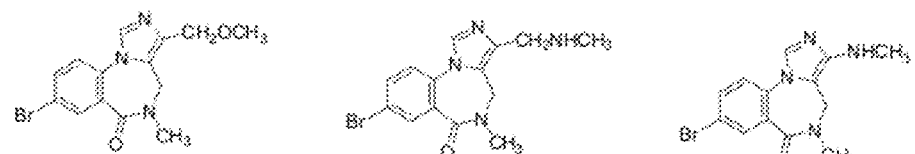
Figure 5:
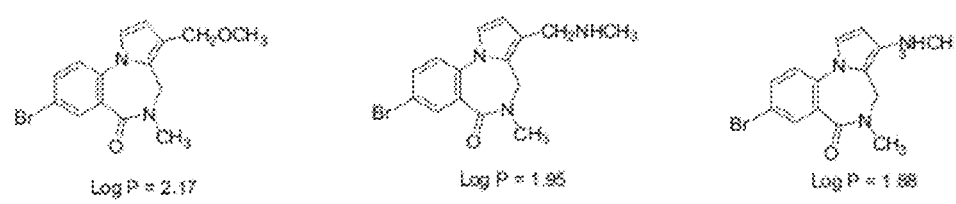
Figure 5:
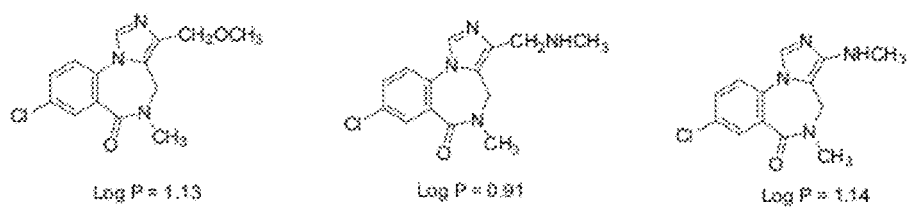
Figure 5:
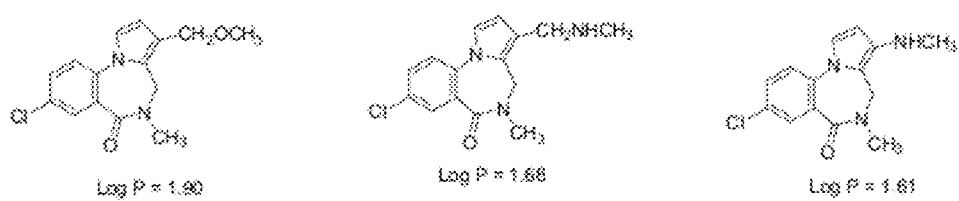
Figure 5:
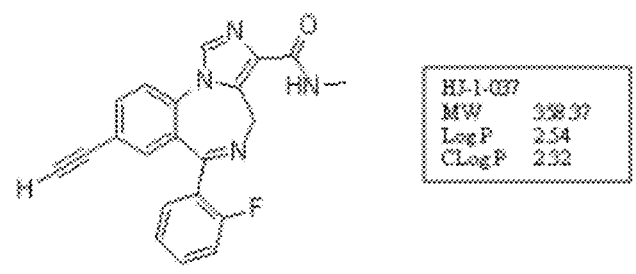
Figure 5:
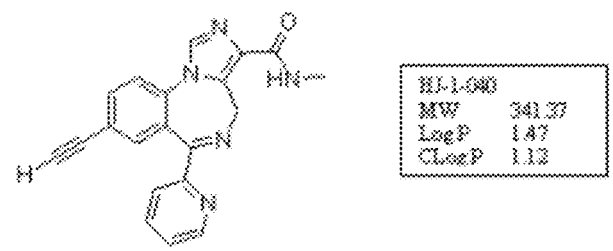
Figure 5:
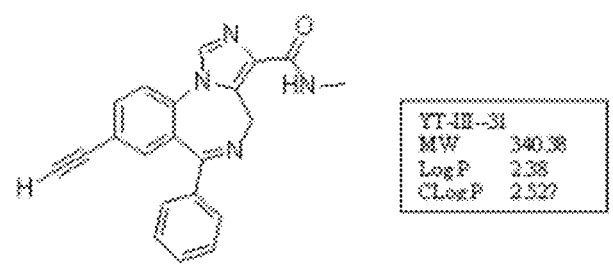
Figure 5:
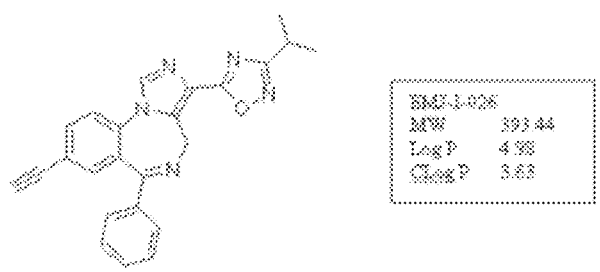
Figure 5:
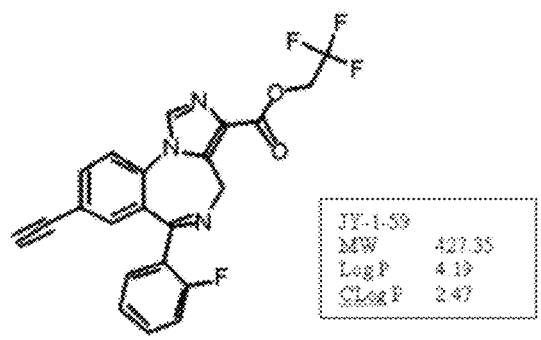
Figure 5:
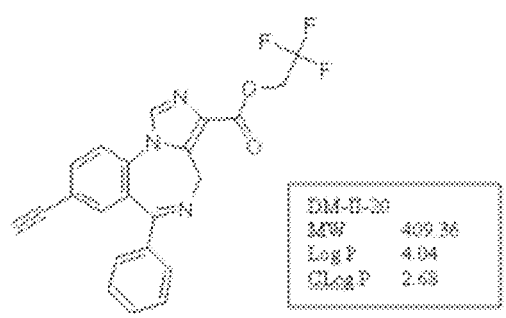
Figure 6:
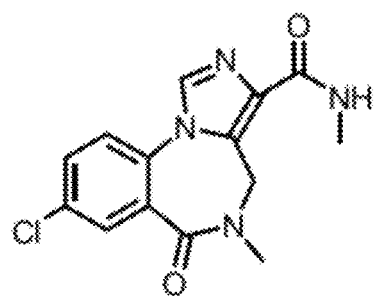
FIG. 6 shows: the structure of SR-II-097; and concentration-effect curves for SR-II-097 on α1β3γ2 (■), α2β3γ2 (▲), α3β3γ2 (♦), and α5β3γ2 (▼) GABA$_A$ receptors, using an EC3 GABA concentration, where data points represent mean±SEM from at least four oocytes from ≥2 batches.
Figure 6:
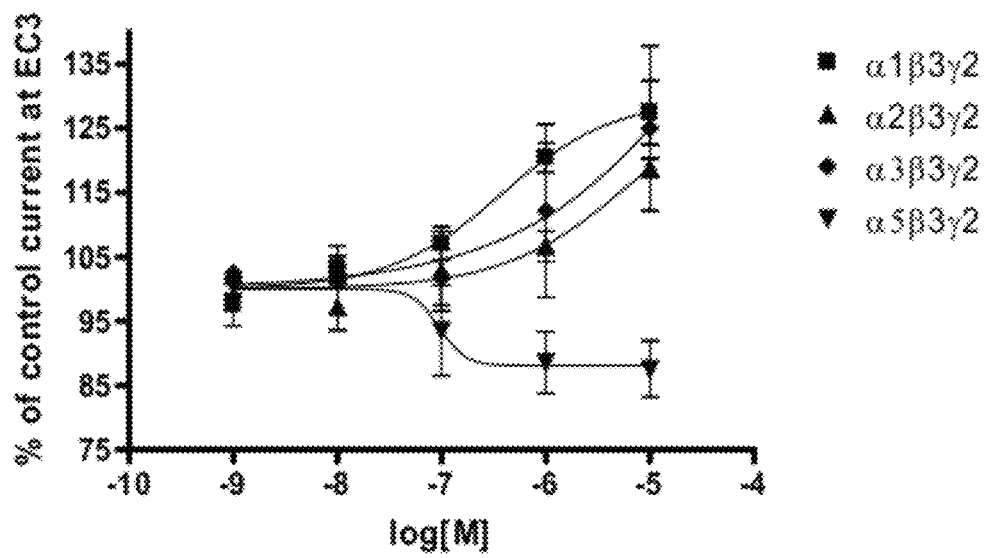
Figure 7:
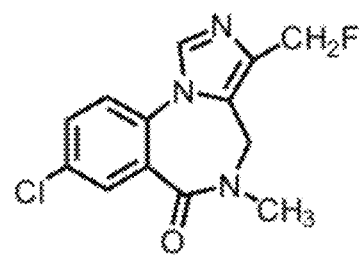
FIG. 7 shows: the structure of SR-III-38; and concentration-effect curves for SR-III-38 on α1β3γ2 (■), α2β3γ2 (▲), α3β3γ2 (▼), and α5β3γ2 (♦) GABA$_A$ receptors, using an EC3 GABA concentration, where data points represent mean±SEM from at least four oocytes from ≥2 batches.
Figure 7:
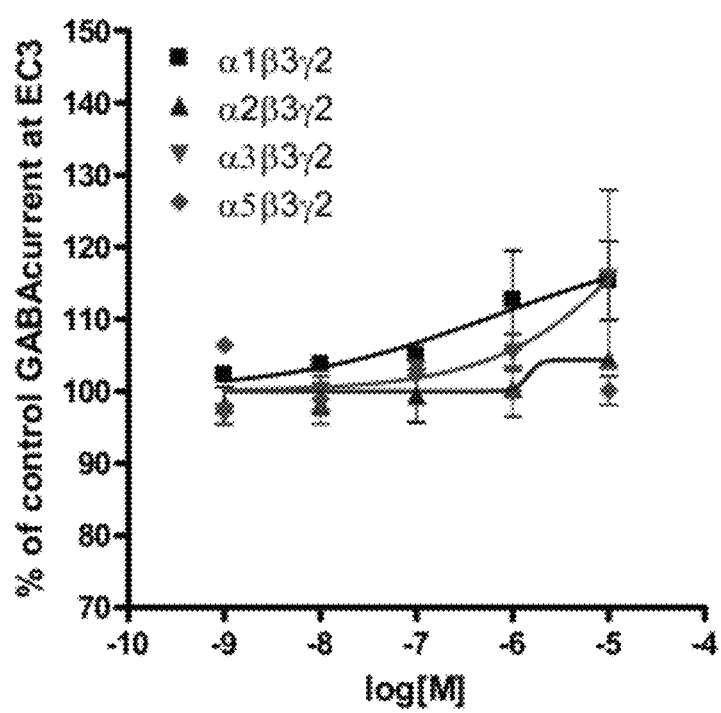
Figure 8:
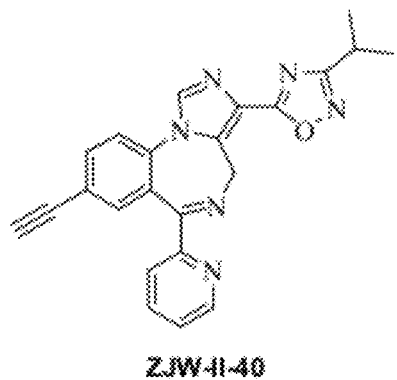
FIG. 8 shows: the structure of ZJW-II-40; concentration-effect curves for ZJW-II-40 on α1β3γ2 (■), α2β3γ2 (▲), α3β3γ2 (▼), and α5β3γ2 (♦) GABA$_A$ receptors, using an EC3 GABA concentration, where data points represent mean±SEM from at least four oocytes from 2 batches; and in vitro binding affinity at αxβ3γ2 GABA$_A$/benzodiazepine site subtypes, where measurements were made in duplicate and Ki values are reported in nM.
Figure 8:
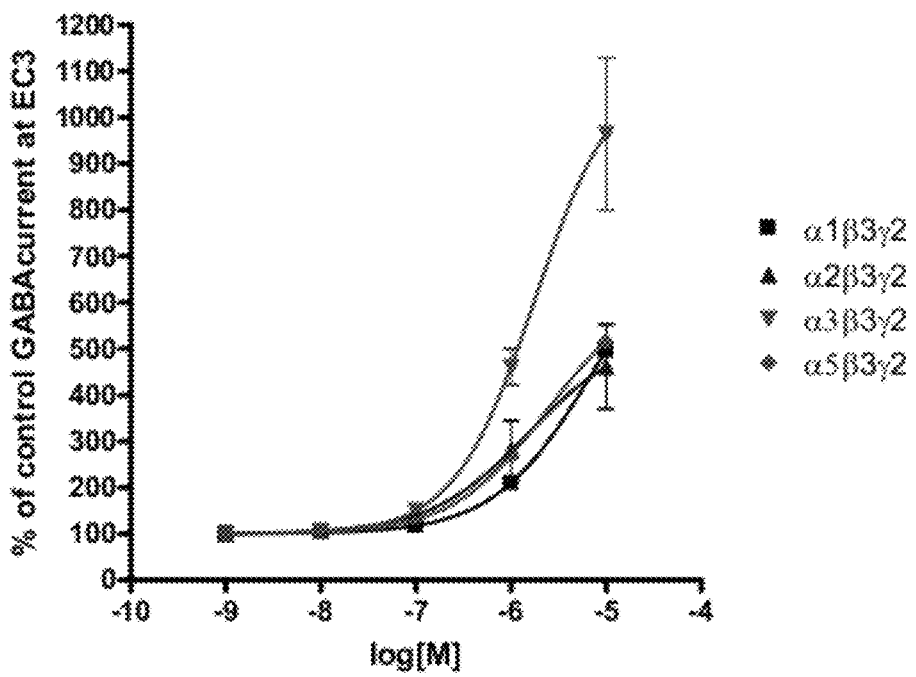
Figure 9:
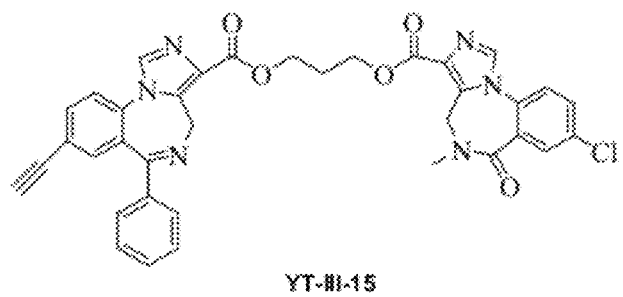
FIG. 9 shows: the structure of YT-III-15; concentration-effect curves for YT-III-15 on α1β3γ2 (■), α2β3γ2 (▲), α3β3γ2 (▼), and α5β3γ2 (♦) GABA$_A$ receptors, using an EC3 GABA concentration, where data points represent mean±SEM from at least four oocytes from ≥2 batches; and in vitro binding affinity at αxβ3γ2 GABA$_A$/benzodiazepine site subtype, where measurements were made in duplicate and Ki values are reported in nM.
Figure 9:
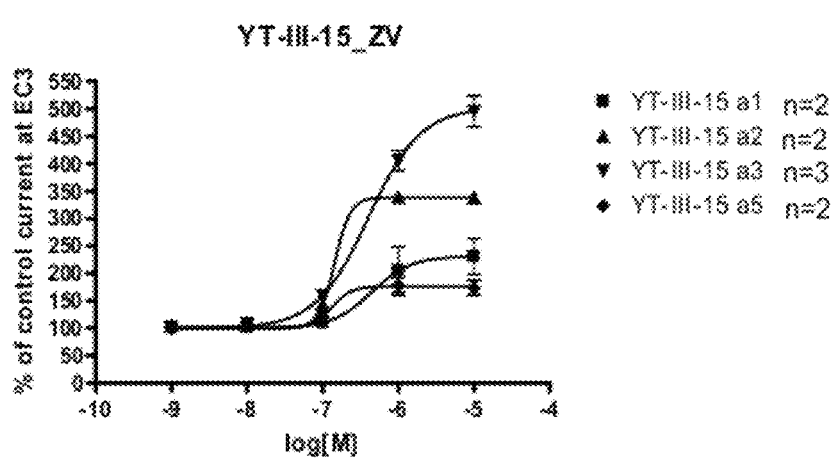
Figure 10:
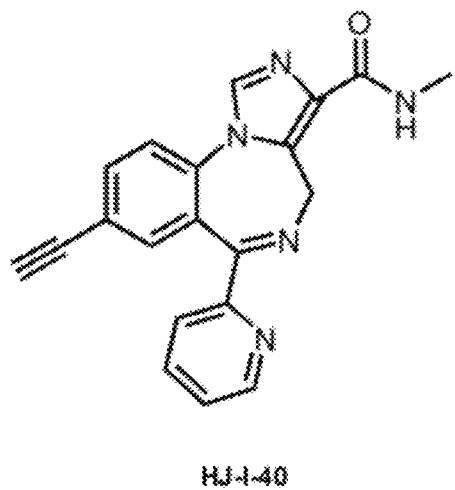
FIG. 10 shows: the structure of HJ-I-40; and concentration-effect curves for HJ-I-40 on α1β3γ2 (■), α2β3γ2 (▲), α3β3γ2 (▼), and α5β3γ2 (♦) GABA$_A$ receptors, using an EC3 GABA concentration, where data points represent mean±SEM from at least four oocytes from ≥2 batches.
Figure 10:
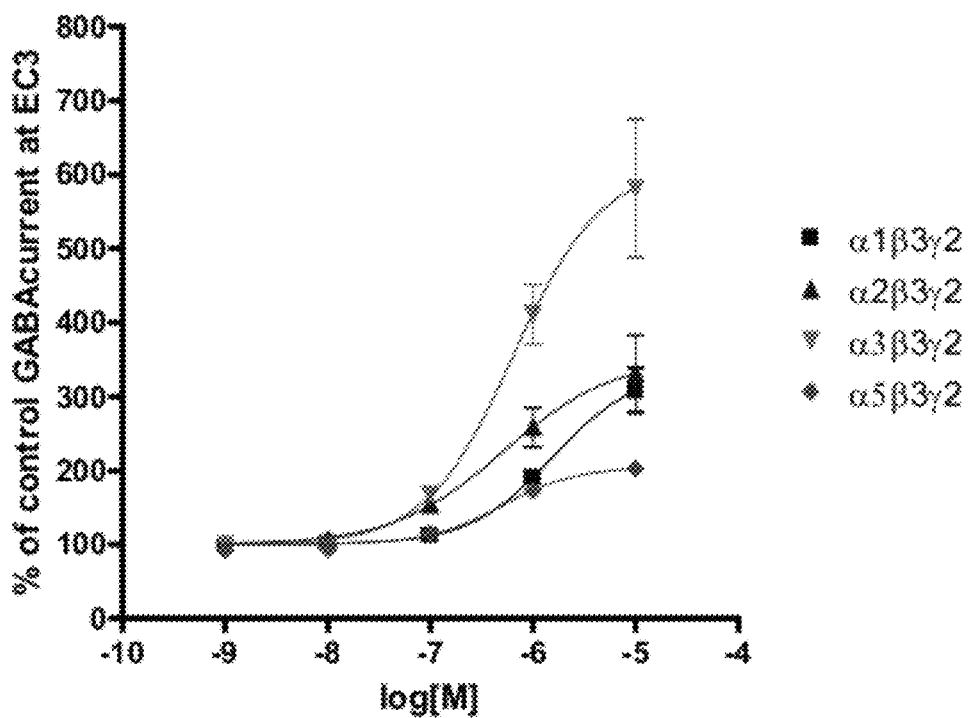
Figure 11:
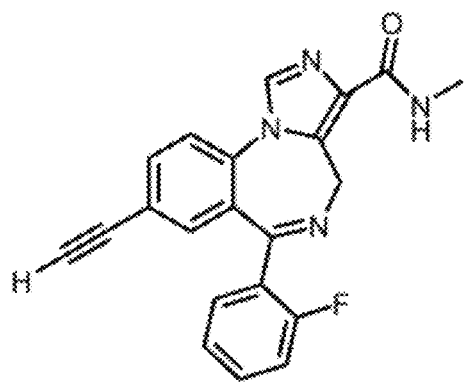
FIG. 11 shows: the structure of HJ-I-37; concentration-effect curves for HJ-I-37 on α1β3γ2 (■), α2β3γ2 (▲), α3β3γ2 (♦), and α5β3γ2 (▼) GABA$_A$ receptors, using an EC3 GABA concentration, where data points represent mean±SEM from at least four oocytes from ≥2 batches; and in vitro binding affinity at αxβ3γ2 GABA$_A$/benzodiazepine site subtypes, where measurements were made in duplicate and Ki values are reported in nM.
Figure 11:
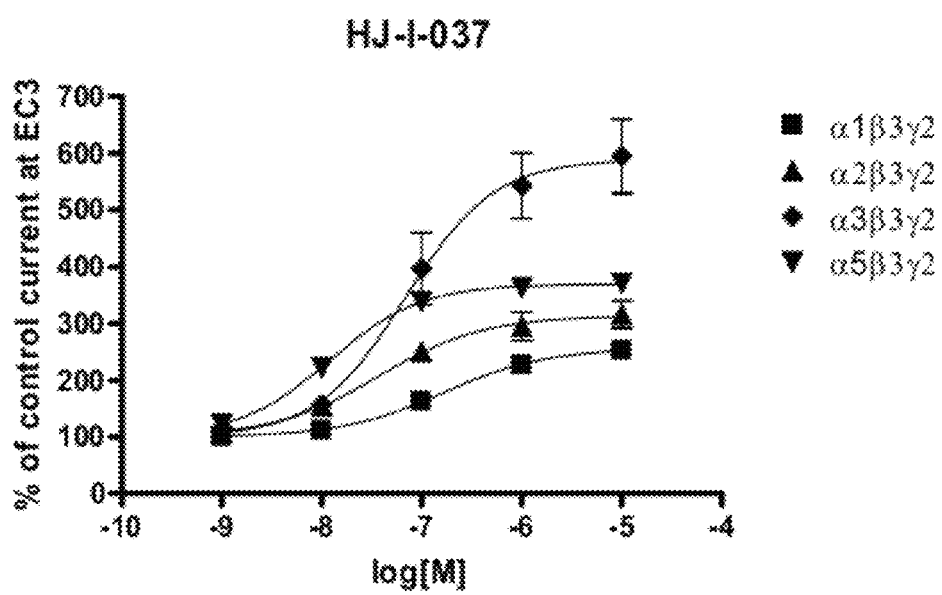
Figure 12:
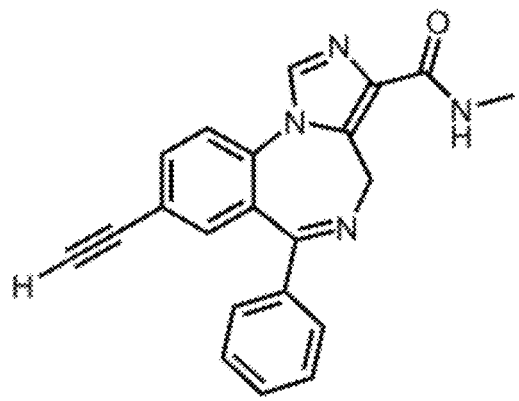
FIG. 12 shows: the structure of YT-III-31; concentration-effect curves for YT-III-31 on α1β3γ2 (■), α2β3γ2 (▲), α3β3γ2 (♦), and α5β3γ2 (▼) GABA$_A$ receptors, using an EC3 GABA concentration, where data points represent mean±SEM from at least four oocytes from ≥2 batches; and in vitro binding affinity at αxβ3γ2 GABAA/benzodiazepine site subtypes, where measurements were made in duplicate and Ki values are reported in nM.
Figure 12:
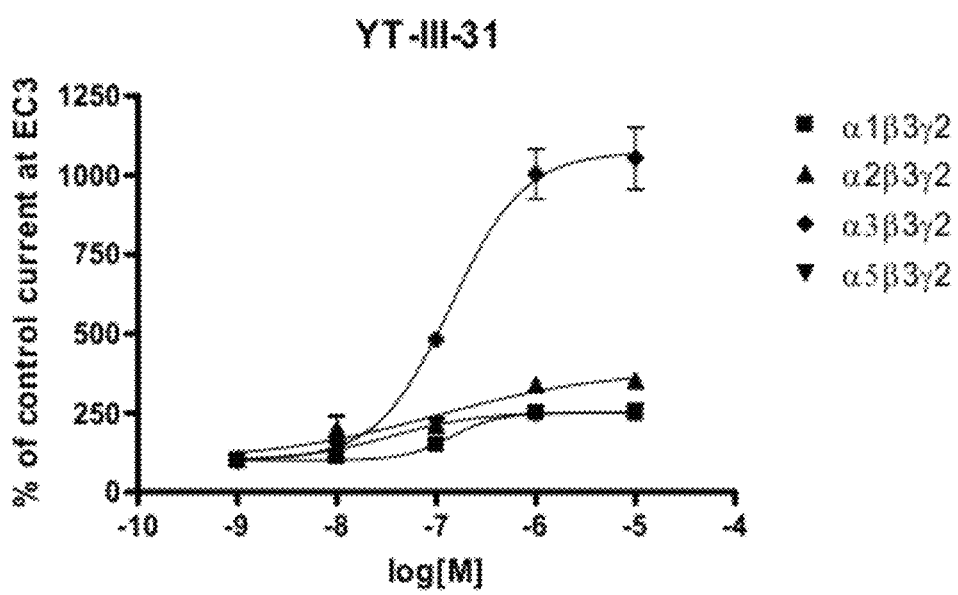
Figure 13:
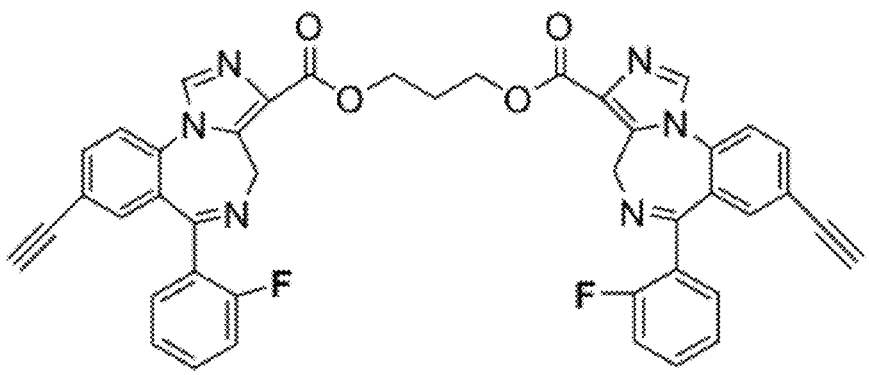
FIG. 13 shows: the structure of YT-III-271; concentration-effect curves for YT-III-271 on α1β3γ2 (■), α2β3γ2 (▲), α3β3γ2 (♦), and α5β3γ2 (▼) GABAA receptors, using an EC3 GABA concentration, where data points represent mean±SEM from at least four oocytes from ≥2 batches; and in vitro binding affinity at αxβ3γ2 GABAA/benzodiazepine site subtypes, where measurements were made in duplicate and Ki values are reported in nM.
Figure 13:
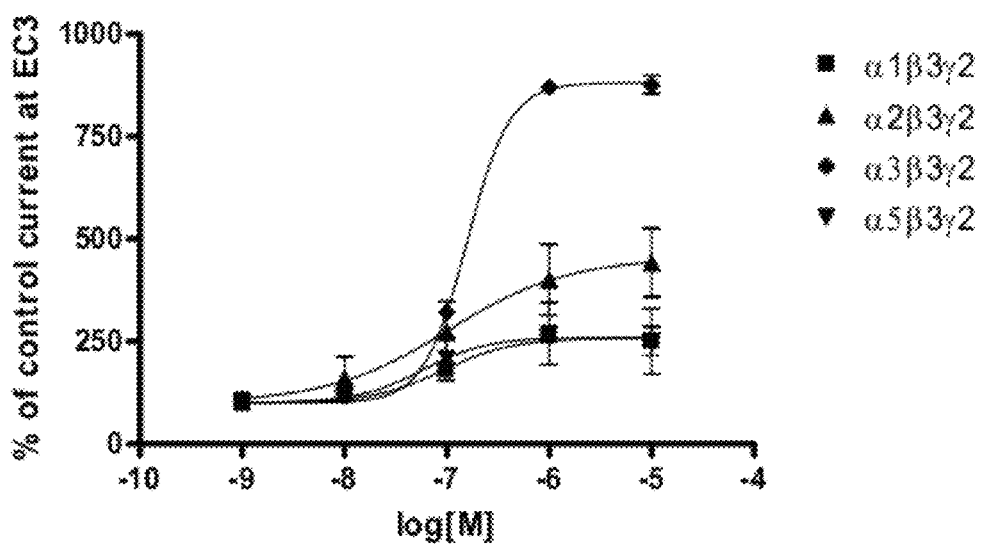

The present invention provides compounds that may be alpha2/alpha3 GABAergic receptor subtype selective ligands, pharmaceutical compositions, and methods of use of such ligands and compositions in treatment of anxiety disorders, epilepsy and schizophrenia. In embodiments, such alpha2/alpha3 GABAergic receptor subtype selective ligands lack ester linkages and are thus relatively insensitive to hydrolysis by esterases.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH₂O— optionally also recites —OCH₂—.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compounds

Compounds may be of the following formula (I):

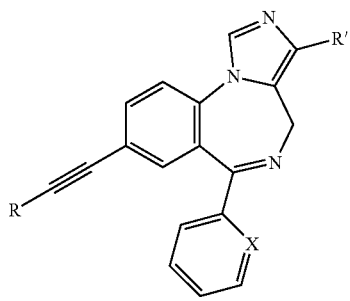

(I)

or a salt thereof, wherein:

R is —H or —Si(Me)₃;

X is CH, CF, CCl or N; and

R' is selected from the group consisting of —CHF₂, —CH₂CF₂CH₃, —CF₂CHF₂, —CF₂CF₂CH₃, —CH₂OCH₃, —CF₂CH₂OCH₃, —CF₂OCH₂CH₃, —CH₂OCH₂CH₃, —CH₂OH, —CH₂SCH₃, —CF₂CH₂CH₃, —CH₂OCH₂OCH₃, —COCH₂CH₃, —C(CF₂)OCH₂CH₃, —CH(CF₃)OCH₂CH₃, —CH(CF₃)NHCH₂CH₃,

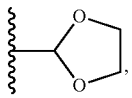

—CHO and —CH₂CF₂CH₃, or

R' is selected from the group consisting of:

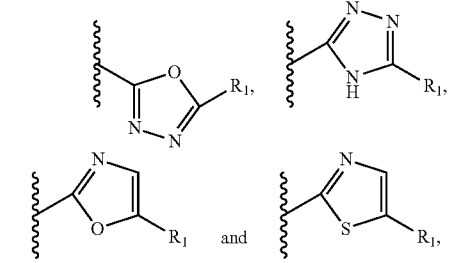

and wherein each R₁ is independently selected from the group consisting of —CH₃, —CH₂CH₃ and —CH(CH₃)₂.

In some embodiments, R is —H. In some embodiments, R is —Si(Me)₃. In some embodiments, X is CH. In some embodiments, X is N. In some embodiments, X is CF. In some embodiments, R' is selected from the group consisting of —CHF₂, —CH₂CF₂CH₃, —CF₂CHF₂, —CF₂CF₂CH₃, —CH₂OCH₃, —CF₂CH₂OCH₃, —CF₂OCH₂CH₃, —CH₂OCH₂CH₃, —CH₂OH, —CH₂SCH₃, —CF₂CH₂CH₃, —CH₂OCH₂OCH₃, —COCH₂CH₃, —C(CF₂)OCH₂CH₃, —CH(CF₃)OCH₂CH₃, —CH(CF₃)NHCH₂CH₃,

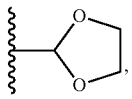

—CHO and —CH₂CF₂CH₃. In some embodiments, R' is selected from the group consisting of —CHF₂, —CH₂CF₂CH₃, —CF₂CHF₂, —CF₂CF₂CH₃, —CF₂CH₂OCH₃, —CF₂OCH₂CH₃, —CF₂CH₂CH₃, —C(CF₂)OCH₂CH₃, —CH(CF₃)OCH₂CH₃, —CH(CF₃)NHCH₂CH₃ and —CH₂CF₂CH₃. In some embodiments, R' is selected from the group consisting of

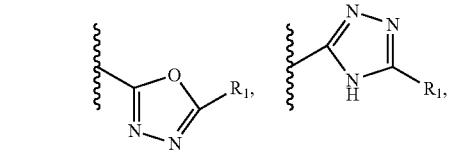

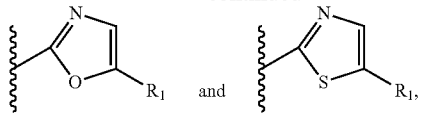 and of wherein each $R_1$ is independently selected from the group consisting of —$CH_3$, —$CH_2CH_3$ and —$CH(CH_3)_2$.

Compounds may be of the following formula (II):

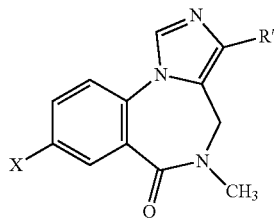

(II)

or a salt thereof, wherein:

X is Cl, Br, or F; and

R' is selected from the group consisting of —$CHF_2$, —$CH_2CF_2CH_3$, —$CF_2CHF_2$, —$CF_2CF_2CH_3$, —$CH_2OCH_3$, —$CF_2CH_2OCH_3$, —$CF_2OCH_2CH_3$, —$CH_2OCH_2CH_3$, —$CH_2OH$, —$CH_2SCH_3$, —$CF_2CH_2CH_3$, —$CH_2OCH_2OCH_3$, —$COCH_2CH_3$, —$C(CF_2)OCH_2CH_3$, —$CH(CF_3)OCH_2CH_3$, —$CH(CF_3)NHCH_2CH_3$,

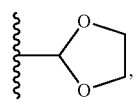

—CHO, —$CH_2CF_2CH_3$, —COSR, —$NR_1R_2$ and —$CH_2NR_1R_2$, wherein R is $C_1$-$C_4$ alkyl and each $R_1$ and $R_2$ are independently —H or —$C_1$-$C_4$ alkyl; or R' is selected from the group consisting of:

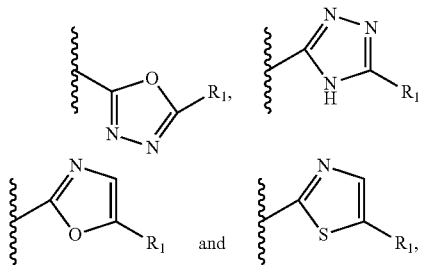

wherein each $R_1$ is independently selected from the group consisting of —$CH_3$, —$CH_2CH_3$ and —$CH(CH_3)_2$.

In some embodiments, X is F. In some embodiments, X is Cl. In some embodiments, X is Br. In some embodiments, R' is selected from the group consisting of —$CHF_2$, —$CH_2CF_2CH_3$, —$CF_2CHF_2$, —$CF_2CF_2CH_3$, —$CH_2OCH_3$, —$CF_2CH_2OCH_3$, —$CF_2OCH_2CH_3$, —$CH_2OCH_2CH_3$, —$CH_2OH$, —$CH_2SCH_3$, —$CF_2CH_2CH_3$, —$CH_2OCH_2OCH_3$, —$COCH_2CH_3$, —$C(CF_2)OCH_2CH_3$, —$CH(CF_3)OCH_2CH_3$, —$CH(CF_3)NHCH_2CH_3$,

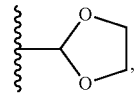

—CHO, —$CH_2CF_2CH_3$, —COSR, —$NR_1R_2$ and —$CH_2NR_1R_2$, wherein R is $C_1$-$C_4$ alkyl and each $R_1$ and $R_2$ are independently —H or —$C_1$-$C_4$ alkyl. In some embodiments, R' is selected from the group consisting of —$CHF_2$, —$CH_2CF_2CH_3$, —$CF_2CHF_2$, —$CF_2CF_2CH_3$, —$CF_2CH_2OCH_3$, —$CF_2OCH_2CH_3$, —$CF_2CH_2CH_3$, —$C(CF_2)OCH_2CH_3$, —$CH(CF_3)OCH_2CH_3$, —$CH(CF_3)NHCH_2CH_3$ and —$CH_2CF_2CH_3$. In some embodiments, R' is selected from the group consisting of

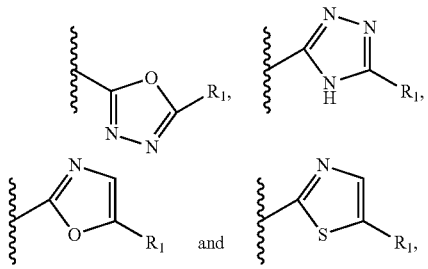

wherein each $R_1$ is independently selected from the group consisting of —$CH_3$, —$CH_2CH_3$ and —$CH(CH_3)_2$. In some embodiments, R' is selected from the group consisting of —COSR, —$NR_1R_2$ and —$CH_2NR_1R_2$, wherein R is —$C_1$-$C_4$ alkyl and $R_1$ and $R_2$ are independently —H or —$C_1$-$C_4$ alkyl.

Compounds may be of the following formula (III):

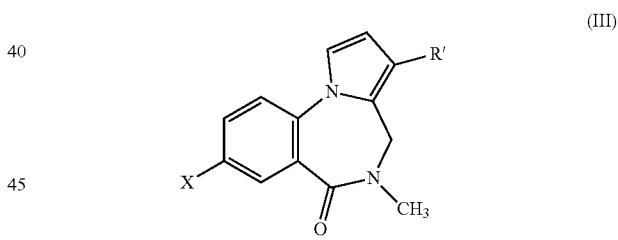

(III)

or a salt thereof, wherein:

X is Cl, Br, or F; and

R' is selected from the group consisting of —$CHF_2$, —$CH_2CF_2CH_3$, —$CF_2CHF_2$, —$CF_2CF_2CH_3$, —$CH_2OCH_3$, —$CF_2CH_2OCH_3$, —$CF_2OCH_2CH_3$, —$CH_2OCH_2CH_3$, —$CH_2OH$, —$CH_2SCH_3$, —$CF_2CH_2CH_3$, —$CH_2OCH_2OCH_3$, —$COCH_2CH_3$, —$C(CF_2)OCH_2CH_3$, —$CH(CF_3)OCH_2CH_3$, —$CH(CF_3)NHCH_2CH_3$,

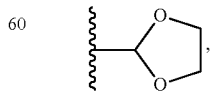

—CHO, —$CH_2CF_2CH_3$, —COSR, —$NR_1R_2$ and —$CH_2NR_1R_2$, wherein R is $C_1$-$C_4$ alkyl and each $R_1$ and $R_2$ are independently —H or —$C_1$-$C_4$ alkyl; or R' is selected from the group consisting of:

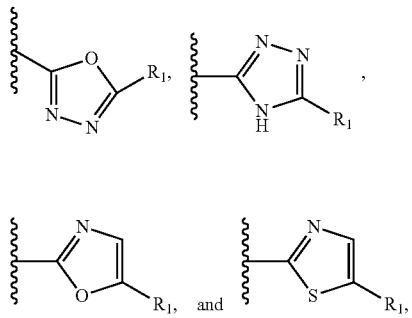

wherein each $R_1$ is independently selected from the group consisting of —$CH_3$, —$CH_2CH_3$ and —$CH(CH_3)_2$.

In some embodiments, X is F. In some embodiments, X is Cl. In some embodiments, X is Br. In some embodiments, R' is selected from the group consisting of —$CHF_2$, —$CH_2CF_2CH_3$, —$CF_2CHF_2$, —$CF_2CF_2CH_3$, —$CH_2OCH_3$, —$CF_2CH_2OCH_3$, —$CF_2OCH_2CH_3$, —$CH_2OCH_2CH_3$, —$CH_2OH$, —$CH_2SCH_3$, —$CF_2CH_2CH_3$, —$CH_2OCH_2OCH_3$, —$COCH_2CH_3$, —$C(CF_2)OCH_2CH_3$, —$CH(CF_3)OCH_2CH_3$, —$CH(CF_3)NHCH_2CH_3$,

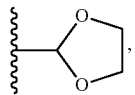

—CHO, —$CH_2CF_2CH_3$, —COSR, —$NR_1R_2$ and —$CH_2NR_1R_2$, wherein R is $C_1$-$C_4$ alkyl and each $R_1$ and $R_2$ are independently —H or —$C_1$-$C_4$ alkyl. In some embodiments, R' is selected from the group consisting of —$CHF_2$, —$CH_2CF_2CH_3$, —$CF_2CHF_2$, —$CF_2CF_2CH_3$, —$CF_2CH_2OCH_3$, —$CF_2OCH_2CH_3$, —$CF_2CH_2CH_3$, —$C(CF_2)OCH_2CH_3$, —$CH(CF_3)OCH_2CH_3$, —$CH(CF_3)NHCH_2CH_3$ and —$CH_2CF_2CH_3$. In some embodiments, R' is selected from the group consisting of

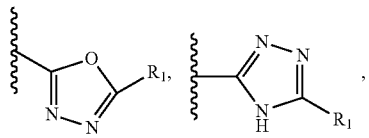

wherein each $R_1$ is independently selected from the group consisting of —$CH_3$, —$CH_2CH_3$ and —$CH(CH_3)_2$. In some embodiments, R' is selected from the group consisting of —COSR, —$NR_1R_2$ and —$CH_2NR_1R_2$, wherein R is —$C_1$-$C_4$ alkyl and $R_1$ and $R_2$ are independently —H or —$C_1$-$C_4$ alkyl.

Compounds may be of the following formula (IV):

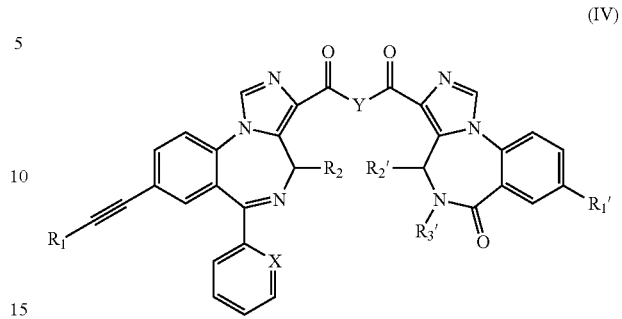

or a salt thereof, wherein:
Y is —$N(CH_2CH_2)_2N$—, —$S(CH_2)_nS$—, —$O(CH_2)_nO$—, or —$(CH_2)_n$— wherein each n is independently 3, 4 or 5;
X is CH, CF, CCl or N;
$R_1$ is —H or —$Si(Me)_3$;
$R_1$' is —H, —Cl, —Br, or —C≡C—R, where R is —H or —$Si(Me)_3$;
$R_2$ is —H, —$CF_3$ or —$CH_3$; and
$R_2$' and $R_3$' are independently —H or —$CH_3$, or $R_2$' and $R_3$' are taken together with the atoms to which they are attached to form a 5-, 6-, or 7-membered saturated ring.

In some embodiments, Y is —$O(CH_2)_nO$—. In some embodiments, X is CH. In some embodiments, X is N. In some embodiments, X is CF. In some embodiments, $R_1$ is —H. In some embodiments, $R_1$ is —$Si(Me)_3$. In some embodiments, $R_1$' is —Cl. In some embodiments, $R_1$' is —Br. In some embodiments, X is CH. In some embodiments, $R_2$ is —H. In some embodiments, $R_2$' is —H. In some embodiments, $R_3$' is —$CH_3$. In some embodiments, $R_2$' and $R_3$' are taken together with the atoms to which they are attached to form a 5-membered saturated ring.

Compounds may be of the following formula (V):

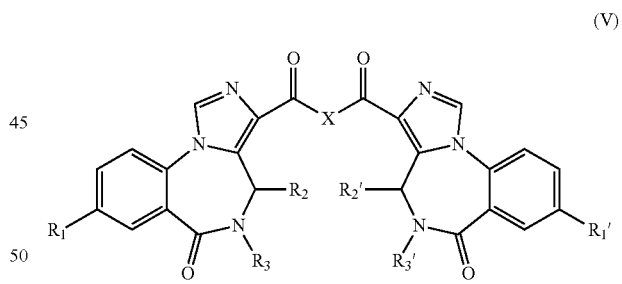

or a salt thereof, wherein:
X is —$N(CH_2CH_2)_2N$—, —$S(CH_2)_nS$—, or —$(CH_2)_n$— wherein each n is independently 3, 4 or 5;
$R_1$ and $R_1$' are independently —H, —Cl, —Br, or —C≡C—R, where R is —H or —$Si(Me)_3$;
$R_2$ and $R_3$ are independently —H or —$CH_3$, or $R_2$ and $R_3$ are taken together with the atoms to which they are attached to form a 5-, 6-, or 7-membered saturated ring;
$R_2$' and $R_3$' are independently —H or —$CH_3$, or $R_2$ and $R_3$ are taken together with the atoms to which they are attached to form a 5-, 6-, or 7-membered saturated ring.

In some embodiments, $R_1$ is —H. In some embodiments, $R_1$ is —Cl. In some embodiments, $R_1$ is —Br. In some embodiments, $R_1$' is —H. In some embodiments, $R_1$' is —Cl. In some embodiments, $R_1$' is —Br. In some embodiments, $R_2$ is —H. In some embodiments, R$_2$ is —CH$_3$. In some embodiments, R$_2$' is —H. In some embodiments, R$_2$' is —CH$_3$. In some embodiments, R$_3$ is —CH$_3$. In some embodiments, R$_3$' is —CH$_3$. In some embodiments, R$_2$ and R$_3$ are taken together with the atoms to which they are attached to form a 5-membered saturated ring. In some embodiments, R$_2$' and R$_3$' are taken together with the atoms to which they are attached to form a 5-membered saturated ring.

Compounds may be of the following formula (VI):

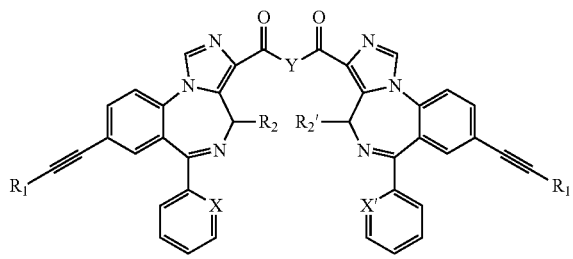

(VI)

or a salt thereof, wherein:

X and X' are independently CH, CF, CCl or N;

Y is —N(CH$_2$CH$_2$)$_2$N—, —S(CH$_2$)$_n$S—, —O(CH$_2$)$_n$O—, or —(CH$_2$)$_n$— wherein each n is independently 3, 4 or 5;

R$_1$ and R$_1$' are independently —H or —Si(Me)$_3$; and

R$_2$ and R$_2$' are independently —H or —CH$_3$.

In some embodiments, X is CH. In some embodiments, X is N. In some embodiments, X is CF. In some embodiments, X' is CH. In some embodiments, X' is N. In some embodiments, X' is CF. In some embodiments, Y is —O(CH$_2$)$_n$O—. In some embodiments, R$_1$ is —H. In some embodiments, R$_1$ is —Si(Me)$_3$. In some embodiments, R$_1$' is —H. In some embodiments, R$_1$' is —Si(Me)$_3$. In some embodiments, R$_2$ is —H. In some embodiments, R$_2$' is —H. In some embodiments, R$_2$ is —CH$_3$. In some embodiments, R$_2$' is —CH$_3$.

Compounds may also be of formula (Ia) or (Va) described below.

For compounds of formula (I), (II), (III), (IV), (V), (VI), (Ia) and (Va), groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

Compounds of formula (I), (II), (III), (IV), (V), (VI), (Ia) and (Va) include compounds that differ only in the presence of one or more isotopically enriched atoms. For example, compounds may have the present structures except for the replacement of hydrogen by deuterium or tritium, or the replacement of a carbon by a $^{13}$C- or $^{14}$C-enriched carbon.

A compound of (I), (II), (III), (IV), (V), (VI), (Ia) or (Va) can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present invention may also provide compounds of formula (I), (II), (III), (IV), (V), (VI), (Ia) and (Va) that are in a prodrug form. Prodrugs of the compounds are those compounds that readily undergo chemical changes under physiological conditions to provide the compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds of formula (I), (II), (III), (IV), (V), (VI), (Ia) and (Va) can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound of formula (I), (II), (III), (IV), (V) and (VI) may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compounds of formula (I), (II), (III), (IV), (V), (VI), (Ia) and (Va) may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound of formula (I), (II), (III), (IV), (V), (VI), (Ia) or (Va) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis of Compounds

Compounds of formula (I), (II), (III), (IV), (V), (VI), (Ia) and (Va) may be synthesized using commercially available starting materials. Exemplary syntheses are illustrated below.

Compounds of general formula 1 (X=CH, CF, N) have previously been synthesized (U.S. Pat. No. 7,119,196). Compound 1 can be hydrolyzed and converted into the acid chloride 2 as illustrated in Scheme 1. The acyl chloride 2 can then be reacted with the copper reagent (Corey et al. *Tetrahedron Lett.* 1983, 24, 3163-3164. Corey et al. *J. Am. Chem. Soc.* 1986, 108, 7114-7116) to provide ketone 3. This ketone can be converted into the difluoro analog 4 by treatment with (diethylamino)sulfur trifluoride (DAST) reagent (Bombrun et al. *J. Med. Chem.* 2003, 46, 4365-4368; International Patent Application Publication No. WO 2000/059503). This can then be converted into the acetyleno target ligand 5 on treatment with TBAF. An alternate route to 3 (via 6 and 7) is also represented in Scheme 1 (Venkatesan et al. *J. Med. Chem.* 2004, 47, 6556-6568; Normant et al. *Compt. Rend.* 1964, 259, 830-832; Castro et al. *Bulletin Soc. Chim. Fr.* 1967, 5, 1540-1547; Lehmann et al. *Tetrahedron Lett.* 1984, 25, 745-748. Oyama et al. *Tetrahedron Lett.* 2007, 48, 6005-6009; Noe et al. *Chem. Ber.* 1985, 118, 4453-4458).

Scheme 1.

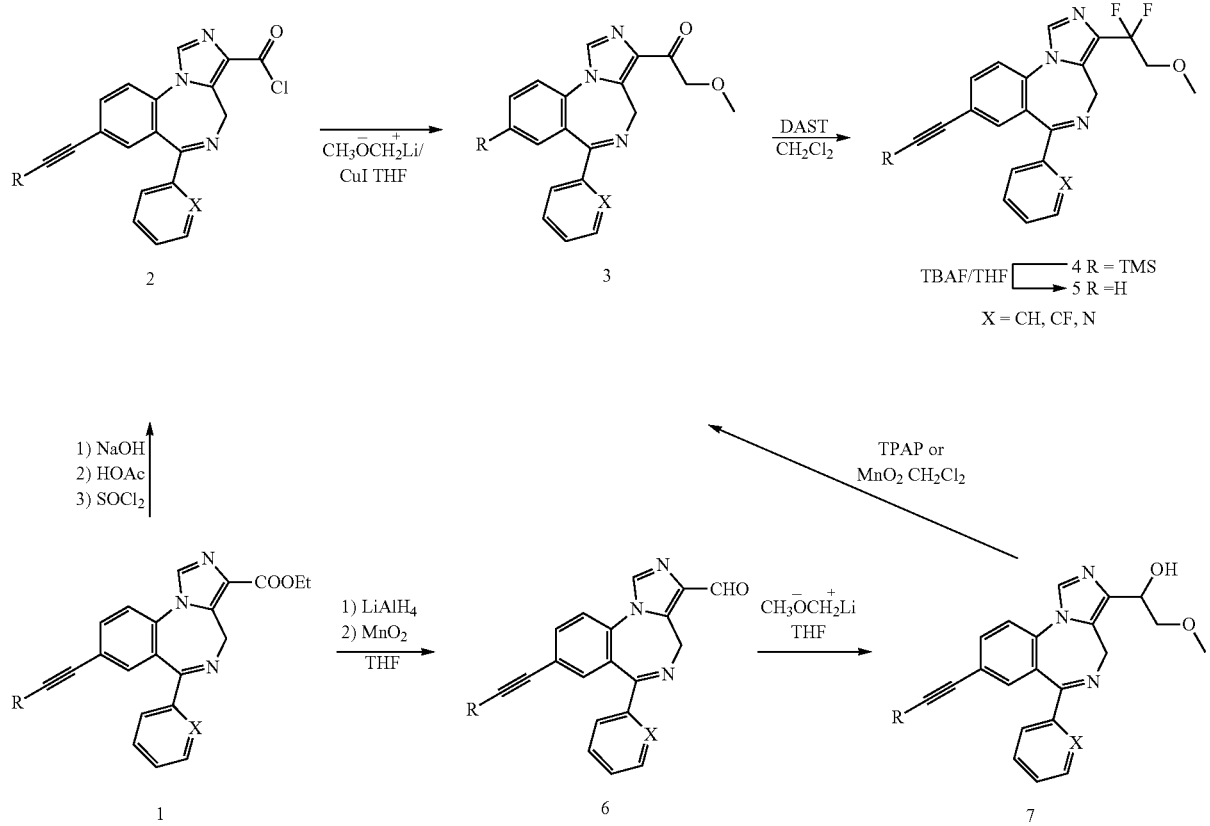

R = TMS
X = CH, CF, N

Scheme 2.

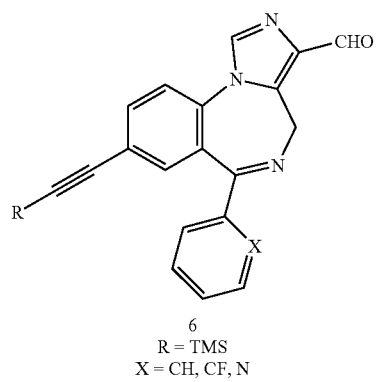

6
R = TMS
X = CH, CF, N

DAST
CH$_2$Cl$_2$

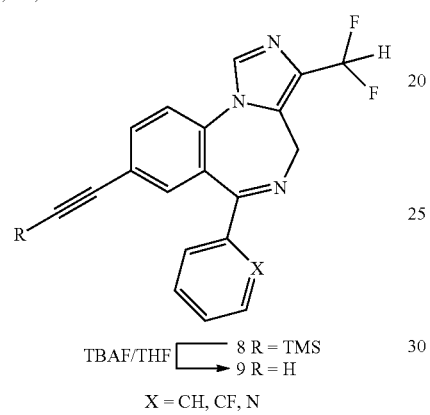

TBAF/THF  8 R = TMS
→ 9 R = H
X = CH, CF, N

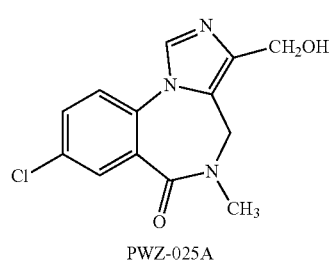

PWZ-025A

DAST, CH$_2$Cl$_2$
rt, 70%

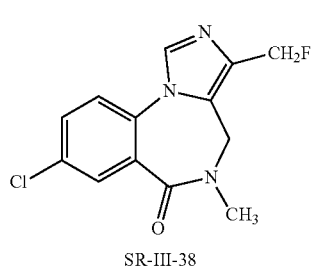

SR-III-38

Scheme 3.

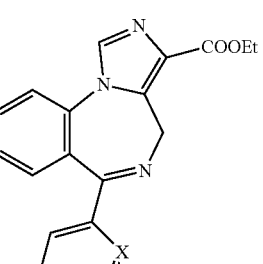

1
R = TMS
X = CH, CF, N

LiBH$_4$,
CH$_3$OH

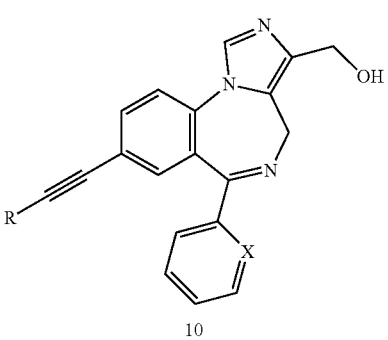

10

SOCl$_2$
THF

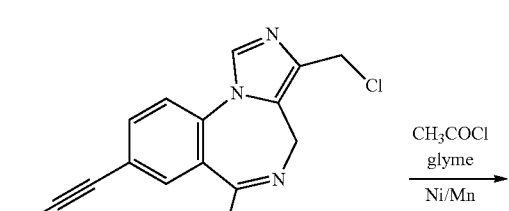

11

CH$_3$COCl
glyme
Ni/Mn

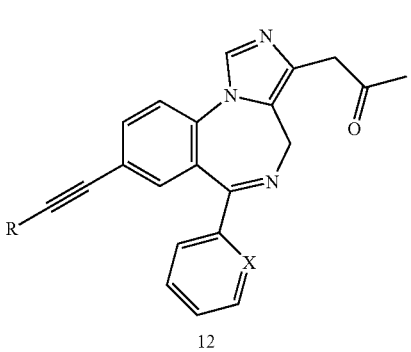

12

DAST,
CH$_2$Cl$_2$

The aldehyde 6 (see Scheme 1) can be converted into difluoro analog 8 by treatment with (diethylamino)sulfur trifluoride (DAST) reagent (Bombrun et al. *J. Med. Chem.* 2003, 46, 4365-4368; International Patent Application Publication No. WO 2000/059503). This can then be converted into the acetyleno target analog 9 on treatment with TBAF (Scheme 2). Similarly, PWZ-025A can be converted into difluoro analog SR-III-38 using the same literature procedure.

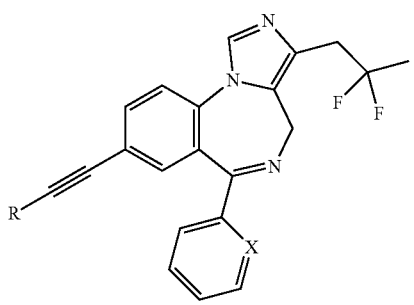

13 R = TMS
TBAF/THF → 14 R = H

X = CH, CF, N

Depicted in Scheme 3 is the route to acetyleno target 14. The starting ligand XHeII053 (1) can be reduced (U.S. Pat. No. 7,119,196) with LiBH₄ to provide the alcohol 10 which is converted into chloride 11 (Zhang et al. *J. Med. Chem.* 1995, 38, 1679-1688). Conversion of 11 into ketone 12 can be accomplished by treatment with acetyl chloride in the presence of nickel or manganese (Inaba et al. *Tetrahedron Lett.* 1983, 24, 2451-2452. Inaba et al. *J. Org. Chem.* 1985, 50, 1373-1381. Suh et al. *J. Organomet. Chem.* 2003, 684, 20-36). Treatment of ketone 12 with (diethylamino)sulfur trifluoride (DAST) will provide the difluoro analog 13 (Bombrun et al. *J. Med. Chem.* 2003, 46, 4365-4368; International Patent Application Publication No. WO 2000/059503). Treatment of 13 with TBAF provides the target 14.

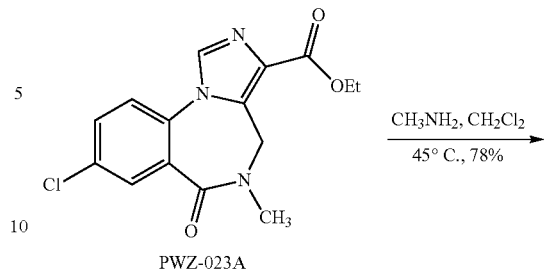

PWZ-023A

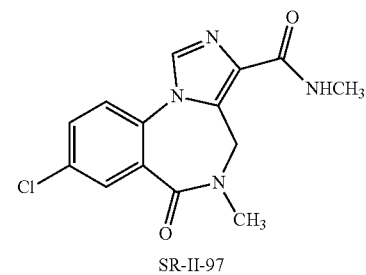

SR-II-97

Compounds of general structure 1 can be converted into the corresponding amides 15-17 following a literature procedure (Sanchez, I.; Pujol, M. D.; Guillaumet, G.; Massingham, R.; Monteil, A.; Dureng, G.; Winslow, E. Design and Synthesis of Substituted Compounds Containing the 1,4-Benzodioxin Subunit. New Potential Calcium Antagonists. *Eur. J. Med. Chem.* 2000, 35, 663-676). Similarly, PWZ-023A can be converted into the corresponding amide SR-II-97 using the same literature procedure.

Scheme 4.

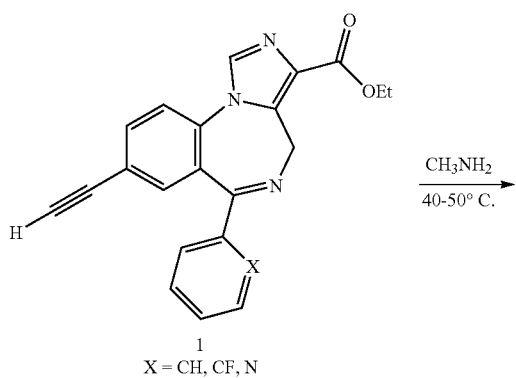

1
X = CH, CF, N

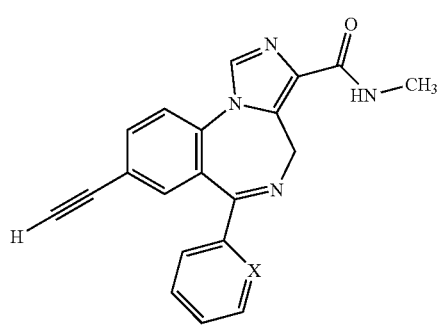

15 X = CH (YT-III-31)
16 X = CF (HJ-I-37)
17 X = N (HJ-I-40)

Scheme 5.

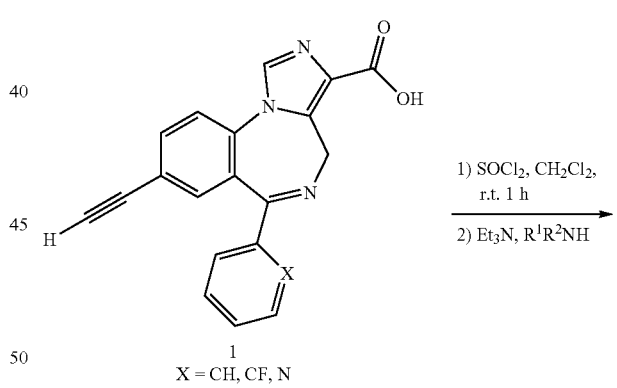

1
X = CH, CF, N

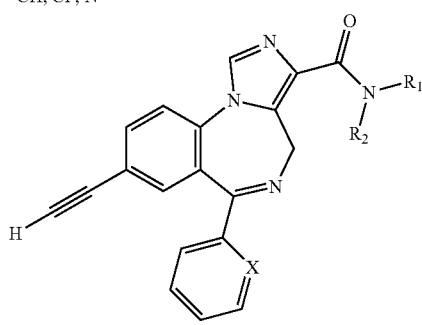

21
R₁ = R₂ = alkyl, X = CH, CF, N
X = N, R₁ = R₂ = Me, ZJW-II-61

25
-continued
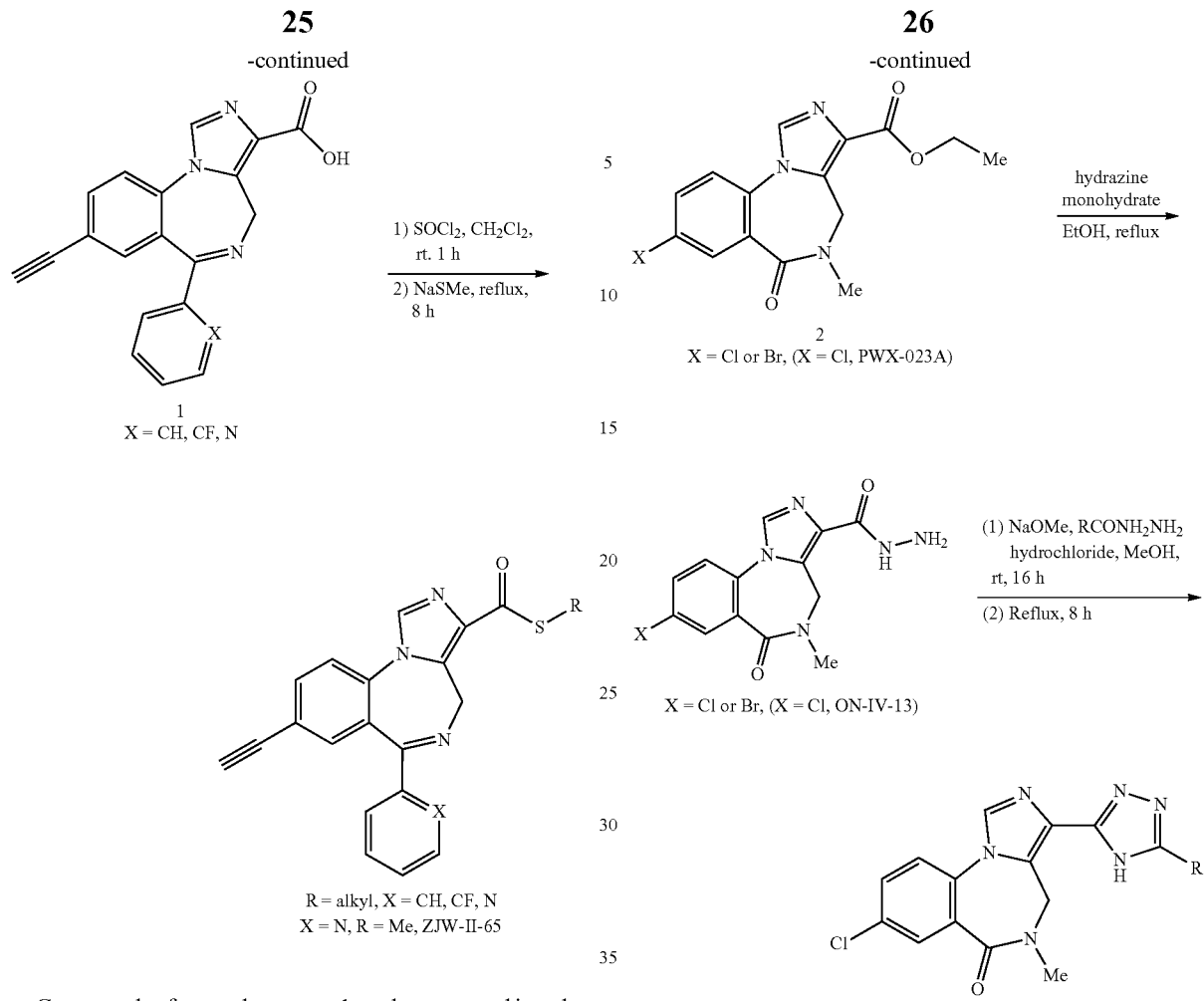
Compounds of general structure 1 can be converted into the corresponding amides and thiolates following a literature procedure (Feng et al. *Bioorg. Med. Chem.* 2008, 16, 8598-8606; Xu et al. *J. Agric. Food Chem.*, 2006, 54, 8793-8798).
26
-continued
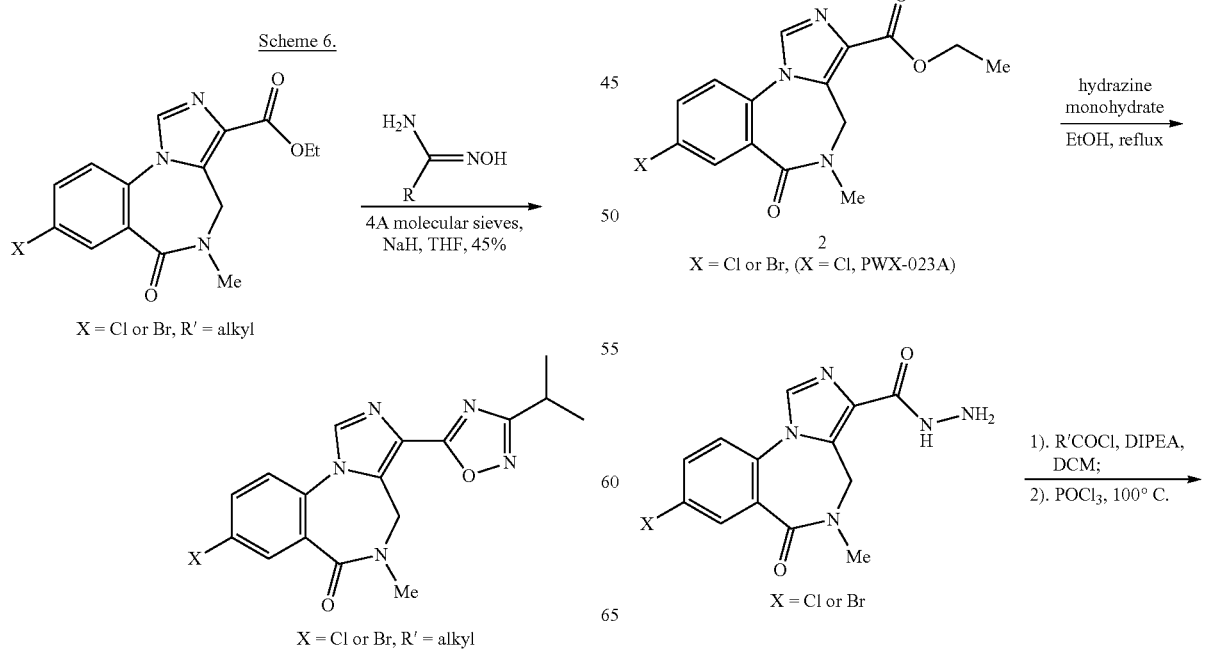

27

-continued

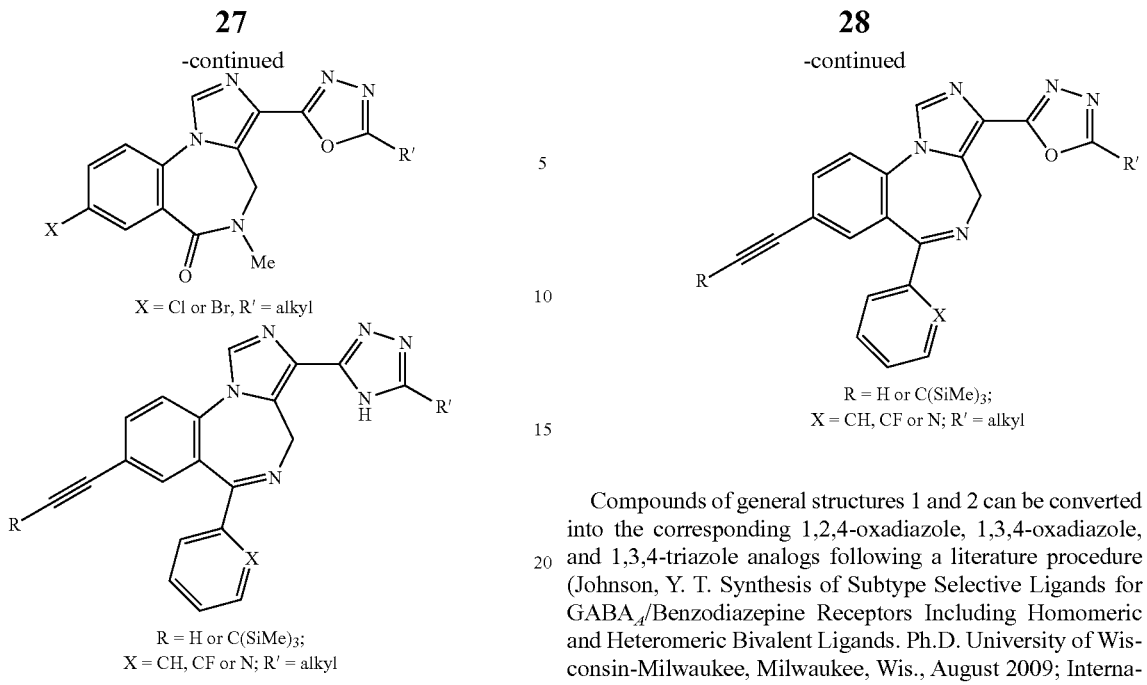

X = Cl or Br, R' = alkyl

R = H or C(SiMe)₃;
X = CH, CF or N; R' = alkyl

28

-continued

R = H or C(SiMe)₃;
X = CH, CF or N; R' = alkyl

Compounds of general structures 1 and 2 can be converted into the corresponding 1,2,4-oxadiazole, 1,3,4-oxadiazole, and 1,3,4-triazole analogs following a literature procedure (Johnson, Y. T. Synthesis of Subtype Selective Ligands for GABA$_A$/Benzodiazepine Receptors Including Homomeric and Heteromeric Bivalent Ligands. Ph.D. University of Wisconsin-Milwaukee, Milwaukee, Wis., August 2009; International Patent Application Publication No. WO 2010/046780).

Scheme 7.

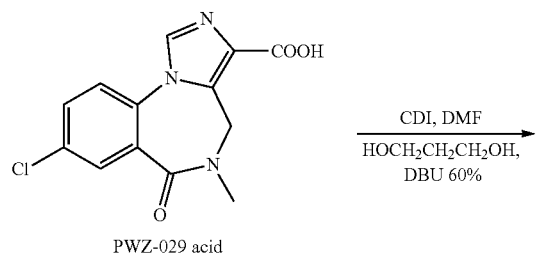

PWZ-029 acid

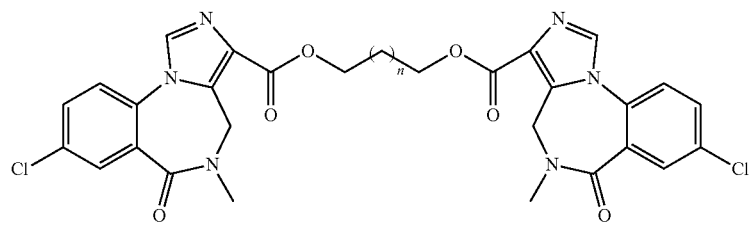

n = 1, YT-TC-1
n = 2, YT-TC-2
n = 3, YT-TC-3

YT-TC-4

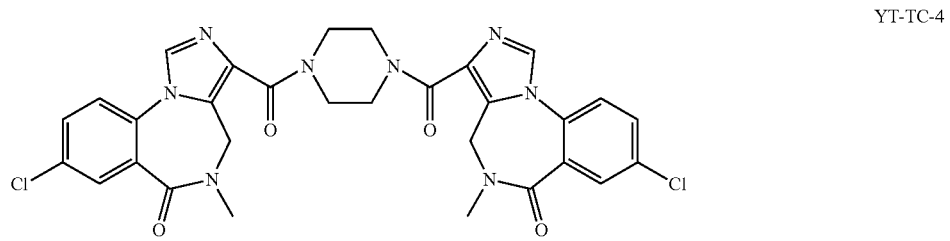

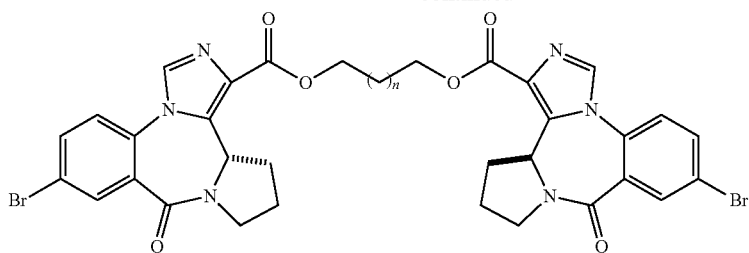
n = 1, YT-II-791
n = 2, YT-II-792
n = 3, YT-II-793
YT-III-274
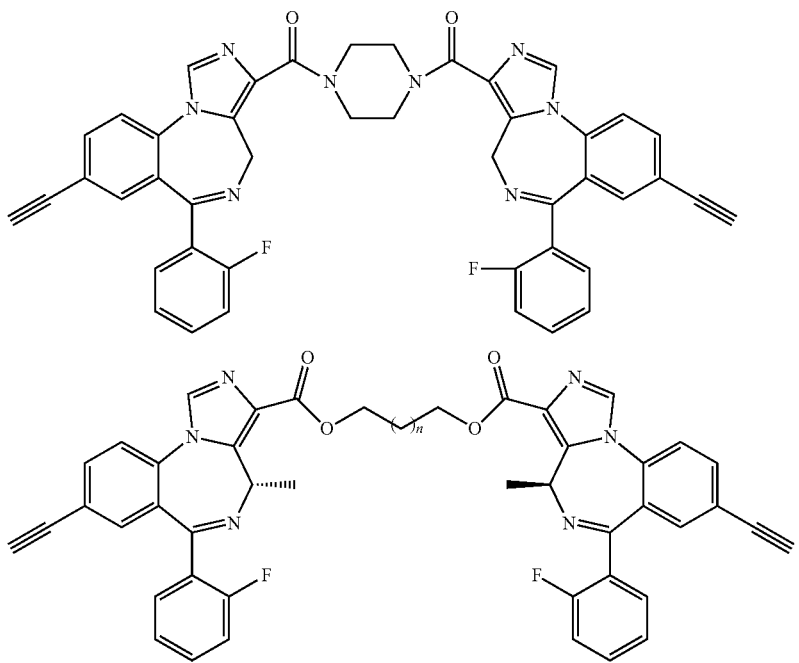
n = 1, YT-III-331
n = 2, YT-III-332
n = 3, YT-III-333
YT-III-30
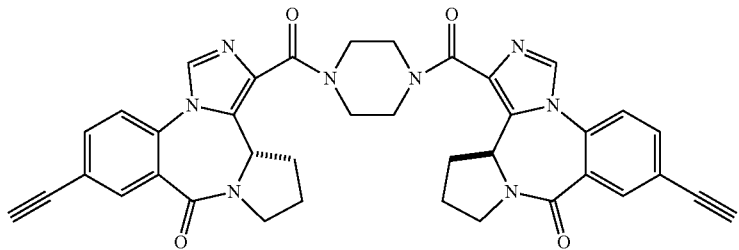
YT-III-334
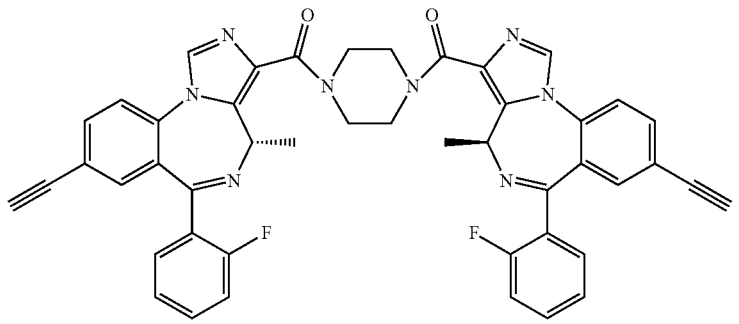

-continued
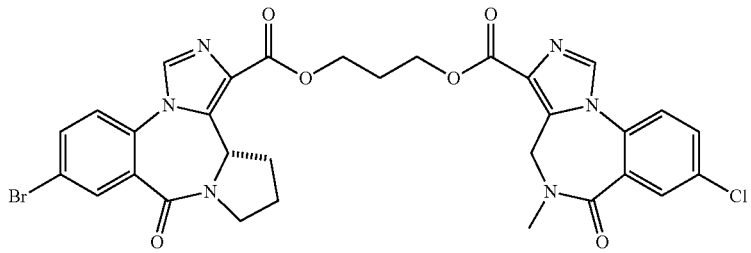
YT-III-10
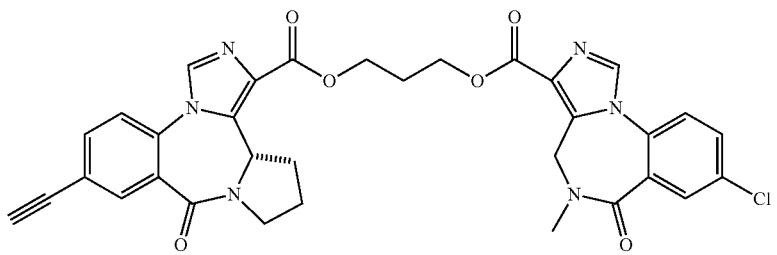
YT-III-28
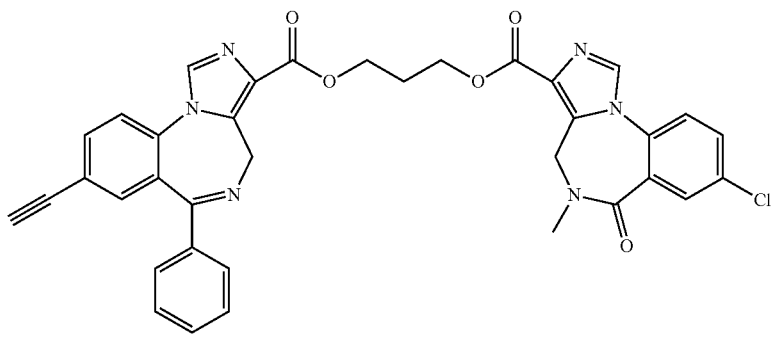
YT-III-15
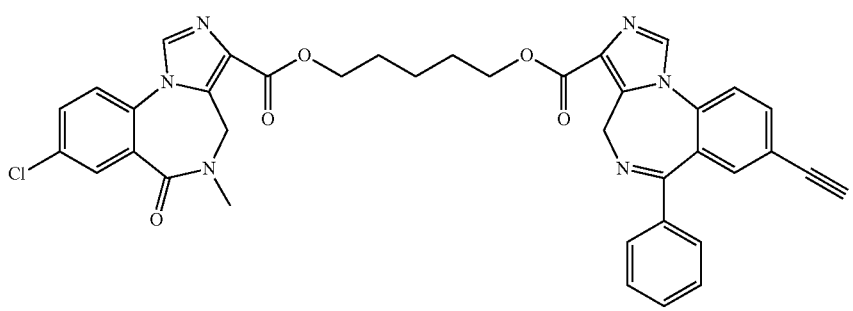
YT-III-341
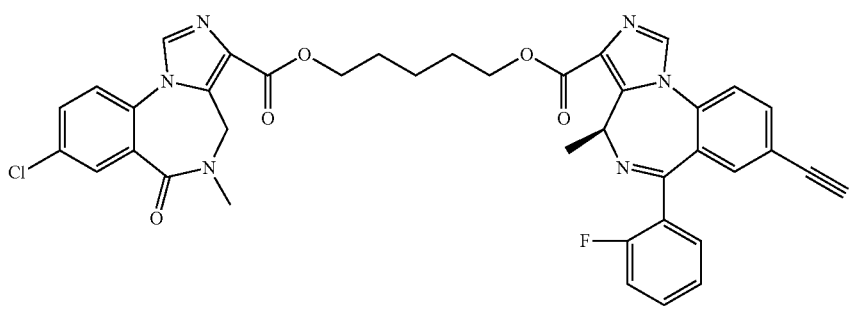
YT-III-33

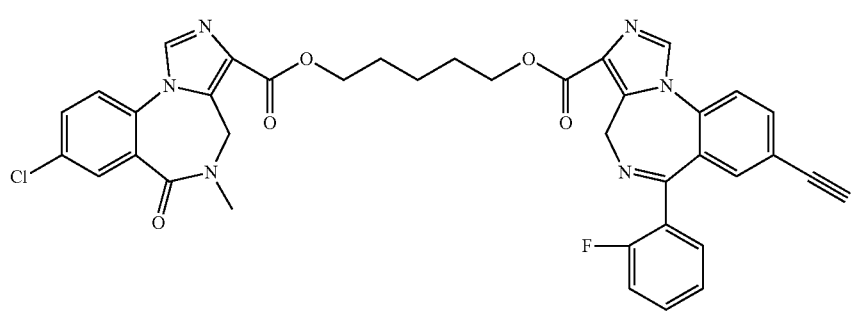
YT-III-342
PWZ-029 acid can be converted into the corresponding diesters YT-TC-1, YT-TC-2, and YT-TC-3 following a literature procedure (Li et al. *J. Med. Chem.* 2003, 46, 5567-5570). Similarly, other bivalent ligands shown in Scheme 7 can be synthesized using the same literature procedure.
Scheme 8.
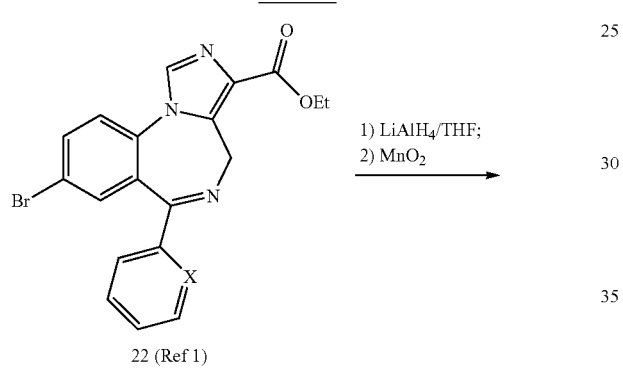
22 (Ref 1)
1) LiAlH₄/THF;
2) MnO₂
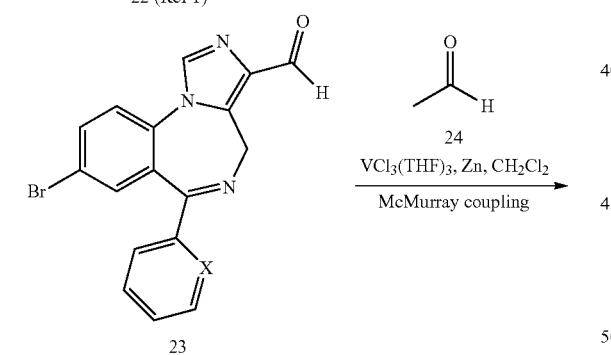
23
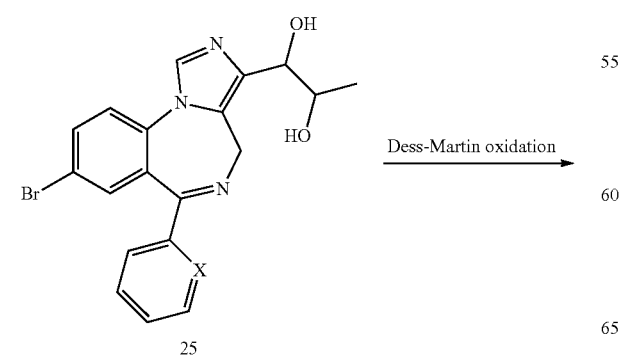
25
Dess-Martin oxidation
-continued
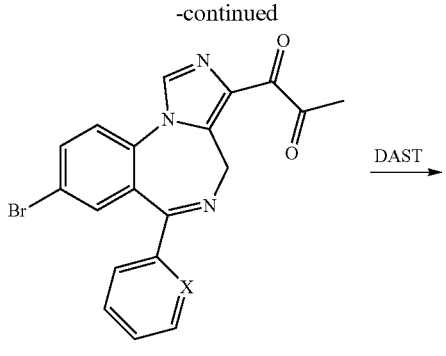
26
DAST
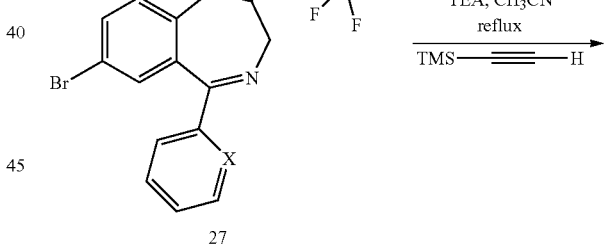
27
Pd(OAc)₂(PPh₃)₂
TEA, CH₃CN
reflux
TMS———H
28
TBAF·H₂O, THF -continued

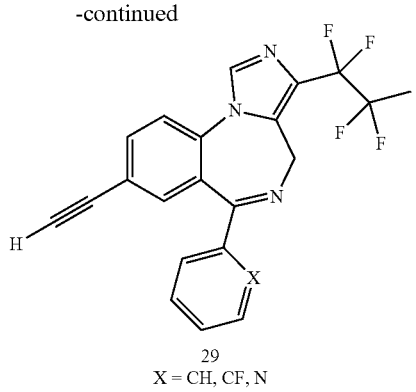

29
X = CH, CF, N

-continued

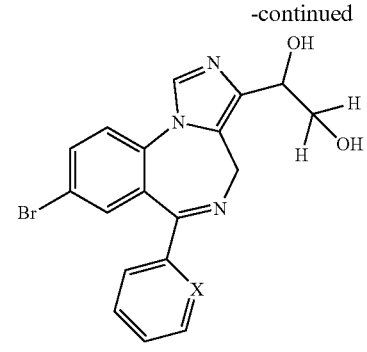

31

Dess-Martin oxidation, CH₂Cl₂ →

Outlined in Scheme 8 is the synthesis of benzodiazepines of general structure 29. Compounds of general formula 22 (X=CH, CF, N) have previously been synthesized (U.S. Pat. No. 7,119,196). Reduction of the ester moiety in 22 using LiAlH₄ followed by oxidation using MnO₂ (Venkatesan et al. *J. Med. Chem.* 2004, 47, 6556-6568) affords compounds of general structure 23. Intermolecular pinacol coupling of aldehyde 23 with acetaldehyde 24 under McMurry conditions (Han et al. *Bioorg. Med. Chem. Lett.* 2000, 10, 711-713) affords the diol 25. Dess-Martin oxidation (Id.) of diol 25 affords diketone 26. The tetrafluoro derivative 27 can be obtained from the reaction of diketone 5 using (diethylamino)sulfur trifluoride (DAST) in DCM at 0° C. (Bombrun et al. *J. Med. Chem.* 2003, 46, 4365-4368; International Patent Application Publication No. WO 2000/059503). Heck-type coupling of bromide 6 with trimethylsilylacetylene gives the trimethylsilyl analogues represented by 28. The silyl group is removed from 28 on treatment with fluoride anion to furnish 29.

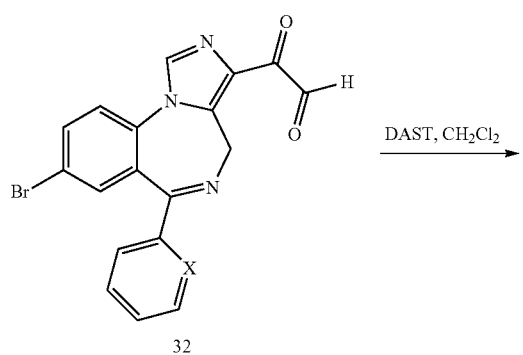

32

DAST, CH₂Cl₂ →

Scheme 9.

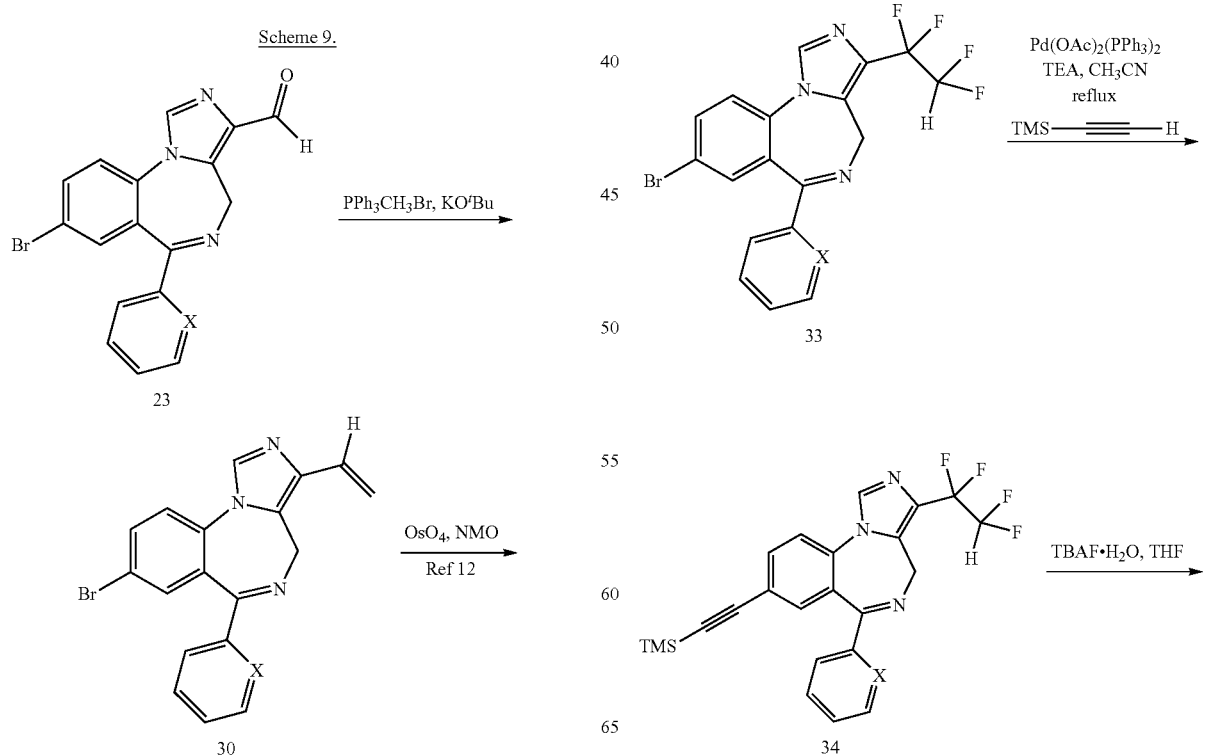

-continued

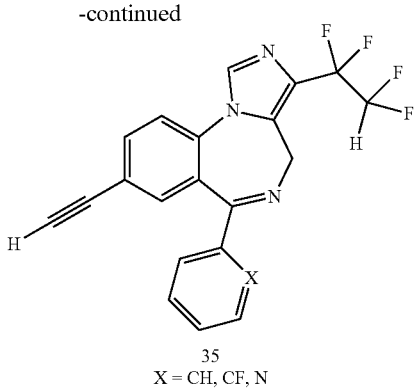

35
X = CH, CF, N

Outlined in Scheme 9 is the synthesis of benzodiazepines of general structure 35. Compounds of general formula 23 (X=CH, CF, N) have previously been synthesized (Scheme 5). Wittig olefination of aldehyde 23 affords the alkene 30 (Yin et al. *Org. Lett.* 2007, 9, 295-298). Dihydroxylation of olefin 30 using osmium tetroxide affords the diol 31 (Pearson et al. *J. Org. Chem.* 2004, 69, 9109-9122). Dess-Martin oxidation (Han et al. *Bioorg. Med. Chem. Lett.* 2000, 10, 711-713) of diol 31 affords ketoaldehyde 32. The tetrafluoro derivative 33 is obtained from the reaction of 32 using (diethylamino)sulfur trifluoride (DAST) in DCM at 0° C. (Bombrun et al. *J. Med. Chem.* 2003, 46, 4365-4368; International Patent Application Publication No. WO 2000/059503). Heck-type coupling of bromide 13 with trimethylsilylacetylene gives the trimethylsilyl analogues represented by 34. The silyl group is removed from 34 on treatment with fluoride anion to furnish 15.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Evaluation of Compounds

Compounds may be analyzed using a number of methods, including receptor binding studies and in vivo methods.

For example, the $GABA_A$ subunit selectivity of compounds can be evaluated, for example, using competitive binding assays. Such assays have been described (Choudhary et al. *Mol. Pharmacol.* 1992, 42, 627-33; Savić et al. *Progress in Neuro-Psychopharmacology & Biological Psychiatry*, 2010, 34, 376-386). The assays involve the use of a radiolabeled compound known to bind to $GABA_A$ receptors, such as [$^3$H] flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, Calif.).

Compounds can also be evaluated in electrophysiological assays in *Xenopus oocytes*. Compounds can be preapplied to the oocytes before the addition of GABA, which can then be coapplied with the compounds until a peak response is observed. Between applications, oocytes can be washed to ensure full recovery from desensitization. For current measurements, the oocytes can be impaled with microelectrodes, and recordings performed using voltage clamps.

Compounds described herein may be $GABA_A$ receptor ligands which exhibit anxiolytic activity due to increased agonist efficacy at $GABA_A/\alpha 2$, $GABA_A/\alpha 3$ and/or $GABA_A/\alpha 5$ receptors. The compounds may possess at least 2-fold, suitably at least 5-fold, and advantageously at least a 10-fold, selective efficacy for the $GABA_A/\alpha 2$, $GABA_A/\alpha 3$, and/or $GABA_A/\alpha 5$ receptors relative to the $GABA_A/\alpha 1$ receptors. However, compounds which are not selective in terms of their agonist efficacy for the $GABA_A/\alpha 2$, $GABA_A/\alpha 3$, and/or $GABA_A/\alpha 5$ receptors are also encompassed within the scope of the present invention. Such compounds will desirably exhibit functional selectivity by demonstrating anxiolytic activity with decreased sedative-hypnotic/muscle relaxant/ataxic activity due to decreased efficacy at $GABA_A/\alpha 1$ receptors.

GABAergic receptor subtype selective compounds which are ligands of the $GABA_A$ receptors acting as agonists or partial agonists are referred to hereinafter as "$GABA_A$ receptor agonists" or "$GABA_A$ receptor partial agonists" or "agonists" or "partial agonists". In particular these are compounds that are ligands of the benzodiazepine (BZ) binding site of the $GABA_A$ receptors, and hence acting as BZ site agonists or partial agonists. Such ligands also include compounds acting at the GABA site or at modulatory sites other than the benzodiazepine site of $GABA_A$ receptors.

GABAergic receptor subtype selective compounds act preferably by selectively or preferentially activating as agonists or partial agonists the $GABA_A/\alpha_2$ receptors and/or $GABA_A/\alpha_3$ receptors as compared to the $GABA_A/\alpha_1$ receptors. A selective or preferential therapeutic agent has less binding affinity or efficacy to the $GABA_A/\alpha_1$ receptors compared to the $GABA_A/\alpha_2$ or $GABA_A/\alpha_3$ receptors. Alternatively, the agent binds to $GABA_A/\alpha_1$, $GABA_A/\alpha_2$ and $GABA_A/\alpha_3$ receptors with a comparable affinity but exerts preferential efficacy of receptor activation at $GABA_A/\alpha_2$ and $GABA_A/\alpha_3$ receptors compared to the $GABA_A/\alpha_1$ receptors. A selective agent of the present invention can also have a greater or lesser ability to bind or to activate $GABA_A/\alpha_5$ receptors relative to $GABA_A/\alpha_2$ and $GABA_A/\alpha_3$ receptors. The anticonvulsant agent acts at the benzodiazepine site of the respective $GABA_A$ receptors but is not restricted to this drug binding domain in its receptor interactions.

Other methods for evaluating compounds are known to those skilled in the art. For example, an assessment of anxiolytic effects of compounds can be accomplished objectively and quantitatively with operant-based conflict procedures, as described in Fischer et al. *Neuropharmacology* 59 (2010) 612-618. Briefly, behavior which is positively reinforced can be suppressed in these procedures by response-contingent administration of a noxious stimulus such as mild electric shock. If a compound has an anxiolytic effect it increases the rates of responding that are normally suppressed by response-contingent delivery of shock. The strength of conflict procedures is their predictive validity with respect to expected therapeutic effects in humans. Results from the Fischer et al. indicate that benzodiazepine-like drugs that have pharmacological activity for $\alpha 2 GABA_A$ and/or $\alpha 3 GABA_A$ receptors and low receptor activity at $\alpha 1 GABA_A$ and $\alpha 5 GABA_A$ receptors may be useful, particularly as non-sedating anxiolytics.

Anxiolytic activity and locomotor activity can evaluated in the light/dark box by a method developed by Crawley (*Neu-* rosci Biobehav Rev 1985, 9, 37-44). The light/dark box is an extremely simple noninvasive test for anxiolytic activity. Mice or rats are administered new agents 15-30 minutes prior to testing and placed in the dark portion of the light/dark box. The amount of time it takes the animals to enter the light side and how long they stay versus controls (e.g., diazepam) are a measure of anxiolytic activity. The amount of exploration (or lack thereof) can be used as a preliminary measure of sedation.

In the elevated plus maze (Savic et al. *Pharmacol Biochem Behav* 2004, 79, 279-290), test compounds can be administrated ip 15 minutes prior to testing at which time mice can be placed in the center of the maze under a bright light condition. The number of crosses as well as the time spent in the open and closed arms of the maze for the following 15 minutes can be recorded. Control values for the percentage of entries into the open arms, percentage of time spent in the open arms, and total entries can be correlated to values obtained with controls (e.g., diazepam). Promising compounds may not suppress locomotor activity at up to 100 mg/kg and may be anxiolytic.

For evaluation of potential to treat schizophrenia, compounds may be tested using a mouse model as described in Gill et al. *Neuropsychopharmacology* 2011, 36: 1903-1911. This mouse model of schizophrenia arises from a development disturbance induced by the administration of a DNA-methylating agent, methylazoxymethanol acetate (MAM), to pregnant dams on gestational day 17. The MAM-treated offspring display structural and behavioral abnormalities, consistent with those observed in human patients with schizophrenia. Antagonism or genetic deletion of the $\alpha 5 GABA_A$ receptor ($\alpha 5 GABA_A$ R) leads to behaviors that resemble some of the behavioral abnormalities seen in schizophrenia, including prepulse inhibition to startle and impaired latent inhibition. The MAM model can be used to show the effectiveness of a benzodiazepine-positive allosteric modulator (PAM) compound selective for the $\alpha 5$ subunit of the $GABA_A R$. In Gill et al., the pathological increase in tonic dopamine transmission in the brain was reversed, and behavioral sensitivity to psychostimulants observed in MAM rats was reduced. The data suggests that such compounds would be effective in alleviating dopamine-mediated psychosis.

Compounds selective for $GABA_A$ receptor subunits can be tested for the ability to suppress seizures in several standard rat and mouse models of epilepsy, as described in U.S. Patent Application Publication No. US 2011/0261711. Anticonvulsant activity of compounds can be compared to diazepam. The standard models incorporated into anticonvulsant screening include the maximal electroshock test (MES), the subcutaneous Metrazol test (scMet), and evaluations of toxicity (TOX). The data for each condition can be presented as a ratio of either the number of animals protected or toxic (loss of locomotor activity) over the number of animals tested at a given time point and dose.

The MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on MES convulsions, 60 Hz of alternating current (50 mA in mice, 150 in rats) is delivered for by corneal electrodes which have been primed with an electrolyte solution containing an anesthetic agent (0.5% tetracaine HCL). For Test 1, mice are tested at various intervals following doses of 30, 100 and 300 mg/kg of test compound given by ip injection of a volume of 0.01 mL/g. In Test 2, rats are tested after a dose of 30 mg/kg (po) in a volume of 0.04 mL/g. Test 8 uses varying doses administered via i.p. injection, again in a volume of 0.04 ml/g. An animal is considered "protected" from MES-induced seizures upon abolition of the hindlimb tonic extensor component of the seizure (Swinyard, E. A., et al. in Antiepileptic Drugs, Levy, R. H. M., et al., Eds.; Raven Press: New York, 1989; pp 85-102; White, H. S., et al., *Ital J Neurol Sci*. 1995a, 16, 73-7; White, H. S., et al., in Antiepileptic Drugs, Levy, R. H. M., Meldrum, B. S., Eds.; Raven Press: New York, pp 99-110, 1995b).

Subcutaneous injection of the convulsant Metrazol produces clonic seizures in laboratory animals. The scMet test detects the ability of a test compound to raise the seizure threshold of an animal and thus protect it from exhibiting a clonic seizure. Animals can pretreated with various doses of the test compound (in a similar manner to the MES test, although a dose of 50 mg/kg (po) is the standard for Test 2 scMet). At the previously determined TPE of the test compound, the dose of Metrazol which will induce convulsions in 97% of animals (CD.sub.97: 85 mg/kg mice) is injected into a loose fold of skin in the midline of the neck. The animals can be placed in isolation cages to minimize stress (Swinyard et al. *J. Physiol*. 1961, 132, 97-0.102) and observed for the next 30 minutes for the presence or absence of a seizure. An episode of clonic spasms, approximately 3-5 seconds, of the fore and/or hindlimbs, jaws, or vibrissae is taken as the endpoint. Animals which do not meet this criterion are considered protected.

To assess a compound's undesirable side effects (toxicity), animals may monitored for overt signs of impaired neurological or muscular function. In mice, the rotorod procedure (Dunham, M. S. et al. *J. Amer. Pharm. Ass. Sci. Ed*. 1957, 46, 208-209) is used to disclose minimal muscular or neurological impairment. When a mouse is placed on a rod that rotates at a speed of 6 rpm, the animal can maintain its equilibrium for long periods of time. The animal is considered toxic if it falls off this rotating rod three times during a 1-min period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

To further characterize the anticonvulsant activity of compounds, a hippocampus kindling screen can be performed. This screen is a useful adjunct to the traditional MES and scMet tests for identification of a substance potential utility for treating complex partial seizures.

Benzodiazepines can be highly effective drugs in certain treatment paradigms. They are routinely employed for emergency situations such as status epilepticus and other acute conditions. But their use in chronic convulsant diseases has been limited due to side effects such as sedation and with high doses respiratory depression, hypotension and other effects. Further it has long been purported that chronic administration of this class of drugs can lead to tolerance to the anticonvulsant effects. This has limited their utility as first line treatment for chronic anticonvulsant conditions. Discovery of a potent BDZ with a decreased side effect profile and efficacy over extended treatment periods would be highly desirable.

In order to assess the effects of tolerance of compounds, whether tolerance could be detected using a chronic (5 day) dose of the candidate drug can be studied. With typical benzodiazepines (for example diazepam), tolerance to the anticonvulsant effects of the drug are evident before 5 days have passed, consequently studies can be done for only 5 days. The dose to be used may be the predetermined $ED_{50}$ against the scMet seizure model.

Compositions and Routes of Administration

In another aspect, the invention provides pharmaceutical compositions comprising one or more compounds of this invention in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective $GABA_A$ receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Treatment

Compounds may be used in methods of treatment or prevention of anxiety disorders, epilepsy and/or schizophrenia.

Epilepsy is a common chronic neurological disorder that is characterized by recurrent unprovoked seizures. These seizures are transient signs and/or symptoms due to abnormal, excessive or synchronous neuronal activity in the brain. There are many different epilepsy syndromes, each presenting with its own unique combination of seizure type, typical age of onset, EEG findings, treatment, and prognosis. Exemplary epilepsy syndromes include, e.g., Benign centrotemporal lobe epilepsy of childhood, Benign occipital epilepsy of childhood (BOEC), Autosomal dominant nocturnal frontal lobe epilepsy (ADNFLE), Primary reading epilepsy, Childhood absence epilepsy (CEA), Juvenile absence epilepsy, Juvenile myoclonic epilepsy (JME), Symptomatic localization-related epilepsies, Temporal lobe epilepsy (TLE), Frontal lobe epilepsy, Rasmussen's encephalitis, West syndrome, Dravet's syndrome, Progressive myoclonic epilepsies, and Lennox-Gastaut syndrome (LGS). Genetic, congenital, and developmental conditions are often associated with epilepsy among younger patients. Tumors might be a cause for patients over age 40. Head trauma and central nervous system infections may cause epilepsy at any age.

Schizophrenia is a mental disorder characterized by a breakdown of thought processes and by poor emotional responsiveness. It most commonly manifests itself as auditory hallucinations, paranoid or bizarre delusions, or disorganized speech and thinking, and it is accompanied by significant social or occupational dysfunction. The onset of symptoms typically occurs in young adulthood, with a global lifetime prevalence of about 0.3-0.7%. Diagnosis is based on observed behavior and the patient's reported experiences. Genetics, early environment, neurobiology, and psychological and social processes appear to be important contributory factors. Current research is focused on the role of neurobiology, although no single isolated organic cause has been found. Particular types of schizophrenia include paranoid type, disorganized type, catatonic type, undifferentiated type, residual type, post-schizophrenic depression and simple schizophrenia.

Anxiety disorder is a term covering several different forms of a type of mental illness of abnormal and pathological fear and anxiety. Current psychiatric diagnostic criteria recognize a wide variety of anxiety disorders. Recent surveys have found that as many as 18% of Americans may be affected by one or more of them. The term anxiety covers four aspects of experiences an individual may have: mental apprehension, physical tension, physical symptoms and dissociative anxiety. Anxiety disorder is divided into generalized anxiety disorder, phobic disorder, and panic disorder; each has its own characteristics and symptoms and they require different treatment. The emotions present in anxiety disorders range from simple nervousness to bouts of terror. Standardized screening clinical questionnaires such as the Taylor Manifest Anxiety Scale or the Zung Self-Rating Anxiety Scale can be used to detect anxiety symptoms, and suggest the need for a formal diagnostic assessment of anxiety disorder.

Particular examples of anxiety disorders include generalized anxiety disorder, panic disorder, phobias such as agoraphobia, social anxiety disorder, obsessive-compulsive disorder, post-traumatic stress disorder, separation anxiety and childhood anxiety disorders.

In another aspect, the invention provides a method of treating a disorder selected from an anxiety disorder, epilepsy and schizophrenia in a subject in need of treatment, comprising administering to the subject an effective amount of a compound of formula (Ia):

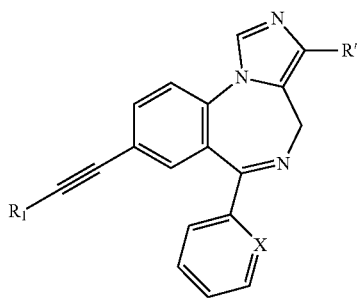

(Ia)

or a salt thereof, wherein:

R is —H or —Si(Me)$_3$;

X is CH, CF, CCl or N; and

R' is selected from the group consisting of —CHF$_2$, —CH$_2$CF$_2$CH$_3$, —CF$_2$CHF$_2$, —CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$, —CH$_2$OCH$_2$OCH$_3$, —COCH$_2$CH$_3$, —C(CF$_2$)OCH$_2$CH$_3$, —CH(CF$_3$)OCH$_2$CH$_3$, —CH(CF$_3$)NHCH$_2$CH$_3$,

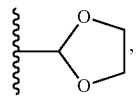

—CHO, —CH$_2$CF$_2$CH$_3$, COSR, or CONR$_1$R$_2$, wherein R, R$_1$ and R$_2$ are each independently H or C$_1$-C$_4$ alkyl, or R' is selected from the group consisting of:

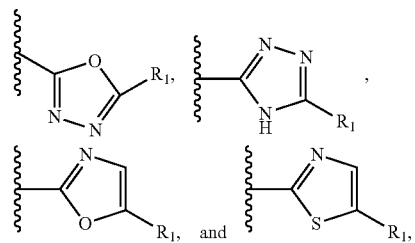

wherein each R$_1$ is independently selected from the group consisting of CH$_3$, CH$_2$CH$_3$ and CH(CH$_3$)$_2$.

In another aspect, the invention provides a method of treating a disorder selected from an anxiety disorder, epilepsy and schizophrenia in a subject in need of treatment, comprising administering to the subject an effective amount of a compound of formula (Va):

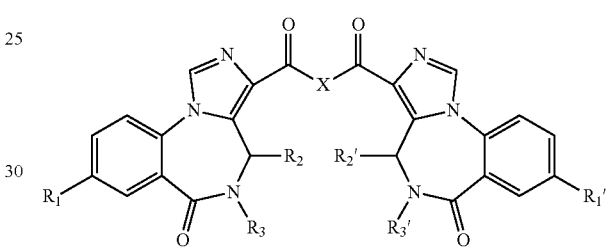

(Va)

or a salt thereof, wherein:

X is —N(CH$_2$CH$_2$)$_2$N—, —S(CH$_2$)$_n$S—, —O(CH$_2$)$_n$O—, or —(CH$_2$)$_n$— wherein each n is independently 3, 4 or 5;

R$_1$ and R$_1$' are independently —H, —Cl, —Br, or —C≡C—R, where R is —H or —Si(Me)$_3$;

R$_2$ and R$_3$ are independently —H or —CH$_3$, or R$_2$ and R$_3$ are taken together with the atoms to which they are attached to form a 5-, 6-, or 7-membered saturated ring;

R$_2$' and R$_3$' are independently —H or —CH$_3$, or R$_2$ and R$_3$ are taken together with the atoms to which they are attached to form a 5-, 6-, or 7-membered saturated ring.

In an aspect, the invention provides a method of treating an anxiety disorder in a subject in need of treatment, comprising administering to the subject an effective amount of a compound of formula (I), (II), (III), (IV), (V) or (VI), (Ia) or (Va). In embodiments, the anxiety disorder is selected from the group consisting of generalized anxiety disorder, panic disorder, phobias such as agoraphobia, social anxiety disorder, obsessive-compulsive disorder, post-traumatic stress disorder, separation anxiety and childhood anxiety disorders.

In an aspect, the invention provides a method of treating schizophrenia in a subject in need of treatment, comprising administering to the subject an effective amount of a compound of formula (I), (II), (III), (IV), (V) or (VI), (Ia) or (Va). In embodiments, the schizophrenia may be selected from the group consisting of paranoid type, disorganized type, catatonic type, undifferentiated type, residual type, post-schizophrenic depression and simple schizophrenia.

In an aspect, the invention provides a method of treating epilepsy in a subject in need of treatment, comprising administering to the subject an effective amount of a compound of formula (I), (II), (III), (IV), (V) or (VI), (Ia) or (Va). In another aspect, the invention provides a method of treating seizures in a subject in need of treatment, comprising administering to the subject an effective amount of a compound of formula (I), (II), (III), (IV), (V) or (VI), (Ia) or (Va).

The following non-limiting examples are intended to be purely illustrative of some aspects and embodiments, and show specific experiments that were carried out in accordance with the disclosure.

EXAMPLES

Explanation of Terms

EC3: A concentration of GABA eliciting 3% of the maximal GABA-elicited current amplitude of the individual oocyte.

log [M]: Represents the logarithm of molar concentration

Example 1

Synthesis of 8-chloro-3-(fluoromethyl)-5-methyl-4H-benzo[f]imidazo[1,5-a][1,4]diazepin-6(5H)-one (SR-III-38)

The alcohol PWZ-025A (100 mg, 0.360 mmol) was dissolved in anhydrous $CH_2Cl_2$ (5 mL). At 0° C. diethylaminosulfur trifluoride (0.07 mL, 0.720 mmol) was added very slowly and the reaction was allowed to stir for 2 hr. The reaction mixture was then quenched with aqueous solution of $NaHCO_3$ and stirred for 1 hr and extracted with $CH_2Cl_2$. The combined organic layers were washed with brine and dried over $MgSO_4$. After removal of solvent under reduced pressure, the residue was purified by a wash column on silica gel (gradient elution 80-20% EtOAc:Hexane) to afford the product SR-III-38 (0.070 mg, 70%). $^1H$ NMR ($CDCl_3$, 300 MHz) δ 8.06 (dd, 1H, J=1.33), 7.89 (s, 1H), 7.60 (dd, 1H, $J_1$=8.57 Hz, $J_2$=1.23 Hz)), 7.37 (dd, 1H, $J_1$=8.57 Hz, $J_2$=1.23 Hz), 5.58 (s, 1H), 5.41 (S, 1H), 4.40 (br, 2H), 3.25 (s, 3H): $^{19}F$ NMR ($CDCl_3$, 282 MHz) δ −205.21 (t, J=18 Hz, 1F), (MS (EI) m/e 279 (M+, 100). Anal. Calcd. For $C_{13}H_{11}ClFN_3O$. 0.13 ($C_2H_5$)$_2O$; C, 56.11; H, 4.28; N, 14.54. Found 55.86; H, 3.97; N, 14.17.

Example 2

Synthesis of Amides 15-17

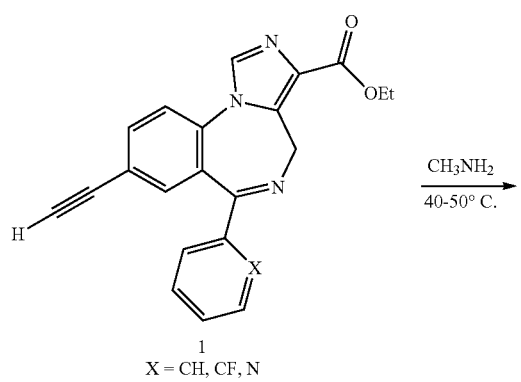

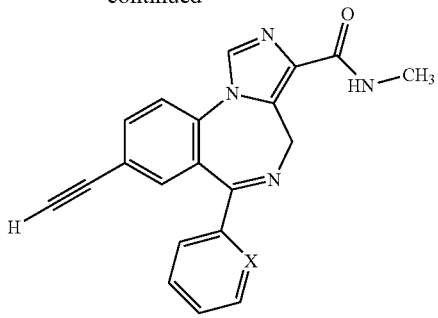

15 X = CH (YT-III-31)
16 X = CF (HJ-I-37)
17 X = N (HJ-I-40)

General Procedure for the Synthesis of Amide Derivatives 15-17

Compound 1 (1 mmol) and methylamine (33% wt solution in ethanol, 2 mL) were dissolved in $CH_2Cl_2$ (2 mL). The resulting suspension was stirred at 45-50° C. for 24 h during which time it became a clear solution. After removing the solvent and methylamine under reduced pressure, the residue was purified by a wash column (silica gel, plain $CH_2Cl_2$-0.5% MeOH in $CH_2Cl_2$) to afford compounds 15-17 as white powders.

8-Ethynyl-N-methyl-6-phenyl-4H-benzo[f]imidazo [1,5-a][1,4]diazepine-3-carboxamide (15)

Compound 15 (YT-III-31) was prepared in 90% yield from 1 using the procedure described above. 15: mp: 237-238° C.; $^1H$ NMR ($CDCl_3$) δ 2.97-2.99 (d, 3H, J=5.04 Hz), 3.17 (s, 1H), 4.05-4.09 (d, 1H, J=12.09 Hz), 6.26-6.29 (d, 1H, J=10.71 Hz), 7.08-7.09 (t, 1H), 7.36-7.59 (m, 7H), 7.75-7.78 (dd, 1H, J=1.83 Hz and 1.62 Hz), 7.85 (s, 1H); MS (m/z) 340 (100). HRMS (TOF) Calcd for $C_{21}H_{16}N_4ONa$ (M+Na)+ 363.1222, found: 363.1202.

8-Ethynyl-N-methyl-6-(2-fluorophenyl)-4H-benzo[f] imidazo[1,5-a][1,4]diazepine-3-carboxamide (16)

Compound 16 (HJ-1-37) was prepared in 75% yield from 1 using the procedure described above. 16: mp 235-236° C.; $^1H$ NMR ($CDCl_3$) δ 2.96-2.98 (d, 3H, J=4.57 Hz), 3.16 (s, 1H), 4.10 (bs, 1H), 6.29 (bs, 1H), 6.96-7.02 (t, 1H), 7.14 (bs, 1H), 7.21-7.26 (t, 1H), 7.39-7.46 (m, 2H), 7.52-7.55 (d, 1H), 7.65-7.73 (m, 2H), 7.86 (s, 1H). HRMS (TOF) Calcd for $C_{20}H_{15}FN_4ONa$ (M+Na)+ 381.1128, found: 381.1140.

8-Ethynyl-N-methyl-6-(pyridine-2-yl)-4H-benzo[f] imidazo[1,5-a][1,4]diazepine-3-carboxamide (17)

Compound 17 (HJ-1-40) was prepared in 80% yield from 1 using the procedure described above. 17: mp 215-216° C.; $^1H$ NMR ($CDCl_3$) δ 2.97-2.99 (d, 3H, J=4.88 Hz), 3.16 (s, 1H), 4.12 (bs, 1H), 6.29 (bs, 1H), 7.14-7.15 (bs, 1H), 7.33-7.37 (t, 1H), 7.51-7.57 (m, 2H), 7.71-7.84 (m, 3H), 8.12-8.15 (d, 1H), 8.55-8.57 (d, 1H). HRMS (TOF) Calcd for $C_{20}H_{16}N_5O$ (M+H)+ 342.1355, found: 342.1365.

Example 3

Synthesis of SR-II-97

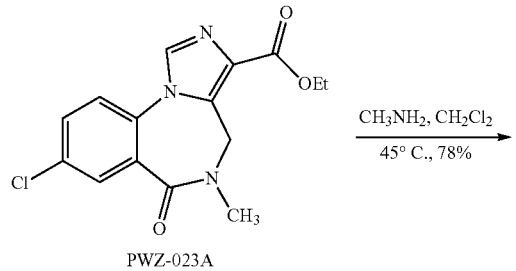

PWZ-023A

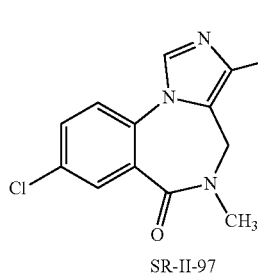

SR-II-97

8-chloro-N,5-dimethyl-6-Oxo-5,6-dihydro-4H-benzo[f]imidazo[1,5-a][1,4]diazepine-3-carboxamide Ester PWZ-023A (100 mg, 0.313 mmol) was dissolved in anhydrous CH$_2$Cl$_2$ (5 mL). To this mixture CH$_3$NH$_2$ solution (0.147 mL, 1.56 mmol) was added. This reaction mixture was placed in a preheated oil bath at 45° C. overnight. The solvent was then removed under reduced pressure and residue was flash chromatographed with CH$_2$Cl$_2$/MeOH (4.5:0.5) to provide the amine SR-II-97 (74 mg, 78% yield). $^1$H NMR (CDCl$_3$, 300 MHz) δ 8.08 (d, 1H, J=2.35 Hz), 7.94 (s, 1H), 7.64 (m, 1H), 7.42 (m, 2H), 5.42 (br, 1H), 4.45 (br, 1H), 3.28 (s, 3H), 3.02 (d, 3H, J=3.9 Hz) MS (EI) m/e 304 (M$^+$, 100). Anal. Calcd. For C$_{14}$H$_{13}$ClN$_4$O$_2$.0.28; H$_2$O; C, 54.25; H, 4.41; N, 18.07. Found 54.39; H, 4.52; N, 17.69.

Example 4

Synthesis of 8-Ethynyl-N,N-Dimethyl-6-(Pyridine-2-yl)-4H-Benzo-[f]-Imidazo-[1,5-a]-[1,4]-Diazepine-3-Carboxamide (ZJW-II-61)

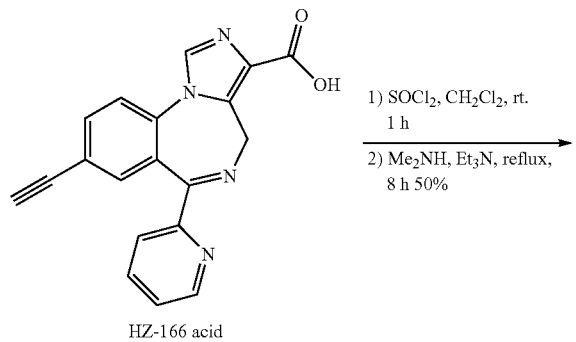

HZ-166 acid

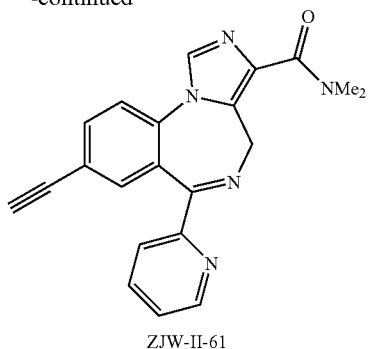

ZJW-II-61

HZ-166 acid (1 mmol) was dissolved in CH$_2$Cl$_2$ (5 mL). The suspension which resulted was added SOCl$_2$ (0.5 mL) and stirred at r. t. for 1 h during which time it became a clear solution. After removing the solvent under reduced pressure, the residue was redissolved in CH$_2$Cl$_2$ (5 mL) and was treated with Et$_3$N (0.2 mL) and Me$_2$NH (0.2 mL). After stirring at reflux for 8 h, the reaction was quenched with water (5 mL). The organic layer was washed with brine (5 mL) and dried (Na$_2$SO$_4$). After removing the solvent under reduced pressure, the residue was purified by a wash column (silica gel, gradient elution CH$_2$Cl$_2$-0.5% MeOH in CH$_2$Cl$_2$) to afford the amide (ZJW-II-61, 50%) as a light yellow powder: mp 193-194° C. $^1$H NMR (CDCl$_3$) δ 3.10 (s, 3H), 3.16 (s, 1H), 3.35 (s, 1H), 4.17-4.21 (d, 1H, J=12.09 Hz), 5.89-5.93 (d, 1H, J=12 Hz), 7.35-7.39 (m, 1H), 7.52-7.55 (m, 2H), 7.73-7.86 (m, 3H), 8.10-8.07 (d, 1H, J=7.8 Hz), 8.58-8.59 (d, 1H, J=4.8 Hz); $^{13}$C NMR (300 MHz, CDCl$_3$) δ 35.9, 39.1, 45.2, 79.3, 81.8, 120.9, 122.7, 124, 124.7, 127, 132.6, 133.3, 135.2, 135.8, 136.2, 136.8, 136.9, 148.7, 156.7, 164.5, 167.4. HRMS (ESI) m/z calcd for C$_{21}$H$_{18}$N$_5$O (M+H)$^+$ 356.1511, found: 356.1528.

Example 5

Synthesis of S-Methyl-8-Ethynyl-Methyl-6-(Pyridine-2-yl)-4H-Benzo-[f]-Imidazo-[1,5-a]-[1,4]-Diazepine-3-Carbothioate (ZJW-II-65)

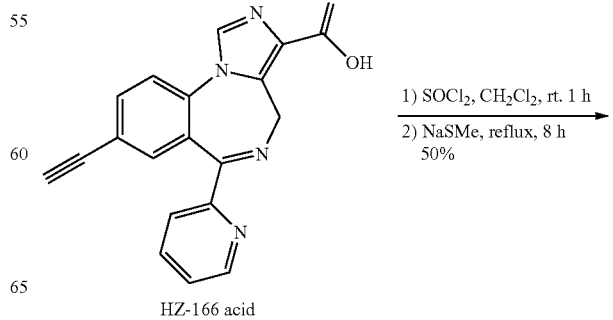

HZ-166 acid

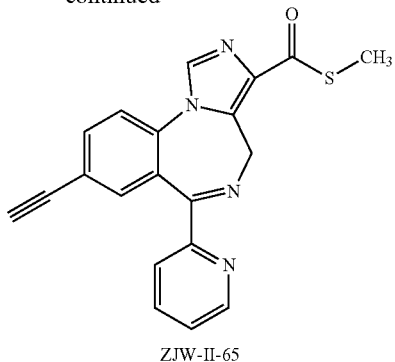

ZJW-II-65

HZ-166 acid (1 mmol) was dissolved in CH$_2$Cl$_2$ (5 mL). The suspension which resulted was added SOCl$_2$ (0.5 mL) and stirred at r. t. for 1 h during which time it became a clear solution. After removing the solvent under reduced pressure, the residue was redissolved in CH$_2$Cl$_2$ (5 mL) and was treated with NaSMe. After stirring at reflux for 8 h, the reaction was quenched with water (5 mL). The organic layer was washed with brine (5 mL) and dried (Na$_2$SO$_4$). After removing the solvent under reduced pressure, the residue was purified by a wash column (silica gel, gradient elution CH$_2$Cl$_2$-0.5% MeOH in CH$_2$Cl$_2$) to afford the thioate (ZJW-II-65, 50%) as a dark yellow powder: mp>200° C. (Dec.). $^1$H NMR (CDCl$_3$) δ 2.42 (s, 3H), 3.17 (s, 1H), 4.13 (br, 1H), 6.08 (br, 1H), 7.33-7.37 (m, 1H), 7.53-7.56 (m, 2H), 7.73-7.83 (m, 2H), 7.84 (s, 1H), 8.07-8.09 (d, 1H, J=8.1 Hz), 8.54-8.56 (d, 1H, J=3.9 Hz); $^{13}$C NMR (300 MHz, CDCl$_3$) δ 11, 44.7, 79.6, 81.7, 121.3, 122.8, 124, 124.8, 127.2, 134.2, 134.3, 135.1, 135.2, 135.3, 136.3, 136.9, 148.7, 156.4, 167.6, 188.1. HRMS (ESI) m/z calcd for C$_{20}$H$_{15}$N$_4$OS (M+H)$^+$ 359.0967, found: 359.0967.

Example 6

Synthesis of 1,2,4-oxodiazole analogs

General Procedure for the Synthesis of 1,2,4-Oxodiazole Analogs

Isopropyl amido oxime (95 mg, 0.93 mmol) was added to a stirred suspension of powdered 4 Å molecular sieves (100 mg) in anhydrous THF (30 mL) under a nitrogen atmosphere. After the mixture was stirred at rt for 10 min, NaH (37 mg, 60% dispersion in mineral oil, 0.93 mmol) was added to the mixture. After the mixture was stirred for a further 30 min, a solution of ester in anhydrous THF (30 mL) was added. The mixture that resulted was heated to reflux for 8 h. The reaction mixture was cooled to rt, after which acetic acid (56 mg, 0.93 mmol) was added. After the solution was stirred for 10 min, the mixture was filtered through celite. The filtrate was diluted with CH$_2$Cl$_2$ (75 mL) and washed with water, brine and dried (K$_2$CO$_3$). Evaporation of the solvent under reduced pressure afforded a pale yellow solid, which was purified by flash column chromatography (silica gel, EtOAc/hexane, 2:3) to furnish the oxodiazole product.

5-(8-Ethynyl-6-(pyridin-2-yl)-4H-Benzo-[f]-Imidazo-[1,5-a]-[1,4]-Diazepine-3-yl)-3-Isopropyl-1,2,4-Oxadiazole (ZJW-II-40)

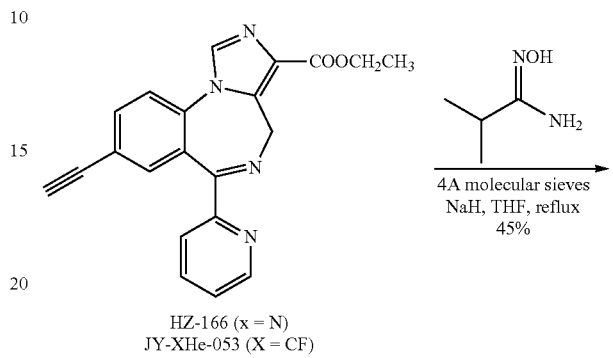

HZ-166 (x = N)
JY-XHe-053 (X = CF)

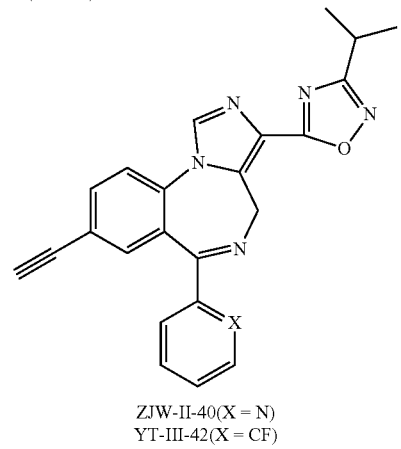

ZJW-II-40(X = N)
YT-III-42(X = CF)

Isopropyl amido oxime (95 mg, 0.93 mmol) was added to a stirred suspension of powdered 4 Å molecular sieves (100 mg) in anhydrous THF (30 mL) under a nitrogen atmosphere. After the mixture was stirred at rt for 10 min, NaH (37 mg, 60% dispersion in mineral oil, 0.93 mmol) was added to the mixture. After the mixture was stirred for a further 30 min, a solution of ester 1 (X=N, HZ-166, 165 mg, 0.47 mmol) in anhydrous THF (30 mL) was added. The mixture that resulted was heated to reflux for 8 h. The reaction mixture was cooled to rt, after which acetic acid (56 mg, 0.93 mmol) was added. After the solution was stirred for 10 min, the mixture was filtered through celite. The filtrate was diluted with CH$_2$Cl$_2$ (75 mL) and washed with water, brine and dried (K$_2$CO$_3$). Evaporation of the solvent under reduced pressure afforded a pale yellow solid, which was purified by flash column chromatography (silica gel, EtOAc/hexane, 2:3) to furnish ZJW-II-40 as a white solid in 45% yield (82 mg): mp>200° C. (Dec.); $^1$H NMR (CDCl$_3$) δ 1.42-1.44 (d, 6H, J=6.93 Hz), 3.13-3.27 (m, 2H), 4.27-4.31 (d, 1H, J=10.8 Hz), 6.14-6.18 (d, 1H, J=10.8 Hz), 7.36-7.40 (m, 1H), 7.59-7.62 (m, 2H), 7.77-7.86 (m, 2H), 8.04-8.09 (m, 2H), 8.58-8.60 (m, 1H); $^{13}$C NMR (300 MHz, CDCl$_3$) δ 20.5, 26.7, 44.8, 79.5, 81.5, 121.3, 122.7, 123.9, 124.8, 127, 135.2, 135.3, 135.7, 136, 136.2, 136.8, 148.7, 156.3, 167.8, 170.6, 175.2, 190.2; HRMS (ESI) Calcd for C$_{23}$H$_{19}$N$_6$O (M+H)$^+$ 395.1620, found: 395.1635.

5-(8-Ethynyl-6-(2-Fluorophenyl)-4H-Benzo-[f]-Imidazo-[1,5-a]-[1,4]-Diazepine-3-yl)-3-Isopropyl-1,2,4-Oxadiazole (YT-III-42)

YT-III-42 was prepared in 45% yield from JY-XHe-053 using the procedure described above: mp 160-165° C.; IR (neat) ν3194, 2961, 2924, 2854, 1631, 1610, 1495, 1450, 1414, 1394, 1367, 1342, 1312, 1259, 1221, 1071, 1011, 940, 903, 862, 793, 767, 754, 697, 671 cm$^{-1}$; $^1$H NMR (300 MHz, CDCl$_3$) δ8.09 (s, 1H), 7.80 (dd, 1H, J=1.78, 1.78 Hz), 7.69 (m, 3H), 7.51 (m, 2H), 7.07 (m, 1H), 6.26 (brs, 1H), 4.40 (brs, 1H), 3.24 (m, 2H), 1.43 (d, 6H, J=6.93 Hz); MS (EI) m/e (relative intensity) 411(43), 383 (M$^+$, 98), 325(100), 299(74), 178(74), 57 (57); HRMS (ESI) Calcd for $C_{24}H_{18}FN_5O$ (M+H)$^+$ 412.1644, found: 412.1628.

8-chloro-5-methyl-6-Oxo-5,6-dihydro-4H-benzo[f]imidazo[1,5-a][1,4]diazepine-3-carbohydrazide (ON-IV-13)

To a solution of ethyl ester PWZ-023A (175 mg, 0.57 mmol) in EtOH (2 mL) was added hydrazine monohydrate (0.083 mL, 1.71 mmol). The resulting solution is refluxed for 5 h. The mixture was cooled to rt and the solvent was removed under reduced pressure. To the residue water (2 mL) was added and the milky white suspension was extracted with DCM (3×5 mL). The combined organic layers were washed with brine, dried with MgSO$_4$ and the solvent was removed under reduced pressure. The crude residue was purified by flash column chromatography on silica gel using pure EtOAc as eluent to afford pure ON-IV-13 as a white solid (148 mg, 85%). $^1$H NMR (300 MHz, DMSO-d$_6$): δ 9.39 (br, 1H), 8.34 (s, 1H), 7.81 (m, 3H), 5.17 (br, 1H), 4.46 (br, 3H), 3.09 (s, 3H); $^{13}$C NMR (75 MHz, DMSO-d$_6$) δ 165.1, 161.8, 135.8, 132.8, 132.7, 132.2, 131.6, 131.3, 130.6, 130.3, 125.3, 40.8, 35.8; HRMS (ESI) calcd for $C_{13}H_{13}ClN_5O_2$(M+H$^+$): 306.0758, found: 306.0764.

Synthesis of 8-chloro-5-methyl-3-(5-methyl-4H-1,2,4-triazol-3-yl)-4H-benzo[f]imidazo[1,5-a][1,4]diazepin-6(5H)-one (ON-IV-14)

Sodium methoxide was freshly prepared by stirring dry methanol (0.5 mL) with sodium (15 mg, 0.66 mmol) under argon at 0° C. After complete reaction acetamidine hydrochloride (62 mg, 0.66 mmol) was added as solid. The white mixture was stirred for additional 30 minutes. The hydrazide ON-IV-13 (50 mg, 0.163 mmol) was dissolved in dry methanol (0.5 mL) under argon and the freshly prepared free base acetamidine (first solution) was added to the hydrazide. The clear mixture was stirred for 16 h at rt and then was directly refluxed until full conversion of the starting material was obtained. The mixture was then cooled to rt and concentrated under reduced pressure. Water (1 mL) was added as the mixture turns milky white immediately and the water layer is extracted with EtOAc (3×5 mL). The combined organic layers were dried with MgSO$_4$ and the solvent was removed under reduced pressure. The crude residue was purified by flash column chromatography on silica gel using DCM/MeOH; 10:1 as eluent to afford pure ON-IV-14 as a white solid (43 mg, 82%). $^1$H NMR (300 MHz, CDCl$_3$) δ 8.06 (d, 1H, J=2.1 Hz), 7.80 (s, 1H), 7.61 (dd, 1H, J$_1$=8.4 Hz, J$_2$=2.1 Hz), 7.37 (d, 1H, J=8.7 Hz), 5.47 (br, 1H), 4.32 (br, 1H), 3.26 (s, 3H), 2.13 (s, 3H); $^{13}$C NMR (75 MHz, CDCl$_3$) δ 165.4, 159.6, 157.0, 134.5, 133.6, 132.7, 132.6, 130.8, 130.7, 130.6, 130.5, 123.0, 42.1, 36.1, 20.1; HRMS (ESI) calcd for $C_{15}H_{14}ClN_6O$ (M+H$^+$): 329.0842, found: 329.0826.

Example 7

Synthesis of Bivalent Ligands

General Procedure for the Synthesis of Bivalent Ligands

The dry carboxylic acid (0.5 g, 1.7 mmol) was dissolved in dry DMF (25 mL) and was maintained under argon, after which CDI (0.33 g, 2.1 mmol) was added at 40° C. and the mixture was stirred for 2 h. At this point dry 1,3-propanediol (59.9 mg, 0.77 mmol) and DBU (0.31 mL, 2.1 mmol) were added to the mixture and stirring continued for 2 h at 40° C. The reaction solution was then cooled with an ice-water bath, after which water was added to precipitate a solid. This material was further purified by flash chromatography on silica gel (gradient elution, CH$_2$Cl$_2$:MeOH 20:1, 15:1, 10:1) to provide the diester.

Propane-1,3-Diyl-Bis-(8-Chloro-5-Methyl-6-Oxo-5,6-Dihydro-4H-Benzo-[f]-Imidazo-[1,5-a]-[1,4]-Diazaepine-3-Carboxylate (YT-TC-1)

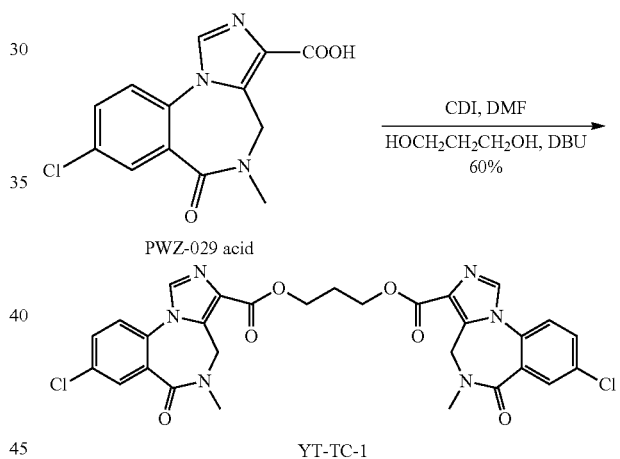

The dry PWZ-029 acid (0.5 g, 1.7 mmol) was dissolved in dry DMF (25 mL) and was maintained under argon, after which CDI (0.33 g, 2.1 mmol) was added at 40° C. and the mixture was stirred for 2 h. At this point dry 1,3-propanediol (59.9 mg, 0.77 mmol) and DBU (0.31 mL, 2.1 mmol) were added to the mixture and stirring continued for 2 h at 40° C. The reaction solution was then cooled with an ice-water bath, after which water was added to precipitate a solid. This material was further purified by flash chromatography on silica gel (gradient elution, CH$_2$Cl$_2$:MeOH 20:1, 15:1, 10:1) to provide YT-TC-1 as a white solid (0.32 g, 60%): mp 246-249° C.; IR (neat) ν 3110, 1735, 1644, 1496, 1354, 1163, 1120, 1060, 942, 835, 659 cm$^{-1}$; $^1$H NMR (300 MHz, CDCl$_3$) δ 8.12 (d, J=1.47 Hz, 2H), 7.92 (s, 2H), 7.68 (dd, J=1.47, 1.47 Hz, 2H), 7.44 (d, J=5.13 Hz, 2H), 5.27 (br s, 2H), 4.63 (t, 4H), 4.44 (br s, 2H), 3.31 (s, 6H), 2.45-2.40 (m, 2H); MS (EI) m/e (relative intensity) 622 (M$^+$, 50), 332(13), 291(12), 273(53), 245(100), 231(16), 217 (33). Anal. Calcd. for $C_{29}H_{24}Cl_2N_6O_6$.0.7H$_2$O: C, 54.72; H, 4.03; N, 13.20. Found: C, 54.75; H, 3.85; N, 12.96.

Butane-1,4-Diyl-Bis-(8-Chloro-5-Methyl-6-Oxo-5,6-Dihydro-4H-Benzo-[f]-Imidazo-[1,5-a]-[1,4]-Diazepine-3-Carboxylate (YT-TC-2)

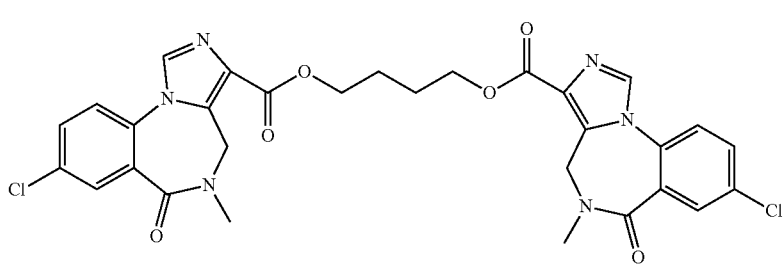

YT-TC-2

YT-TC-2 was prepared in 55% yield using the procedure described above: mp 308-312° C.; IR (neat) 3077, 2927, 1694, 1650 cm$^{-1}$; $^1$H NMR (300 MHz, CDCl$_3$) δ 8.12 (d, J=1.47 Hz, 2H), 7.92 (s, 2H), 7.68 (dd, J=1.47, 1.47 Hz, 2H), 7.44 (d, J=5.13 Hz, 2H), 5.27 (br s, 2H), 4.63 (t, 4H), 4.44 (br s, 2H), 3.31 (s, 6H), 2.07 (m, 4H); MS (EI) m/e (rel. intensity) 636 (M$^+$, 28), 341(17), 274(78), 245(100), 231(14), 217 (28). HRMS (CI) calcd for C$_{30}$H$_{26}$Cl$_2$N$_6$O$_6$(M+H)$^+$ 637.1369, found 637.1345.

Pentane-1,5-Diyl-Bis-(8-Chloro-5-Methyl-6-Oxo-5,6-Dihydro-4H-Benzo-[f]-Imidazo-[1,5-a]-[1,4]-Diazepine-3-Carboxylate (YT-TC-3)

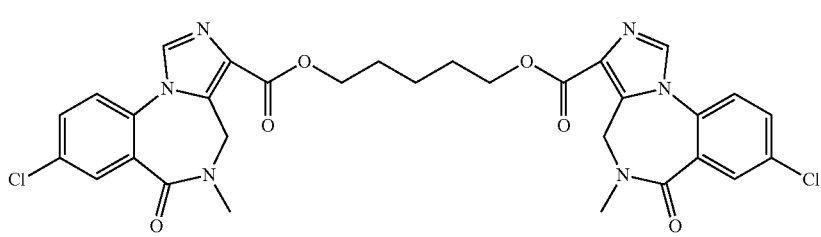

YT-TC-3

YT-TC-3 was prepared in 55% yield using the procedure described above: mp 146-152° C.; IR (neat) ν 3397, 3105, 2938, 1724, 1639 cm$^{-1}$; $^1$H NMR (300 MHz, CDCl$_3$) δ 8.12 (d, J=1.47 Hz, 2H), 7.92 (s, 2H), 7.68 (dd, J=1.47, 1.47 Hz, 2H), 7.44 (d, J=5.13 Hz, 2H), 5.27 (br s, 2H), 4.46 (s, 6H), 3.31 (s, 6H), 1.65-1.70 (m, 6H); MS (EI) m/e (rel. intensity) 650 (M$^+$, 51), 273(59), 245(100), 231(14), 217 (30). Anal. Calcd. for C$_{31}$H$_{28}$Cl$_2$N$_6$O$_6$·0.3CH$_2$Cl$_2$: C, 55.48; H, 4.26; N, 12.40. Found: C, 55.54; H, 4.39; N, 12.15. (CHN sample was transferred to a vial for drying with CH$_2$Cl$_2$ which may explain the contaminant.)

3,3'-(piperazine-1,4-Diyl-Bis(Oxomethylene))-Bis(8-Chloro-5-Methyl-4H-Benzo-[f]-Imidazo-[1,5-a]-[1,4]-Diazepine-6-(5H)-one) (YT-TC-4)

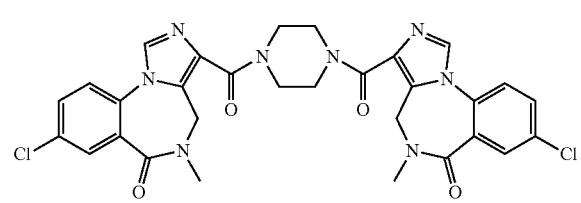

YT-TC-4

YT-TC-4 was prepared in 62% yield using the procedure described above: mp 367-374° C.; IR (neat) ν 2867, 1649, 1595, 1559 cm$^{-1}$; $^1$H NMR (300 MHz, CDCl$_3$) δ 8.12 (d, J=1.47 Hz, 2H), 7.88 (d, J=11.13 Hz, 2H), 7.68 (dd, J=1.23, 1.20 Hz, 2H), 7.44 (d, J=5.37 Hz, 2H), 5.23 (s, 2H), 4.50 (s, 2H), 4.40 (s, 4H), 3.95 (s, 4H), 3.36 (s, 6H); MS (EI) m/e (rel. intensity) 632 (M$^+$, 23), 358(13), 318(11), 274(100), 245(68), 217 (16). Anal. Calcd. for C$_{30}$H$_{26}$Cl$_2$N$_8$O$_4$·H$_2$O: C, 55.31; H, 4.33; N, 17.20. Found: C, 55.22; H, 4.26; N, 17.46.

(13aS,13a'S)-Propane-1,3-Diyl-Bis-(7-Bromo-9-Oxo-11,12,13,13a-Tetrahydro-9H-Benzo-[e]-Imidazo-[5,1-c]-Pyrrolo-[1,2-a]-[1,4]-Diazepine-1-Carboxylate) (YT-II-791)

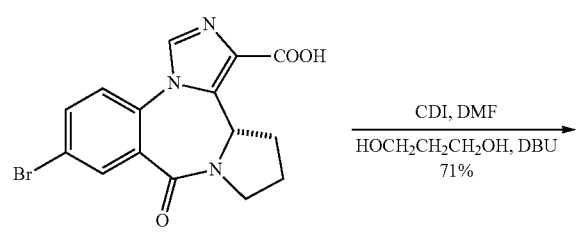

RY-10 acid $\xrightarrow[\text{HOCH}_2\text{CH}_2\text{CH}_2\text{OH, DBU}]{\text{CDI, DMF}}$ 71% after which CDI (0.16 g, 0.99 mmol) was added at 40° C. and the mixture was stirred for 2 h. At this point dry 1,3-propanediol (28.4 mg, 0.37 mmol) and DBU (0.15 mL, 0.99 mmol) were added to the mixture and stirring continued for 2 h at 40° C. The reaction solution was then cooled with an ice-water bath, after which water was added to precipitate a solid. This solid material was further purified by flash chromatography on silica gel (gradient elution, $CH_2Cl_2$: MeOH 20:1, 15:1, 10:1) to provide the bivalent YT-II-791 (0.37 g, 71%) as a white solid[170]: mp 159-161° C.; IR (neat) v 3380, 2980, 1722, 1637, 1551, 1447, 1378, 1255, 1171, 1120, 965 cm$^{-1}$. $^1$H NMR (300 MHz, CDCl$_3$) δ 8.29 (d, J=2.28 Hz, 2H), 7.84 (s, 2H), 7.80 (dd, J=2.34, 2.33 Hz, 2H), 7.32 (s, 2H), 4.81 (d, J=4.41 Hz, 2H), 4.58 (t, 4H), 3.85 (m, 2H), 3.63 (m, 4H), 2.43 (m, 2H), 2.29 (m, 6H); MS (EI) m/e (rel. intensity) 764 (M$^+$, 10), 345(67), 317(100), 289(22), 237 (13). Anal. Calcd. for $C_{33}H_{28}Br_2N_6O_6 \cdot 0.6H_2O$: C, 51.17; H, 3.79; N, 10.85. Found: C, 51.19; H, 3.77; N, 10.77.

(13aS,13a'S)-Butane-1,4-Diyl-Bis-(7-Bromo-9-Oxo-11,12,13,13a-Tetrahydro-9H-Benzo-[e]-Imidazo-[5,1-c]-Pyrrolo-[1,2-a]-[1,4]-Diazepine-1-Carboxylate) (YT-II-792)

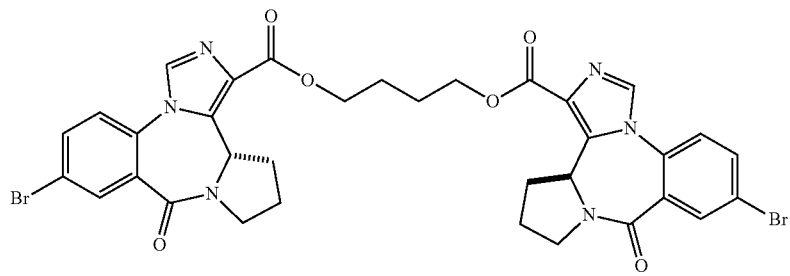

YT-II-792

YT-II-792 was prepared in 73% yield using the procedure described above: mp 166-171° C.; IR (neat) v3437, 2971, 1719, 1638, 1549 cm$^{-1}$; $^1$H NMR (300 MHz, CDCl$_3$) δ 8.29 (d, J=2.28 Hz, 2H), 7.84 (s, 2H), 7.80 (dd, J=2.34, 2.33 Hz, 2H), 7.32 (s, 2H), 4.78 (d, J=6.94 Hz, 2H), 4.43 (m, 4H), 3.89 (m, 2H), 3.60 (m, 4H), 2.25 (m, 4H), 2.01 (m, 6H); MS (EI) m/e (relative intensity) 778 (M$^+$, 32), 345(63), 317(100), 237(18), 152 (13). Anal. Calcd. for $C_{34}H_{30}Br_2N_6O_6 \cdot 0.6H_2O$: C, 51.73; H, 3.99; N, 10.65. Found: C, 51.72; H, 3.91; N, 10.67.

(13aS,13a'S)-Pentane-1,5-Diyl-Bis-(7-Bromo-9-Oxo-11,12,13,13a-Tetrahydro-9H-Benzo-[e]-Imidazo-[5,1-c]-Pyrrolo-[1,2-a]-[1,4]-Diazepine-1-Carboxylate) (YT-II-793)

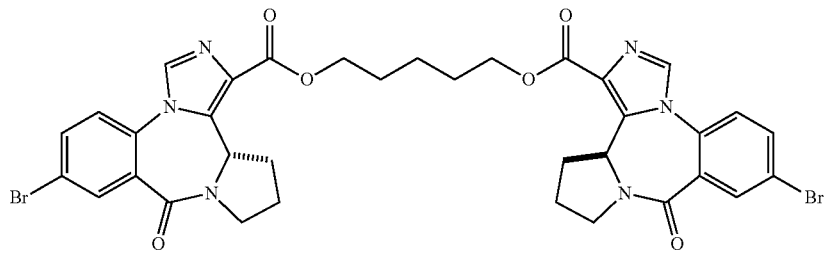

YT-II-793

YT-II-793 was prepared in 70% yield using the procedure described above: mp 157-161° C.; IR (KBr) v3440, 2951, 1717, 1638, 1547 cm$^{-1}$; $^1$H NMR (300 MHz, CDCl$_3$) δ8.28 (d, J=2.28 Hz, 2H), 7.84 (s, 2H), 7.80 (dd, J=2.34, 2.33 Hz, 2H), 7.32 (s, 2H), 4.78 (d, J=6.94 Hz, 2H), 4.43 (t, 4H), 3.84 (t, 2H), 3.60 (m, 4H), 2.20 (m, 6H), 1.83 (m, 6H); MS (EI) m/e (relative intensity) 792 (M$^+$, 13), 345(51), 317(100), 261 (31). Anal. Calcd. for $C_{35}H_{32}Br_2N_6O_6$: C, 53.05; H, 4.07; N, 10.60. Found: C, 52.87; H, 4.31; N, 10.80.

Propane-1,3-Diyl-Bis-(8-Ethynyl-6-(2-Fluorophenyl)-4H-Benzo-[f]-Imidazo-[1,5-a]-[1,4]-Diazepine-3-Carboxylate) YT-III-271

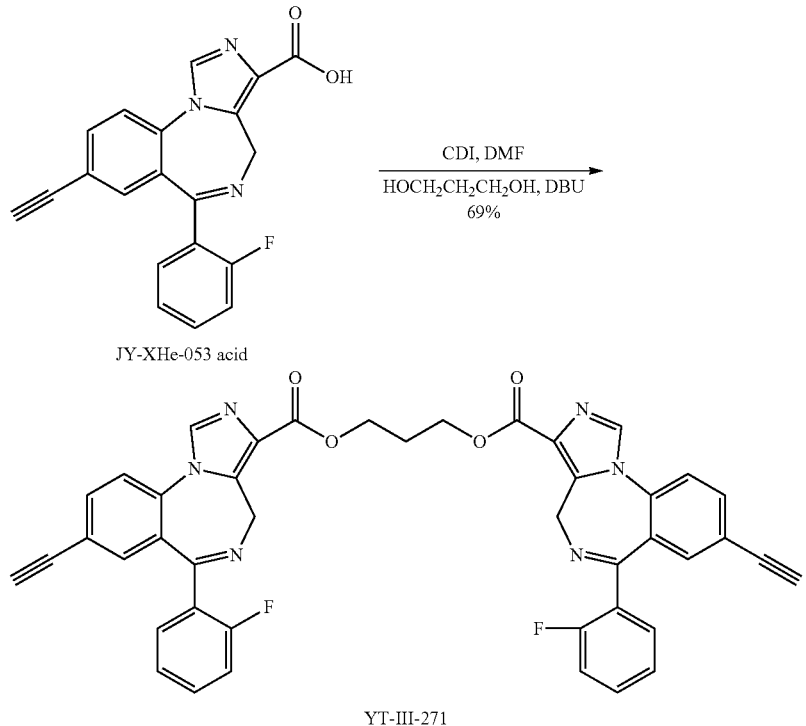

The dry JY-XHe-053 acid (0.5 g, 1.4 mmol) was dissolved in dry DMF (25 mL) and was maintained under argon, after which CDI (0.28 g, 1.7 mmol) was added at 40° C. and the mixture was stirred for 2 h. At this point dry 1,3-propanediol (49.3 mg, 0.65 mmol) and DBU (0.26 g, 1.7 mmol) were added to the mixture and stirring continued for 2 h at 40° C. The reaction solution was then cooled with an ice-water bath, after which water was added to precipitate a solid. This solid material was further purified by flash chromatography on silica gel (gradient elution, $CH_2Cl_2$:MeOH 20:1, 15:1, 10:1) to provide YT-III-271 as a white solid (0.37 g, 69%). mp: 130-135° C.; IR (KBr) 3293, 2925, 2854, 1715, 1614, 1494, 1452, 1361, 1313, 1258, 1164, 1126, 1075, 954, 835, 765 $cm^{-1}$. $^1$H NMR (300 MHz, $CDCl_3$) δ 7.98 (s, 2H), 7.78 (dd, 2H, J=1.8, 1.83 Hz), 7.66 (dd, 2H, J=1.74, 1.76 Hz), 7.49 (m, 8H), 7.07 (t, 2H), 6.10 (brs, 2H), 4.57 (m, 4H), 4.00 (brs, 2H), 3.17 (s, 2H), 2.05 (m, 2H); HRMS (CI) Calcd. for $C_{43}H_{28}F_2N_6O_4$ $(M+H)^+$ 731.2218, found 731.2214.

Propane-1,3-Diyl-Bis-(8-Ethynyl-6-(2-Fluorophenyl)-4H-Benzo-[f]-Imidazo-[1,5-a]-[1,4]-Diazepine-3-Carboxylate) YT-III-273

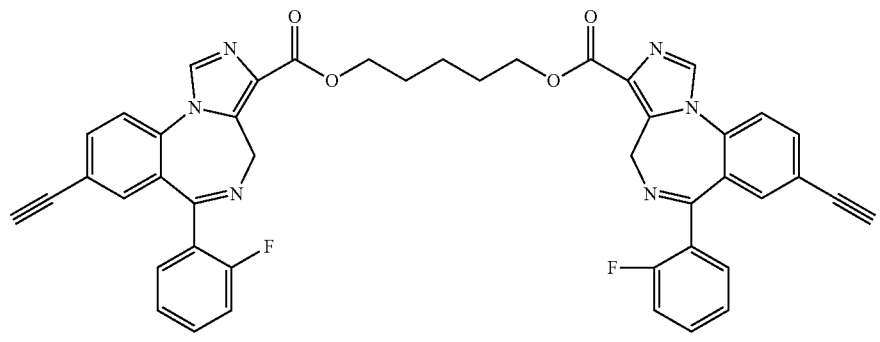

YT-III-273

YT-III-273 was prepared in 70% yield using the procedure described above: mp: 100-105° C.; IR (KBr) 3293, 2925, 2855, 1724 $cm^{-1}$; $^1$H NMR (300 MHz, $CDCl_3$) δ 7.98 (s, 2H), 7.76 (m, 12H), 7.03 (t, 2H), 4.40 (m, 6H), 4.15 (brs, 2H), 3.17 (s, 2H), 1.73 (m, 6H); HRMS (CI) Calcd. for $C_{45}H_{32}F_2N_6O_4$ $(M+H)^+$ 759.2531, found 759.2529.

Propane-1,3-Diyl-Bis-(8-Ethynyl-6-(2-Fluorophenyl)-4H-Benzo-[f]-Imidazo-[1,5-a]-[1,4]-Diazepine-3-Carboxylate) (YT-III-274)

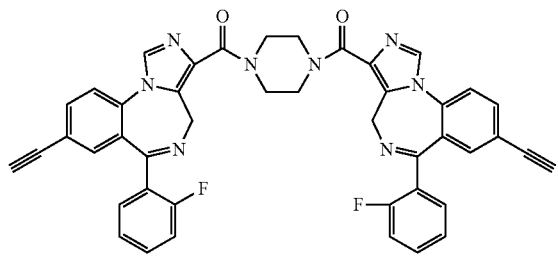

YT-III-274

YT-III-274 was prepared in 65% yield using the procedure described above: mp>300° C.; $^1$H NMR (300 MHz, CDCl$_3$) δ 7.98 (s, 2H), 7.78 (dd, 2H, J=1.8, 1.83 Hz), 7.66 (dd, 2H, J=1.74, 1.76 Hz), 7.49 (m, 8H), 7.07 (t, 2H), 5.93 (brs, 2H), 4.25 (m, 6H), 3.89 (m, 4H), 3.21 (s, 2H); HRMS (ESI) calcd for $C_{44}H_{30}F_2N_8O_2(M^+)$ 741.2538, found 741.2541.

(S)-3-((S)-8-Ethynyl-6-(2'-Fluorophenyl)-4-Methyl-4H-Benzo-[f]-Imidazo-[1,5-a]-[1,4]-Diazepine-3-Carbonyloxy)-Propyl-8-Ethynyl-6-(2'-Fluorophenyl)-4-Methyl-4H-Benzo-[f]-Imidazo-[1,5-a]-[1,4]-Diazepine-3-Carboxylate (YT-III-331)

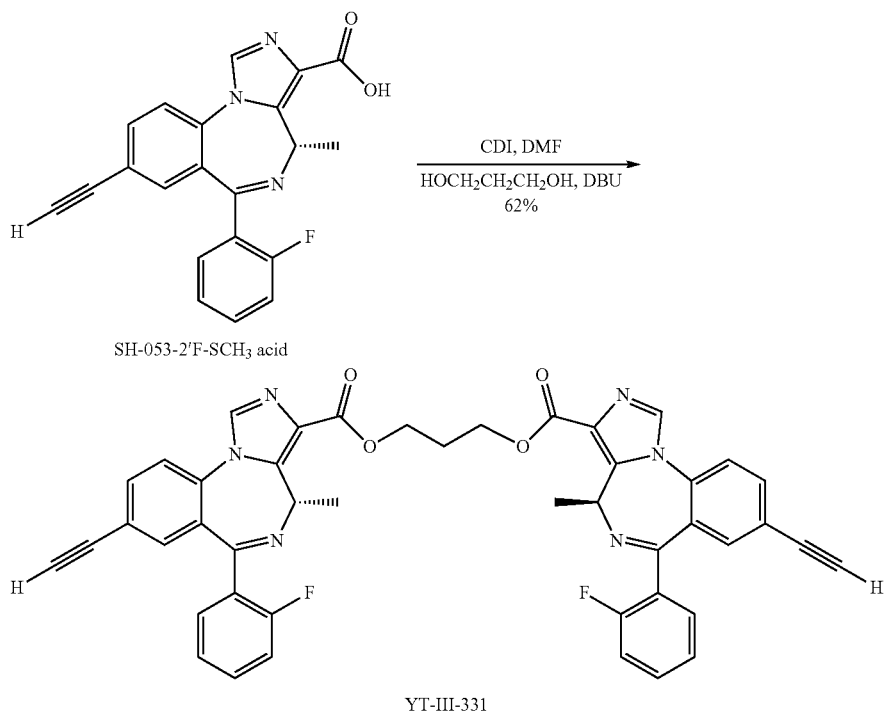

The dry SH-053-2'-SCH3 acid (1.9 g, 5.2 mmol) was dissolved in dry DMF (20 mL) and was maintained under argon, after which CDI (1.02 g, 6.3 mmol) was added at rt and the mixture was stirred for 2 h. At this point dry 1,3-propanediol (0.19 mL, 2.6 mmol) and DBU (0.78 mL, 5.2 mmol) were added to the mixture and stirring continued overnight at rt. The reaction solution was then cooled with an ice-water bath, after which water was added to precipitate a solid. This material was further purified by flash chromatography on silica gel (gradient elution, CH$_2$Cl$_2$:MeOH 20:1, 15:1, 10:1) to provide YT-III-331 as a white solid (1.20 g, 61.9%): mp 158-160° C.; $[\alpha]_D^{26}$=+13.51 (c=0.37, CH$_2$Cl$_2$); IR (KBr) 3400, 3293, 3113, 3055, 2973, 2932 cm$^{-1}$; $^1$H NMR (300 MHz, CDCl$_3$) δ 7.94 (s, 2H), 7.70 (d, J=7.95 Hz, 2H), 7.59 (m, 4H), 7.46-7.41 (d, J=12.6 Hz, 4H), 7.24 (d, J=7.5 Hz, 2H), 7.04 (d, J=9.5 Hz, 2H), 6.67 (d, J=14.1 Hz, 2H), 4.55 (m, 4H), 3.15 (s, 2H), 2.32 (m, 2H), 1.28 (d, J=7.1 Hz, 6H); MS (EI) m/e (relative intensity) 758 (M$^+$, 2), 417 (7), 389 (15), 141 (100). Anal. Calcd For $C_{45}H_{32}F_2N_6O_4$: C, 71.23; H, 4.25; N, 11.08. Found: C, 71.28; H, 4.27; N, 11.10. F

(4S,4'S)-Butane-1,4-Diyl-Bis-(8-Ethynyl-6-(2'-Fluorophenyl)-4-Methyl-4H-Benzo-[f]-Imidazo-[1,5-a]-[1,4]-Diazepine-3-Carboxylate) (YT-III-332)

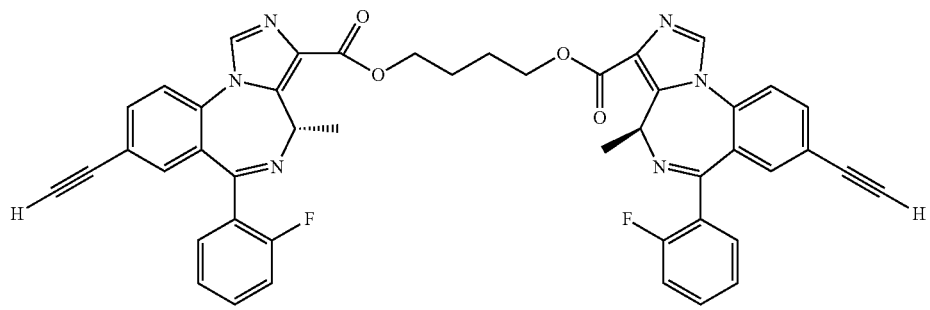

YT-III-332

YT-III-332 was prepared in 62% yield using the procedure described above: mp 158-160° C.; $[\alpha]_D^{26}=+3.90$ (c=0.41, $CH_2Cl_2$); IR (KBr) 3383, 2957, 2924, 2858 cm$^{-1}$; $^1$H NMR (300 MHz, CDCl$_3$) δ 7.94 (s, 2H), 7.69 (d, J=7.9 Hz, 2H), 7.57 (m, 4H), 7.46-7.40 (d, J=12.6 Hz, 4H), 7.26-7.21 (m, 2H), 7.02 (d, J=8.43 Hz, 2H), 6.67 (bd, J=7.1 Hz, 2H), 4.39 (m, 4H), 3.15 (s, 2H), 1.90 (m, 4H), 1.27 (bd, J=5.14, 6H); $^{13}$CNMR (300 MHz, CDCl$_3$) δ 162.8, 161.68, 135.0, 134.8, 133.8, 131.8, 131.1, 129.5, 124.4, 122.1, 116.2, 115.9, 81.3, 79.5, 64.5, 64.1, 62.0, 50.0, 29.6, 29.3, 25.3, 24.9, 14.7; MS (EI) m/e (relative intensity) 772 (M$^+$, 4), 431 (64), 341 (78), 313 (100). Anal. Calcd For $C_{46}H_{34}F_2N_6O_4$: C, 71.49; H, 4.43; N, 10.87. Found: C, 71.54; H, 4.45; N, 10.90.

(4S,4'S)-Pentane-1,5-Diyl-Bis-(8-Ethynyl-6-(2-Fluorophenyl)-4-Methyl-4H-Benzo-[f]-Imidazo-[1,5-a]-[1,4]-Diazepine-3-Carboxylate) (YT-III-333)

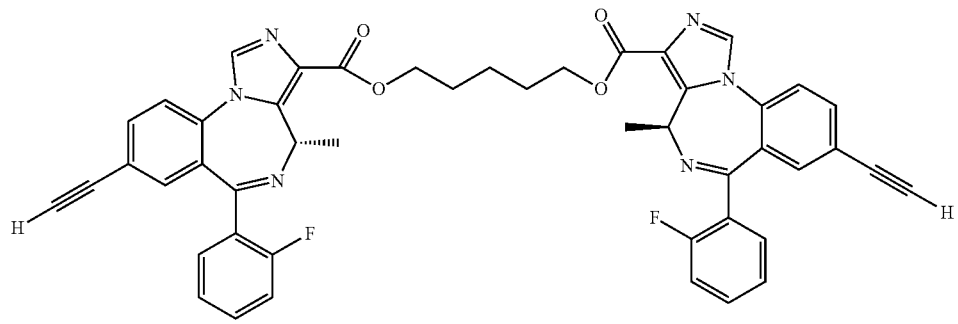

YT-III-333

YT-III-333 was prepared in 65% yield using the procedure described above: mp 150-155° C.; IR (KBr) 3295, 3050, 2938, 1713, 1618, 1486, 1255, 1181, 732 cm$^{-1}$; $^1$H NMR (300 MHz, CDCl$_3$) δ 8.07 (s, 2H), 7.58 (d, J=8.0 Hz, 2H), 7.49-7.39 (m, 8H), 7.13-7.09 (m, 2H), 6.96 (s, 2H), 4.45 (m, 6H), 3.15 (s, 2H), 1.93 (m, 6H), 1.58 (bd, J=5.14, 6H); MS (EI) m/e (relative intensity) 787 (M+H$^+$, 37), 446 (23), 342 (32), 307 (19), 154 (100); HRMS (EI) calcd for $C_{47}H_{36}F_2N_6O_4$(M$^+$) 787.2488, found 787.2389.

(S)-piperazine-1,4-Diyl-Bis-(((S)-8-Ethynyl-6-(2-Fluorophenyl)-4-Methyl-4H-Benzo-[f]-Imidazo-[1,5-a]-[1,4]-Diazepine-3-yl)-Methanone) (YT-III-334)

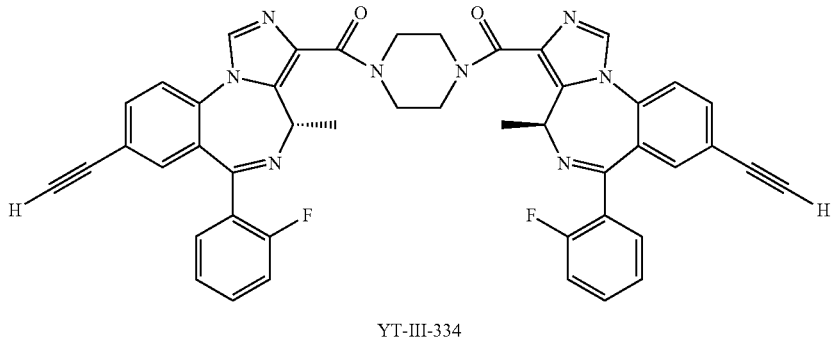 [SMILES: C#Cc1ccc2c(c1)C(c1ccccc1F)=N[C@@H](C)c1c(C(=O)N3CCN(C(=O)c4ncn5c4[C@H](C)N=C(c4ccccc4F)c4cc(C#C)ccc4-5)CC3)ncn1-2]

YT-III-334

YT-III-334 was prepared in 65% yield using the procedure described above: mp 180-190° C.; IR (KBr) 3295, 2927, 1623, 1477, 1376, 1263, 1230 cm$^{-1}$; $^1$H NMR (300 MHz, CDCl$_3$) δ 8.08 (s, 2H), 7.55 (m, 2H), 7.46 (m, 8H), 7.19 (m, 2H), 6.93 (s, 2H), 5.59 (d, 2H, J=26.1 Hz), 3.99 (m, 8H), 3.10 (s, 2H), 1.58 (m, 6H); MS (FAB$^+$) m/e (relative intensity) 769 (M$^+$, 16), 494 (13), 410(20), 342 (30), 301 (18), 154 (100); HRMS (ESI) calcd for C$_{46}$H$_{34}$F$_2$N$_8$O$_2$ (M$^+$) 769.2851, found 769.2848.

(13aS,13a'S)-1,1'-(piperazine-1,4-Diyl-Bis(Oxomethylene))-Bis-(7-Ethynyl-11,12,13,13a-Tetrahydro-9H-Benzo-[e]-Imidazo-[5,1-c]-Pyrrolo-[1,2-a]-[1,4]-Diazepine-9-one) (YT-III-30)

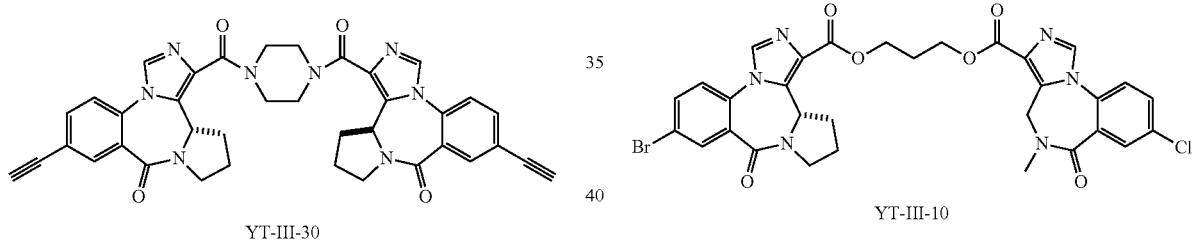

YT-III-30

YT-III-30 was prepared in 80% yield using the procedure described above: mp: 206-211° C.;. $^1$H NMR (300 MHz, CDCl$_3$) δ8.32 (d, 2H, J=1.89 Hz), 7.89 (s, 2H), 7.81 (dd, 2H, J=1.96, 1.97 Hz), 7.45 (d, 2H, J=8.33 Hz), 4.93 (d, 2H, J=8.43 Hz), 3.97 (m, 8H), 3.81 (d, 2H, J=7.92 Hz), 3.63 (m, 6H), 2.38 (m, 6H); HRMS (MALDI) Calcd. for C$_{38}$H$_{32}$N$_6$O$_6$ (M+H)$^+$ is 665.2546, found: 665.2619.

(S)-3-(8-Chloro-5-Methyl-5,6-Dihydro-4H-Benzo-[f]-Imidazo-[1,5-a]-[1,4]-Diazepine-3-Carbonyloxy)-Propyl-7-Bromo-9-Oxo-11,12,13,13a-Tetrahydro-9H-Benzo-[e]-Imidazo-[5,1-c]-Pyrrolo-[1,2-a]-[1,4]-Diazepine-1-Carboxylate) (YT-III-10)

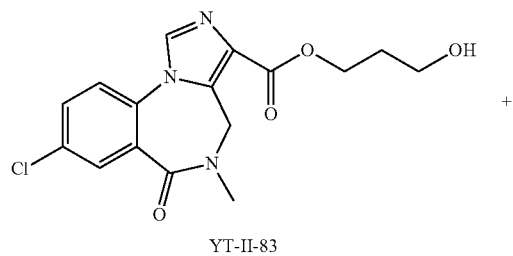

YT-II-83

+

-continued

[structure of RY-10 acid]

RY-10 acid

CDI, DBU, DMF
70%

[structure of YT-III-10]

YT-III-10

The dry RY-10 acid (0.5 g, 1.38 mmol) was dissolved in dry DMF (20 mL), and this was maintained under argon, after which CDI (0.27 g, 1.66 mmol) was added at 40° C. and the mixture was stirred for 2 h. At this point dry YT-II-83 (0.48 g, 1.38 mmol) and DBU (0.26 mL, 1.66 mmol) were added to the mixture and stirring continued for 2 h at 40° C. The reaction solution was then cooled with an ice-water bath, after which water was added to precipitate a solid. This material was further purified by flash chromatography on silica gel (gradient elution, CH$_2$Cl$_2$:MeOH 20:1, 15:1, 10:1) to provide the bivalent YT-III-10 as a white solid (0.68 g, 70%): mp 153-159° C.; IR (KBr) ν 3447, 2929, 1720, 1645 cm$^{-1}$; $^1$H NMR (300 MHz, CDCl$_3$) δ 2.28 (m, 3H), 2.43 (m, 2H), 3.31 (s, 3H), 3.58 (m, 2H), 3.87 (m, 1H), 4.53 (br s, 1H), 4.60 (t, 4H), 4.81 (d, 1H, J=4.41 Hz), 5.27 (br s, 1H), 7.35 (dd, 1H), 7.44 (d, 1H, J=5.13 Hz), 7.68 (dd, 1H, J=1.47, 1.47 Hz), 7.82 (dd, 1H), 7.87 (s, 1H), 7.92 (s, 1H), 8.12 (d, 1H, J=1.47 Hz), 8.32 (d, 1H, J=1.38 Hz); MS (EI) m/e (relative intensity) 694 (M$^+$, 41), 345(35), 317(60), 273(55), 245(100), 217 (31). Anal. Calcd. for C$_{31}$H$_{26}$BrClN$_6$O$_6$.0.4H$_2$O: C, 53.06; H, 3.86; N, 11.98. Found: C, 53.12; H, 3.76; N, 11.67.

(S)-3-(8-Chloro-5-Methyl-5,6-Dihydro-4H-Benzo-[f]-Imidazo-[1,5-a]-[1,4]-Diazepine-3-Carbonyloxy)-Propyl-7-Ethynyl-9-Oxo-11,12,13,13a-Tetrahydro-9H-Benzo-[e]-Imidazo-[5,1-c]-Pyrrolo-[1,2-a]-[1,4]-Diazepine-1-Carboxylate) (YT-III-28)

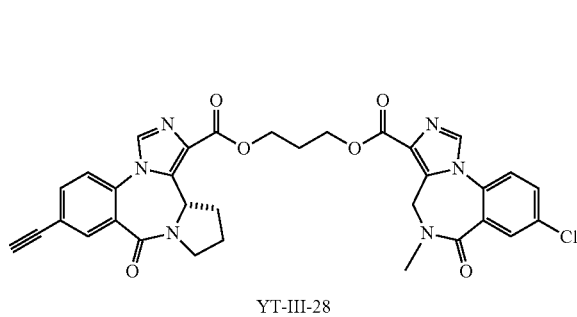

YT-III-28

YT-III-28 was prepared in 70% yield using the procedure described above: mp 174-176° C.; IR (KBr) ν 2923, 1717, 1634 cm$^{-1}$; $^1$H NMR (300 MHz, CDCl$_3$) δ 2.28 (m, 3H), 2.42 (m, 2H), 3.26 (s, 1H), 3.28 (s, 3H), 3.66 (m, 2H), 3.85 (m, 1H), 4.40 (br s, 1H), 4.60 (t, 4H), 4.78 (d, 1H, J=6.69 Hz), 5.23 (br s, 1H), 7.38 (d, 1H, J=2.69 Hz), 7.40 (d, 1H, J=3.02 Hz), 7.64 (dd, 1H, J=2.49, 2.37 Hz), 7.76 (dd, 1H, J=1.96, 1.94 Hz), 7.84 (s, 1H), 7.88 (s, 1H), 8.08 (d, 1H, J=2.37 Hz), 8.27 (d, 1H, J=1.95 Hz); HRMS (CI) calcd for C$_{33}$H$_{27}$ClN$_6$O$_6$ (M+H)$^+$ 639.1759, found 639.1762.

3-(8-Chloro-5-Methyl-5,6-Dihydro-4H-Benzo-[f]-Imidazo-[1,5-a]-[1,4]-Diazepine-3-Carbonyloxy)-Propyl-8-Ethynyl-6-Phenyl-4H-Benzo-[f]-Imidazo-[1,5-a]-[1,4]-Diazepine-3-Carboxylate (YT-III-15)

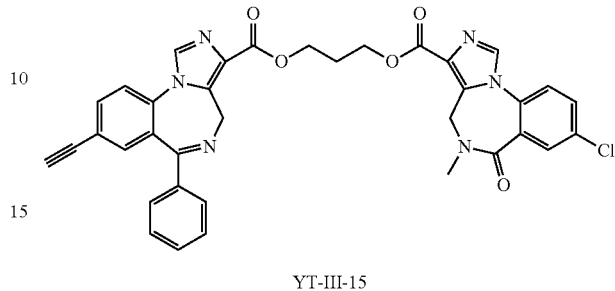

YT-III-15

YT-III-15 was prepared in 70% yield using the procedure described above: mp: 179-184° C.; IR (KBr) 3433, 2929, 1718, 1646, 1497, 1361, 1255, 1157, 1121, 1065, 949, 831, 769, 697, 658 cm$^{-1}$. $^1$H NMR (300 MHz, CDCl$_3$) δ 2.39 (m, 2H), 3.26 (s, 3H), 4.10 (d, 1H, J=12.6 Hz), 4.40 (br s, 1H), 4.60 (m, 5H), 5.22 (br s, 1H), 6.07 (d, 1H, J=12.3 Hz), 7.59 (m, 8H), 7.64 (dd, 1H, J=2.40, 2.43 Hz), 7.80 (dd, 1H, J=1.91, 1.05 Hz), 7.88 (s, 1H), 7.95 (s, 1H), 8.09 (d, 1H, J=2.39 Hz); MS (EI) m/e (relative intensity) 658 (M$^+$, 23), 368(36), 309 (23), 273(62), 245(100), 217(28), 185(32), 152(54), 129 (94). Anal. Calcd. for C$_{36}$H$_{27}$ClN$_6$O$_5$·0.5CH$_2$Cl$_2$: C, 62.69; H, 4.03; N, 12.03. Found: C, 62.68; H, 4.03; N, 12.10. (CHN sample was transferred to a vial for drying with CH$_2$Cl$_2$ which may explain the contaminant.)

5-(8-Chloro-5-Methyl-6-Oxo-5,6-Dihydro-4H-Benzo-[f]-Imidazo-[1,5-a]-[1,4]-Diazepine-3-Carbonyloxy)-Pentyl-8-Ethynyl-6-Phenyl-4H-Benzo-N-Imidazo-[1,5-a]-[1,4]-Diazepine-3-Carboxylate (YT-III-341)

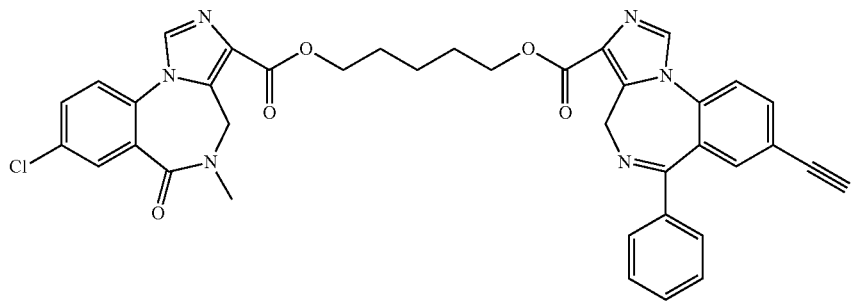

YT-III-341

YT-III-341 was prepared in 72% yield using the procedure described above: mp: 155-160° C. (started to decompose at 120° C.); IR (KBr) 3290, 2956, 1720, 1644, 1612, 1563 cm$^{-1}$; $^1$H NMR (300 MHz, CDCl$_3$) δ 1.89 (m, 6H), 3.21 (s, 1H), 3.25 (s, 3H), 4.06 (d, 2H, J=8.47 Hz), 4.42 (m, 4H), 5.21 (br s, 1H), 6.08 (d, 1H, J=10.9 Hz), 7.59 (m, 8H), 7.64 (dd, 1H, J=2.53, 2.47 Hz), 7.80 (dd, 1H, J=1.81, 1.64 Hz), 7.87 (s, 1H), 7.95 (s, 1H), 8.08 (d, 1H, J=2.39 Hz); MS (EI) m/e (relative intensity) 687 (M$^+$, 24), 689 (M+2, 8), 310 (22), 154 (100). Anal. Calcd. for C$_{38}$H$_{31}$ClN$_6$O$_5$· 0.5CH$_2$Cl$_2$: C, 63.41; H, 4.42; N, 11.52. Found: C, 63.37; H, 4.72; N, 11.63. (CHN sample was transferred to a vial for drying with CH$_2$Cl$_2$ which may explain the contaminant.)

5-(8-Chloro-5-Methyl-6-Oxo-5,6-Dihydro-4H-Benzo-[f]-Imidazo-[1,5-a]-[1,4]-Diazepine-3-Carbonyloxy)-Pentyl-8-Ethynyl-6-(2-Fluorophenyl)-4H-Benzo-[f]-Imidazo-[1,5-a]-[1,4]-Diazepine-3-Carboxylate (YT-III-342)

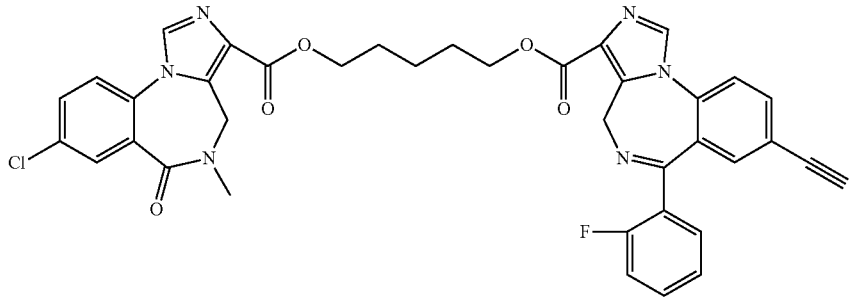

YT-III-342

YT-III-342 was prepared in 73% yield using the procedure described above: mp 125-130° C.; IR (KBr) ν 3293, 3054, 2957, 1721, 1643 cm$^{-1}$; $^1$H NMR (300 MHz, CDCl$_3$) δ 1.9 (m, 6H), 3.19 (s, 1H), 3.25 (s, 3H), 4.41 (m, 8H), 7.66 (m, 7H), 7.68 (dd, 1H, J=1.34, 2.44 Hz), 7.77 (dd, 1H, J=1.78, 1.75 Hz), 7.87 (s, 1H), 7.96 (s, 1H), 8.08 (d, 1H, J=2.38 Hz); MS (EI) m/e (relative intensity) 705 (M$^+$, 100), 707 (M+2, 34), 420 (15), 391 (26), 328 (82), 307 (75), 289 (50), 274 (40), 249 (19). Anal. Calcd. for C$_{38}$H$_{30}$ClFN$_6$O$_5$·0.3CH$_2$Cl$_2$: C, 62.96; H, 4.22; N, 11.50. Found: C, 62.99; H, 4.57; N, 11.29. (CHN sample was transferred to a vial for drying with CH$_2$Cl$_2$ which may explain the contaminant.)

(S)-5-(8-Chloro-5-Methyl-6-Oxo-5,6-Dihydro-4H-Benzo-[f]-Imidazo-[1,5-a]-[1,4]Diazepine-3-Carbonyloxy)-Pentyl-8-Ethynyl-6-(2-Fluorophenyl)-4-Methyl-4H-Benzo-[f]-Imidazo-[1,5-a]-[1,4]-Diazepine-3-Carboxylate (YT-III-33)

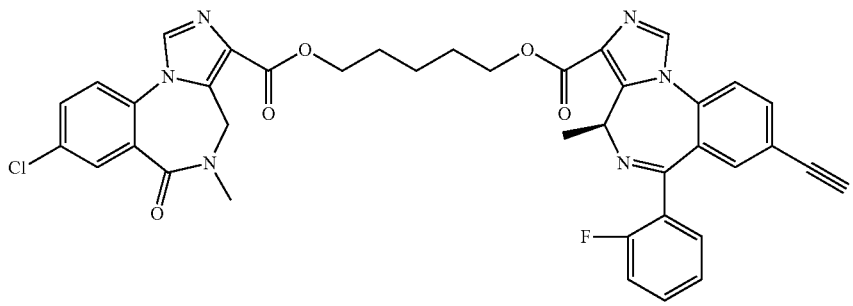

YT-III-33

YT-III-33 was prepared in 72% yield using the procedure described above: mp: 157-162° C. (starts to decompose at 121° C.); IR (KBr) 3292, 3053, 2935, 1709, 1643 cm$^{-1}$; $^1$H NMR (300 MHz, CDCl$_3$) δ 8.09 (d, 1H, J=2.5 Hz), 7.88 (s, 1H), 7.64 (dd, J=2.75, 2.45 Hz, 1H), 7.58 (d, J=8.1 Hz, 1H), 7.49 (m, 7H), 6.96 (s, 1H), 5.26 (bs, 1H), 4.46 (m, 6H), 3.27 (s, 3H), 3.11 (s, 1H), 1.93 (m, 6H), 1.30 (m, 3H); MS (FAB$^+$) m/e (relative intensity) 719 (M$^+$, 58), 721 (M+2, 18), 391 (25), 342 (35), 307 (100), 289 (57), 274 (26), 258 (14); Anal. Calcd for C$_{39}$H$_{32}$FClN$_6$O$_5$·0.5CH$_2$Cl$_2$: C, 62.47; H, 4.37; N, 11.08. Found: C, 62.48; H, 4.68; N, 10.95. (CHN sample was transferred to a vial for drying with CH$_2$Cl$_2$ which may explain the contaminant.)

5-(8-Ethynyl-6-(2-Fluorophenyl)-4H-Benzo-[f]-Imidazo-[1,5-a]-[1,4]-Diazepine-3-Carbonyloxy)-Pentyl-8-Ethynyl-6-Phenyl-4H-Benzo-[f]-Imidazo-[1,5-a]-[1,4]-Diazepine-3-Carboxylate (YT-III-36)

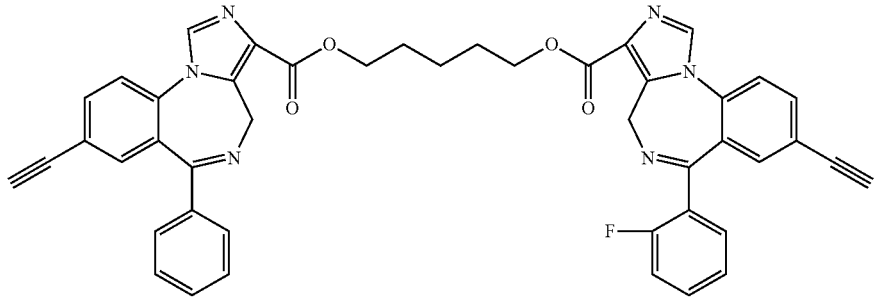

YT-III-36

YT-III-36 was prepared in 72% yield using the procedure described above: mp 145-150° C.; IR (KBr) 3292, 2926, 2855, 1714, 1612 cm$^{-1}$; $^1$H NMR (300 MHz, CDCl$_3$) δ 1.93 (m, 6H), 2.98 (s, 2H), 4.22 (d, 2H, J=20.9 Hz), 4.40 (m, 4H), 6.07 (d, 2H, J=11.5 Hz), 7.58 (m, 15H), 7.95 (d, 2H, J=6.1 Hz); MS (FAB$^+$) m/e (relative intensity) 741 (M$^+$, 28), 391 (33), 310(25), 149 (100). HRMS (EI) calcd for C$_{45}$H$_{33}$FN$_6$O$_4$ is: 741.2626, found 741.2631.

Example 8

Assays Of Competitive Binding To αxβ3γ2 GABAA Receptors

The GABA$_A$ subunit selectivity of several compounds prepared as described above were determined using competitive binding assays. Competition binding assays were performed in a total volume of 0.5 mL at 4° C. for 1 h using [$^3$H] flunitrazepam as the radioligand (Savić, M. M.; Cook, J. M. et al. *Progr. Neuro. Psychopharm. Biol. Psy.* 2010, 34, 376-386). A total of 6 μg of cloned human GABA$_A$ receptor DNA containing desired α subtype along with β2 and γ2 subunits were used for transfecting HEK 293T cell line using Fugene 6 (Roche Diagnostic) transfecting reagent. Cells were harvested 48 h after transfection, washed with Tris-HCl buffer (pH 7.0) and Tris Acetate buffer (pH 7.4) and resulting pellets were stored at −80° C. until assayed. On the day of the assay, pellets containing 20-50 μg of GABA$_A$ receptor harvested with hypotonic buffer (50 mM Tris-acetate, pH 7.4, at 4° C.) was incubated with the radiolabel as previously described. Non-specific binding was defined as radioactivity bound in the presence of 100 μM diazepam and represented less than 20% of total binding. Membranes were harvested with a Brandel cell harvester followed by three ice-cold washes onto polyethyleneimine-pretreated (0.3%) Whatman GF/C filters. Filters were dried overnight and then soaked in Ecoscint A liquid scintillation cocktail (National Diagnostics; Atlanta, Ga.). Bound radioactivity was quantified by liquid scintillation counting. Membrane protein concentrations were determined using an assay kit from Bio-Rad (Hercules, Calif.) with bovine serum albumin as the standard.

Results for various compounds are illustrated in FIGS. 5, 8, 9 and 11-13.

Example 9

Electrophysiological Experiments

Oocytes were injected according to a standard method (Savic et al. *Prog. Neuropsychopharmacol. Biol. Psychiatry* 2010, 34(2):376-386) with different combinations of cDNA's comprised of different α-GABAergic cDNA's in combination with β3 and γ2 GABAergic cDNAs to express the different GABA$_A$ ion channels, represented in FIGS. 6-13 (Savic et al. *Prog. Neuropsychopharmacol. Biol. Psychiatry* 2010, 34(2):376-386). These were used for the oocyte studies, applying an EC3 of GABA and then the drug being tested. For electrophysiological recordings, oocytes were placed on a nylon-grid in a bath of *Xenopus* Ringer solution (XR, containing 90 mM NaCl, 5 mM HEPES-NaOH (pH 7.4), 1 mM MgCl$_2$, 1 mM KCl and 1 mM CaCl$_2$). The oocytes were constantly washed by a flow of 6 ml/min XR which could be switched to XR containing GABA and/or drugs. Drugs were diluted into XR from DMSO-solutions resulting in a final concentration of 0.1% DMSO perfusing the oocytes.

Drugs were preapplied for 30 sec before the addition of GABA, which was coapplied with the drugs until a peak response was observed. Between two applications, oocytes were washed in XR for up to 15 min to ensure full recovery from desensitization. For current measurements the oocytes were impaled with two microelectrodes (2-3 mΩ) which were filled with 2 mM KCl. All recordings were performed at room temperature at a holding potential of −60 mV using a Warner OC-725C two-electrode voltage clamp (Warner Instruments, Hamden, Conn.). Data were digitized, recorded and measured using a Digidata 1322A data acquisition system (Axon Instruments, Union City, Calif.). Results of concentration response experiments were fitted using GraphPad Prism 3.00 (GraphPad Software, San Diego, Calif.).

The equation used for fitting concentration response curves was Y=Bottom+(Top−Bottom)/(1+10^((LogEC50−X)*HillSlope)); X represents the logarithm of concentration, Y represents the response; Y starts at Bottom and goes to Top with a sigmoid shape. This is identical to the "four parameter logistic equation."

Concentration—effect curves were prepared for various compounds tested on α1β3γ2, α2β3γ2, α3β3γ2, α5β3γ2 GABA$_A$ receptors, using an EC3 GABA concentration.

Results are shown in FIGS. 6-13. Data points represent mean±SEM from at least four oocytes from ≥2 batches.

Example 10

Data in Rhesus Monkeys

Three rhesus monkeys were trained on a multiple schedule of reinforcement as described in detail by Rowlett et al. (2006) (Rowlett et al. *Psychopharmacology* (Berl.) 184, 201-211). Monkeys had various durations of exposure to this procedure. A daily session consisted of 4 cycles, each preceded by a 10 min time out period in which all lights in the chamber were off and responding had no programmed consequences. Each cycle consisted of two components. The first component was signaled by red stimulus lights and consisted of a fixed ratio 18 (FR18) schedule of food pellet delivery (Bioserve, Frenchtown, N.J.) followed by a 10 s time out. The second component, signaled by green stimulus lights, consisted of the FR 18 schedule of food delivery combined with a FR 20 schedule of foot shock delivery (1.5e3.0 mA, adjusted for each monkey based on individual performance, 0.25 s duration). Delivery of a food pellet was followed by a 10 s time out in which responding had no scheduled consequences. Both components were 5 min in duration, or ended after the monkey obtained 5 food pellets or received 3 foot shocks, whichever occurred first.

Test sessions were conducted once or twice per week when monkeys reached stable performance, defined as the average rates of responding for component 1 and component 2 not varying by ±20% over five consecutive sessions, with no upward or downward trends. During test sessions, i.v. injections of vehicle or drug were administered in the 5th minute of each time out (i.e., 5 min prior to the beginning of each cycle). In successive cycles, increasing doses of the test drug were administered using a cumulative dosing procedure. The dependent measure was the average rates of responding (responses/s), calculated by dividing responses by time during components 1 and 2, excluding responding during time outs or reinforcer delivery.

Figure 14:
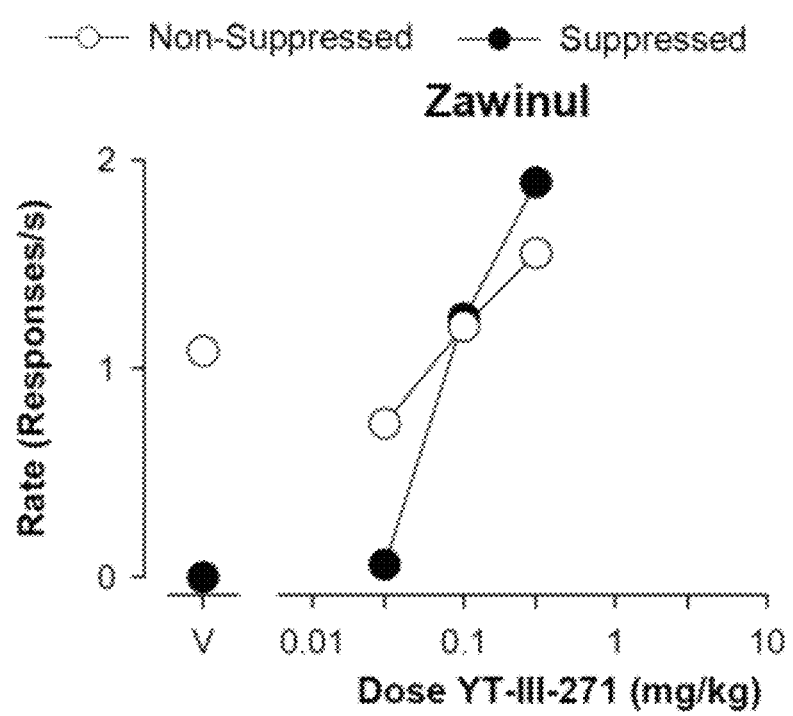
FIG. 14 shows the vogel conflict assessment of anxiolytic and sedating effects in a rhesus monkey.
Figure 15:
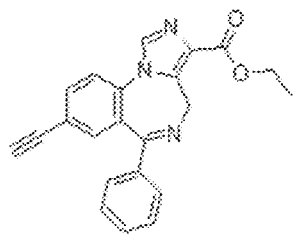
FIG. 15 shows the structures of exemplary compounds, as well as stabilities of compounds in human liver microsomes.
Figure 15:
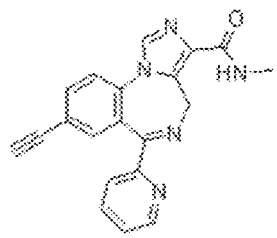
Figure 15:
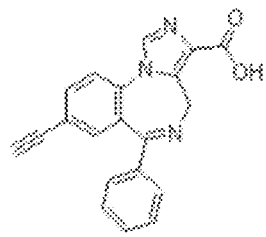
Figure 15:
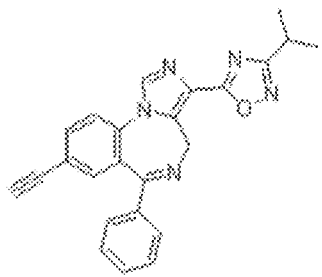
Figure 15:
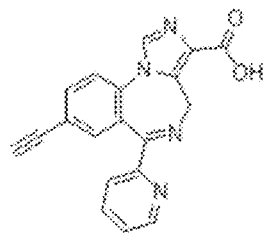
Figure 15:
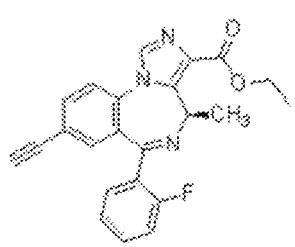
Figure 15:
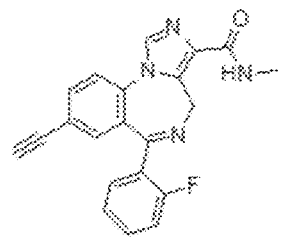
Figure 15:
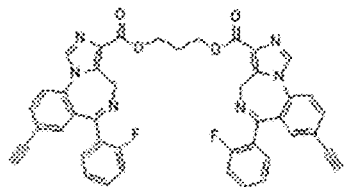
Figure 15:
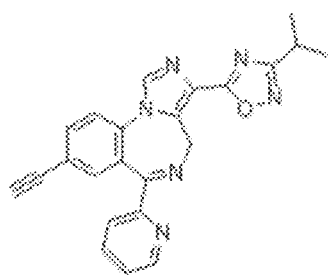
Figure 15:
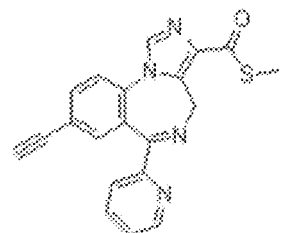
Figure 15:
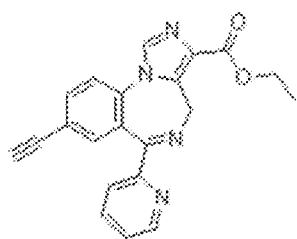
Figure 15:
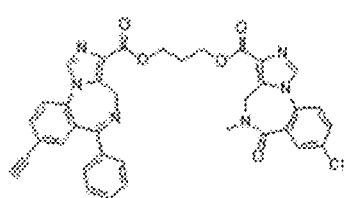
Figure 15:
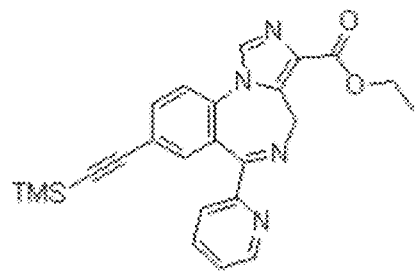
Figure 15:
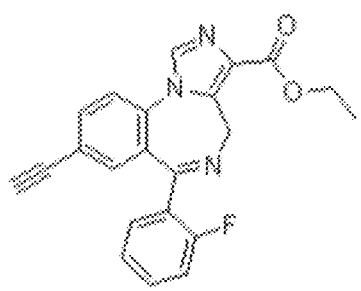
Figure 15:
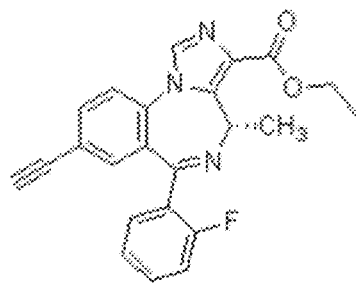

Data for one monkey are presented in FIG. 14. As shown therein, YT-III-271 is clearly anxiolytic (suppressed responding) and nonsedating (non-suppressed responding). Data for the other two monkeys was inconclusive.

Example 11

Metabolic Stability for 15 $GABA_A$ Receptor Ligands Using Human Liver Microsomes The metabolic stability of 15 $GABA_A$ receptor ligands using human liver microsomes was studied. The test articles were incubated at two concentrations (1 and 10 μM) and aliquots (100 μl) were removed at various time points (0, 15, 30 and 60 minutes), and analyzed by LC-MS/MS.

Significant metabolism was observed at both 1 and 10 μM for XHe-II-053 (less than 14% remaining at 30 min), HZ-166-TMS (less than 14% remaining at 60 min), JY-XHe-053 (less than 20% remaining at 15 min) and SH-053-2'F-$SCH_3$ (less than 12% remaining at 15 min). Metabolism was observed at only 1 μM for YT-III-15 (approximately 5% remaining at 60 min) and YT-III-271 (approximately 52% remaining at 60 min). No significant metabolism was observed for the other test articles.

Objective of Study

The objective of this study was to evaluate the in vitro metabolic stability of 15 $GABA_A$ receptor ligands using human liver microsomes. The purpose of this study was to provide data that can be used to support research efforts. It was exploratory and not within the scope of U.S. Food and Drug Administration (FDA) "Good Laboratory Practice for Nonclinical Laboratory Studies" (GLP) regulations, as described in 21 CFR Part 58. Nevertheless, the study was planned, performed, recorded, and reported in accordance with standard practices to ensure data quality and integrity.

II. Materials And Methods

Experimental Design

The test articles were incubated at two concentrations (1 and 10 μM) in 96-well plate format with active or heat-inactivated human liver microsomes and cofactors. Aliquots were removed at 0, 15, 30 and 60 minutes and mixed with acetonitrile containing internal standard for analysis. Samples were extracted and assayed using a liquid chromatography/tandem mass spectrometry (LC-MS/MS) analytical method.

B. Test Articles

Test Article 1: XHe-II-053
Test Article 2: XHe-II-053 Acid
Test Article 3: HZ-166
Test Article 4: SR-II-54
Test Article 5: HZ-166-TMS
Test Article 6: HJ-I-40
Test Article 7: EMJ-I-026
Test Article 8: JY-XHe-053
Test Article 9: SH-053-2'F-SCH3
Test Article 10: SH-053-2'F-RCH3
Test Article 11: YT-III-271
Test Article 12: YT-III-15
Test Article 13: HJ-I-037
Test Article 14: ZJW-II-065
Test Article 15: ZJW-II-040

Preparation of Test Articles: Test articles were prepared as stock solutions in DMSO and stored in aliquots at −20° C. On the day of the experiment, the test articles were diluted in the 100 mM phosphate buffer (pH 7.4) to achieve appropriate final concentrations.

Test Article Handling: Test article, stock solutions and incubation samples were handled with the use of eye protection, gloves, and a laboratory coat. An MSDS or equivalent document was available with recommended procedures for safe handling of the test article, for handling an accidental spill, and for disposal of the waste contaminated with the test articles C. Test System—Liver Microsomes Supplier: Pooled human liver microsomes (Lot #38289, pool of 150 different male and female donor livers) were obtained from BD Biosciences Corporation (Woburn, Mass.). Microsomes were stored at ~−135° C. until use.

Justification: The liver is the major site of metabolism of most organic chemicals, both endogenous and foreign. Microsomes contain many of the enzymes that may be involved in a drug's metabolism.

D. In Vitro Incubation Conditions

The test articles (1 and 10 μM) were incubated with human liver microsomes (0.5 mg protein/ml) and appropriate cofactors (2.5 mM NADPH and 3.3 mM magnesium chloride) in 100 mM phosphate buffer, pH 7.4 (0.1% final DMSO), in a 37° C. water bath. Incubations with all compounds were initiated with the addition of microsomes. At selected time points (0, 15, 30 and 60 min), a single 100 μl aliquot was removed from each sample and mixed with 200 μl of chilled acetonitrile containing internal standard. Following brief vortexing and centrifugation, the samples were further diluted into a 96-well plate for subsequent LC-MS/MS analysis. All samples were assayed in duplicate.

Experimental controls consisted of: a) incubation of all components except test article for 0 and 60 min, b) incubation of midazolam (positive control) at 10 μM for 0, 15, 30 and 60 min, and c) incubation of 1 and 10 μM test article and 10 μM midazolam with heat-inactivated microsomes (0.5 mg protein/ml) for 0 and 60 min. All controls were assayed in duplicate.

E. LC-MS/MS Analysis of Incubation Samples

Samples were analyzed by LC-MS/MS in multiple reaction monitoring mode using positive-ion electrospray ionization. The details of the LC-MS/MS method can be provided upon request.

LC Conditions:
Pumps: Shimadzu LC-20AD
Autosampler: Leap Technologies CTC HTS PAL
Autosampler Temperature: 10° C.
Column: Phenomenex Luna C18(2), 2×50 mm, 5 μm
Column Temperature: Ambient
Mobile Phase: A=MilliQ Water with 0.1% (v) formic acid
B=Acetonitrile with 0.1% (v) formic acid
Elution Mode: Gradient:
Time (min) % A % B Flow rate (ml/min)
98 2 1.0
98 2 1.0
2.0 2 98 1.0
2.6 2 98 1.0
2.8 98 2 1.0
4.1 98 2 1.0
Injection Volume: 10 μl
Compound Retention Time (min)
XHe-II-053 1.96
XHe-II-053 Acid 1.82
HZ-166 1.86
SR-II-54 1.75
HZ-166-TMS 2.11
HJ-I-40 1.78
EMJ-I-026 2.10
JY-XHe-053 1.95
SH-053-2'F-SCH3 1.99
SH-053-2'F-RCH3 1.99
YT-III-271 2.02
YT-III-15 1.95
HJ-I-037 1.88
E. LC-MS/MS Analysis of Incubation Samples Samples were analyzed by LC-MS/MS in multiple reaction monitoring mode using positive-ion electrospray ionization. The details of the LC-MS/MS method can be provided upon request.

LC Conditions:
Pumps: Shimadzu LC-20AD
Autosampler: Leap Technologies CTC HTS PAL
Autosampler Temperature: 10° C.
Column: Phenomenex Luna C18(2), 2×50 mm, 5 μm
Column Temperature Ambient
Mobile Phase: A=MilliQ Water with 0.1% (v) formic acid
B=Acetonitrile with 0.1% (v) formic acid
Elution Mode: Gradient:
Time (min) % A % B Flow rate (ml/min)
98 2 1.0
98 2 1.0
2.0 2 98 1.0
2.6 2 98 1.0
2.8 98 2 1.0
4.1 98 2 1.0
Injection Volume: 10 μl
Compound Retention Time (min)
XHe-II-053 1.96
XHe-II-053 Acid 1.82
HZ-166 1.86
SR-II-54 1.75
HZ-166-TMS 2.11
HJ-I-40 1.78
EMJ-I-026 2.10
JY-XHe-053 1.95
SH-053-2'F-SCH3 1.99
SH-053-2'F-RCH3 1.99
YT-III-271 2.02
YT-III-15 1.95
HJ-I-037 1.88
ZJW-II-065 1.93
ZJW-II-040 1.99
Benzyl nicotinate (Int. Std.) 1.94
Midazolam (Control) 1.71
Ethyl nicotinate (Int. Std.) 1.76
MS Conditions:
Instrument: Applied Biosystems 4000 QTRAP
Ionization Mode: Turbo Spray Electrospray ionization, positive ion, (ESI+)
Curtain Gas: 30 psi
Ion Spray Voltage: 4000
Temperature: 450° C.
Detection Mode: Multiple Reaction Monitoring (MRM)
Quantitation: Integration and Quantitation by Analyst Software Ver. 1.4.2

MRM Transitions Dwell Times were 40 msec per analyte. The mass spectrometer was operated at unit mass resolution.

| Compound Name | Scan/mass | DP | CE | CXP |
|---|---|---|---|---|
| XHe-II-053 | 356.1→156.0 | 61 | 57 | 26 |
| XHe-II-053 Acid | 328.1→231.0 | 66 | 31 | 18 |
| HZ-166 | 357.1→283.1 | 66 | 43 | 16 |
| SR-II-54 | 329.1→285.0 | 61 | 23 | 16 |
| HZ-166-TMS | 429.2→355.1 | 46 | 47 | 20 |
| HJ-I-40 | 342.2→311.0 | 76 | 31 | 18 |
| EMJ-I-026 | 394.1→310.0 | 71 | 31 | 18 |
| JY-XHe-053 | 374.1→328.0 | 61 | 21 | 18 |
| SH-053-2'F-SCH3 | 388.1→342.0 | 66 | 25 | 8 |
| SH-053-2'F-RCH3 | 388.1→341.9 | 61 | 25 | 8 |
| YT-III-271 | 731.2→328.0 | 1 | 69 | 18 |
| YT-III-15 | 659.2→310.0 | 1 | 57 | 16 |
| HJ-I-037 | 359.1→152.0 | 71 | 61 | 26 |
| ZJW-II-065 | 359.1→283.0 | 56 | 41 | 16 |
| ZJW-II-040 | 395.1→283.0 | 66 | 43 | 16 |
| Benzyl nicotinate (Int. Std.) | 152.1→123.9 | 61 | 22 | 16 |
| Midazolam (Control) | 326.0→291.0 | 61 | 38 | 16 |
| Ethyl nicotinate (Int. Std.) | 214.0→91.0 | 61 | 35 | 16 |

F. Data Analysis

Data from the metabolic stability assays were transferred to and processed in a Microsoft Excel spreadsheet. To determine metabolic stability, the percent remaining at each time point was calculated by dividing the peak area ratio of test article/internal standard at each time point by the peak area ratio at 0 min multiplied by 100.

G. Retention of Records and Study Samples

The final report, raw data, supporting documents, and records specific to this study will be retained and stored in the Records Center at SRI International, 333 Ravenswood Avenue, Menlo Park, Calif. 94025. All records will be maintained for at least 5 years. At the end of the retention period, the Sponsor will be contacted regarding further disposition of these records.

No residual study samples (incubation extracts) will be kept at SRI. Unused bulk test article will be returned to the Sponsor after completion of the study and acceptance of the Final Report.

III. Results and Discussion

The results for the metabolic stability of all 15 test articles using pooled human liver microsomes are summarized in Tables 1, 2 and 3. Significant metabolism was observed at both concentrations tested (1 and 10 µM) for XHe-II-053 (less than 14% remaining at 30 min), HZ-166-TMS (less than 14% remaining at 60 min), JY-XHe-053 (less than 20% remaining at 15 min) and SH-053-2'F-SCH3 (less than 12% remaining at 15 min). Metabolism was observed at only 1 µM for YT-III-15 (approximately 5% remaining at 60 min) and YT-III-271 (approximately 52% remaining at 60 min). No significant metabolism was observed for the other test articles.

When incubated with heat-inactivated human liver microsomes, there was no significant change in the % remaining of any of the 15 compounds after 60 minutes. This suggests that the compounds are stable in the incubation conditions used in these experiments. The results for the metabolic stability of midazolam using active and heat-inactivated human liver microsomes are summarized in Table 4. Midazolam was consistently metabolized in all experiments, indicating that the incubation conditions used were suitable for determining metabolic stability.

TABLE 1

IN VITRO METABOLIC STABILITY OF XHE-II-053(1), XHE-II-043 ACID(2), HZ-166(3), SR-II-54(4), HZ-166-TMS(5) USING HUMAN LIVER MICROSOMES

| Test Article | Time, min | Mean % Remaining vs T = 0 min[a] Human Liver Microsomes | |
|---|---|---|---|
| | | 1 µM[b] | 10 µM[b] |
| XHe-II-053 | 15 | 41.4 | 47.6 |
| | 30 | 11.1 | 13.9 |
| | 60 | 1.46 | 1.74 |
| XHe-II-053 with HI[c] Microsomes | 60 | 107 | 102 |
| XHe-II-043 Acid | 15 | 108 | 95.6 |
| | 30 | 106 | 95.0 |
| | 60 | 111 | 95.0 |
| XHe-II-043 Acid with HI[c] Microsomes | 60 | 106 | 97.4 |
| HZ-166 | 15 | 106 | 104 |
| | 30 | 98.4 | 90.7 |
| | 60 | 80.4 | 76.3 |
| HZ-166(3) with HI[c] Microsomes | 60 | 94.1 | 95.4 |
| SR-II-54 | 15 | 102 | 91.4 |
| | 30 | 94.7 | 86.1 |
| | 60 | 110 | 86.9 |
| SR-II-54 with HI[c] Microsomes | 60 | 97.4 | 88.7 |

TABLE 1-continued

IN VITRO METABOLIC STABILITY OF XHE-II-053(1), XHE-II-043 ACID(2), HZ-166(3), SR-II-54(4), HZ-166-TMS(5) USING HUMAN LIVER MICROSOMES

| Test Article | Time, min | Mean % Remaining vs T = 0 min[a] Human Liver Microsomes | |
|---|---|---|---|
| | | 1 µM[b] | 10 µM[b] |
| HZ-166-TMS | 15 | 78.0 | 77.1 |
| | 30 | 35.9 | 43.8 |
| | 60 | 7.8 | 13.8 |
| HZ-166-TMS with HI[c] Microsomes | 60 | 108 | 84.7 |

[a] % remaining at T = 0 is 100%
[b] Samples were assayed in duplicate.
[c] HI = Heat Inactivated

TABLE 2

IN VITRO METABOLIC STABILITY OF HJ-I-40(6), EMJ-I-026(7), JY-XHE-053(8), SH-053-2'F-SCH3(9), SH-053-2'F-RCH3(10) USING HUMAN LIVER MICROSOMES

| Test Article | Time, min | Mean % Remaining vs T = 0 min[a] Human Liver Microsomes | |
|---|---|---|---|
| | | 1 µM[b] | 10 µM[b] |
| HJ-I-40 | 15 | 109 | 104 |
| | 30 | 126 | 106 |
| | 60 | 136 | 110 |
| HJ-I-40 with HI[c] Microsomes | 60 | 110 | 110 |
| EMJ-I-026 | 15 | 100 | 109 |
| | 30 | 107 | 108 |
| | 60 | 91.4 | 96.6 |
| EMJ-I-026 with HI[c] Microsomes | 60 | 137 | 119 |
| JY-XHe-053 | 15 | 13.5 | 20.0 |
| | 30 | 2.13 | 3.60 |
| | 60 | 0.27 | 0.56 |
| JY-XHe-053 with HI[c] Microsomes | 60 | 102 | 111 |
| SH-053-2'F-SCH3 | 15 | 6.18 | 11.7 |
| | 30 | 0.85 | 1.72 |
| | 60 | 3.85[d] | 0.20 |
| SH-053-2'F-SCH3 with HI[c] Microsomes | 60 | 110 | 114 |
| SH-053-2'F-RCH3 | 15 | 86.7 | 97.9 |
| | 30 | 86.7 | 105 |
| | 60 | 86.9 | 105 |
| SH-053-2'F-RCH3 with HI[c] Microsomes | 60 | 115 | 117 |

[a] % remaining at T = 0 is 100%
[b] Samples were assayed in duplicate.
[c] HI = Heat Inactivated
[d] Suspected contamination, if deleted value = 0.20

TABLE 3

IN VITRO METABOLIC STABILITY OF YT-III-271(11), YT-III-15(12), HJ-I-037(13), ZJW-II-065(14), AND ZJW-II-040(15) USING HUMAN LIVER MICROSOMES

| Test Article | Time, min | Mean % Remaining vs T = 0 min[a] Human Liver Microsomes | |
|---|---|---|---|
| | | 1 µM[b] | 10 µM[b] |
| YT-III-271 | 15 | 97.1 | 104 |
| | 30 | 83.5 | 102 |
| | 60 | 52.0 | 91.1 |

TABLE 3-continued

IN VITRO METABOLIC STABILITY OF YT-III-271(11),
YT-III-15(12), HJ-I-037(13), ZJW-II-065(14), AND
ZJW-II-040(15) USING HUMAN LIVER MICROSOMES

| Test Article | Time, min | Mean % Remaining vs T = 0 min[a] Human Liver Microsomes | |
|---|---|---|---|
| | | 1 μM[b] | 10 μM[b] |
| YT-III-271 with HI[c] Microsomes | 60 | 117 | 97.0 |
| YT-III-15 | 15 | 87.3 | 107 |
| | 30 | 39.4 | 104 |
| | 60 | 5.2 | 82.8 |
| YT-III-15(12) with HI[c] Microsomes | 60 | 141 | 114 |
| HJ-I-037 | 15 | 97.7 | 96.8 |
| | 30 | 99.5 | 103 |
| | 60 | 92.7 | 103 |
| HJ-I-037 with HI[c] Microsomes | 60 | 117 | 108 |
| ZJW-II-065 | 15 | 98.4 | 111 |
| | 30 | 97.0 | 106 |
| | 60 | 82.5 | 95.6 |
| ZJW-II-065 with HI[c] Microsomes | 60 | 105 | 110 |
| ZJW-II-040 | 15 | 97.8 | 106 |
| | 30 | 98.7 | 99.3 |
| | 60 | 89.4 | 95.1 |
| ZJW-II-040 with HI[c] Microsomes | 60 | 113 | 92.0 |

[a]% remaining at T = 0 is 100%
[b]Samples were assayed in duplicate.
[c]HI = Heat Inactivated

TABLE 4

IN VITRO METABOLIC STABILITY OF MIDAZOLAM
USING HUMAN LIVER MICROSOMES

| Test Article | Time, min | Mean % Remaining vs T = 0 min[a] Human Liver Microsomes 10 μM[b] |
|---|---|---|
| Midazolam | 15 | 36.9 ± 13.5 |
| | 30 | 18.7 ± 7.3 |
| | 60 | 4.2 ± 2.2 |
| Midazolam with HI[c] Microsomes | 60 | 104 ± 1.2 |

[a]% remaining at T = 0 is 100%
[b]Data from three experiments (samples were assayed in duplicate in each experiment).
[c]HI = Heat Inactivated Example 12

Tolerance Studies

In this study, Sprague Dawley rats will be used (average weight 150 gm). Three groups of 8 rats each will be treated with the candidate compound in the following manner: Group 1 will receive chronic 5-day dosing of the candidate drug. The scMet $ED_{50}$ of a compound will be administered via the ip route once daily for 5 consecutive days. In Group 2 identified as the acute dosing group methylcellulose will be administered ip as a 4-day solvent control and a single dose of compound will be acutely administered ip on day 5. Finally, Group 3 will be the solvent control group. These animals will be administered the test solvent (methylcellulose 0.5%) as a control. Here methylcellulose will be administered i.p. for all 5 days.

On day 5, all animals from each group will be tested in the scMet model using the previously determined time of peak effect (TPE) of 15 minutes. Immediately after testing, blood will be collected via cardiac puncture. Samples will be spun down, plasma collected and acetonitrile added. Samples will be frozen at −80° C. and shipped to a commercial laboratory for analysis.

Example 13

Evaluation for Treatment of Schizophrenia

Compounds may be evaluated as generally described in Gill et al. *Neuropsychopharmacology* (2011) 36, 1903-1911.

Animals

Experiments will be conducted according to the guidelines established by the National Institutes of Health Guide for the Care and Use of Laboratory Animals. All electrophysiological recordings and behavioral experiments will be conducted in adult male offspring of MAM- and SAL-treated rats.

Methylazoxymethanol Treatment

MAM treatments will be performed as described previously (Moore et al, 2006). In brief, timed pregnant female Sprague-Dawley rats (Hilltop) will be obtained on GD 15 and individually housed in ventilated plastic breeding tubs. MAM (20 mg/kg, i.p.) will be administered on GD 17. Control dams will receive injections of SAL (1 ml/kg, i.p.). Male pups will be weaned-off on day 21 and pair-housed with littermates, until approximately 3-4 months of age, at which time they will be used for physiological or behavioral experiments. Multiple litters of MAM- and SAL-treated rats can be used for the completion of this study.

Electrophysiological Recording

Animals will be anesthetized with an initial dose of chloral hydrate (Sigma, 400 mg kg, i.p.) and supplemented periodically (i.v.) to maintain a suppression of the hindlimb withdrawal reflex. After being placed in a stereotaxic frame (Kopf), rats will be implanted with a catheter in the lateral tail vein to allow for intravenous injections. Body temperature will be maintained at 37° C. with a temperature-controlled heating pad. In vivo extracellular recordings will be conducted using single glass microelectrodes (e.g., WPI; impedance 6-8 MO) filled with a 2% Chicago Sky Blue (Sigma) solution in 2M NaCl. Electrodes will be placed in the VTA (AP, 5.3 mm; ML, +0.6 mm from bregma, and 6.5 to 9.0 mm ventral of brain surface) or ventral HPC (AP, 5.3 mm; ML, +5.3 mm from bregma, and 5.5 to 8.5 mm ventral of brain surface) using a hydraulic microdrive (Kopf). The population activity of DA neurons will be determined by counting the number of spontaneously firing DA neurons encountered while making 6-9 vertical passes (each track separated by 200 mm). Spontaneous neural activity will be monitored in each track with open filter settings (low pass ¼ 50 Hz; high pass ¼ 16 kHz), until an individual neuron is encountered that meets the electrophysiological criteria of DA neurons established previously (Grace et al. *Neuroscience* (1983). 10: 301-315). The activity of each DA neuron will be recorded for 5 min. Three parameters of activity will be measured: (1) population activity (defined as the number of spontaneously active DA neurons recorded per electrode track), (2) basal firing rate, and (3) the proportion of action potentials occurring in bursts (bursts defined as the occurrence of two spikes with an interspike interval of 80 ms, and the termination of the burst defined as the occurrence of an interspike interval of 160 ms) (Grace et al. *Neuroscience* (1983). 10: 301-315). For recordings in the ventral HPC, neurons will be selected, based on short-latency (o10 ms) evoked responses to stimulation of entorhinal cortex (0.5 Hz). A concentric bipolar electrode (NEX-100X; Rhodes Medical Instruments) will be implanted in the entorhinal cortex (301 angle; AP, 6.6 mm; ML, +1.6 mm from bregma, and 8.5 mm ventral to top of skull). A dual output stimulator (S8800; Grass Technologies) will be used to generate single current pulses (duration, 0.20 ms; intensity 300 mA) in the entorhinal cortex, while the recording microelectrode will be advanced slowly into the ventral HPC.

Amphetamine-Induced Locomotion

Rats used for behavior will be housed in a reverse light/dark cycle (lights on from 1900 to 0700 h) for at least 10 days before the start of behavioral experiments. Rats will be administered the a5GABAAR PAM, test compound (10 mg/kg, i.p.), or SAL (2 ml/kg) 20 min before being placed in an open-field arena (Coulbourn Instruments, Allentown, Pa.) in which spontaneous locomotor activity in the x-y plane will be determined for 30 min by beam breaks and recorded with TruScan software (Coulbourn Instruments). Rats will be then injected with D-amphetamine sulfate (0.5 mg/kg, i.p.) and locomotor activity recorded for an additional 90 min.

Histology

At the completion of the electrophysiological experiments, the recording location will be marked via electrophoretic ejection of Chicago sky blue from the tip of the recording electrode (20 mA constant current, 30 min). Rats used for electrophysiological recordings will be killed with an overdose of anesthetic (chloral hydrate, additional 400 mg/kg, i.v.), whereas rats used for behavioral experiments will be deeply anesthetized with isoflurane before decapitation. All rats used for electrophysiological recordings will be decapitated and their brains removed, fixed for at least 48 h (8% w/v paraformaldehyde in PBS), and cryoprotected (25% w/v sucrose in PBS) until saturated. Brains will be sectioned (60 mm coronal sections), mounted onto gelatin-chrom alum-coated slides, and stained with a mixture of cresyl violet and neutral red for histochemical verification of electrode sites. All histology will be performed with reference to a stereotaxic atlas (Paxinos G, Watson C (Eds.) (1996). The Rat Brain in Stereotaxic Coordinates. Academic: San Diego.).

Analysis

Electrophysiological analysis of DA and ventral HPC neuronal activity will be performed using custom-designed computer software (Neuroscope), whereas locomotor behavior will be recorded using TruScan software. All data will be represented as the mean±SEM, unless otherwise stated. Statistics can be calculated using the SigmaStat software program (Systat Software, San Jose, Calif.).

All patents, publications and references cited herein are hereby fully incorporated by reference. In case of conflict between the present disclosure and incorporated patents, publications and references, the present disclosure should control.

The invention claimed is:

1. A compound of formula (I):

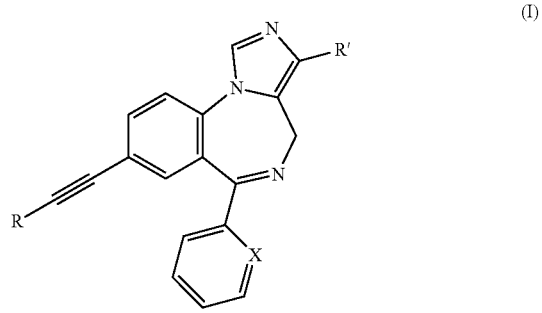

or a salt thereof, wherein:
R is —H or —Si(Me)$_3$;
X is CH, CF, CCl or N; and
R' is selected from the group consisting of —CHF$_2$, —CH$_2$CF$_2$CH$_3$, —CF$_2$CHF$_2$, CF$_2$CF$_2$CH$_3$, —CH$_2$OCH$_3$, —CF$_2$CH$_2$OCH$_3$, —CF$_2$OCH$_2$CH$_3$, —CH$_2$OCH$_2$CH$_3$, —CH$_2$OH, —CH$_2$SCH$_3$, —CF$_2$CH$_2$CH$_3$, —CH$_2$OCH$_2$OCH$_3$, —COCH$_2$CH$_3$, —C(CF$_2$)OCH$_2$CH$_3$, —CH(CF$_3$)OCH$_2$CH$_3$, —CH(CF$_3$)NHCH$_2$CH$_3$,

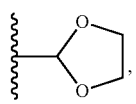

—CHO and —CH$_2$CF$_2$CH$_3$, or

R' is selected from the group consisting of:

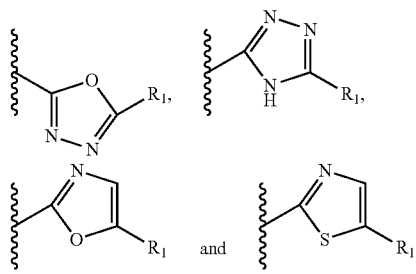

wherein each R1 is independently selected from the group consisting of —CH$_3$, —CH$_2$CH$_3$ and —CH(CH$_3$)$_2$.

2. A pharmaceutical composition comprising a compound of formula (I) according to claim 1, and a pharmaceutically acceptable carrier.

3. A method of treating a disorder selected from an anxiety disorder, epilepsy and schizophrenia in a subject in need of treatment, comprising administering to the subject an effective amount of a compound of formula (I) according to claim 1.

* * * * *